(12) United States Patent
Greco et al.

(10) Patent No.: US 12,390,464 B2
(45) Date of Patent: Aug. 19, 2025

(54) TREATMENT OF EGFR MUTANT-RELATED CANCERS USING A COMBINATION OF EGFR AND CDK4/6 INHIBITORS

(71) Applicant: BETA PHARMA, INC., Wilmington, DE (US)

(72) Inventors: Michael Nicholas Greco, Lansdale, PA (US); Michael John Costanzo, Bonney Lake, WA (US); Michael Alan Green, Easton, PA (US); Don Zhang, Princeton, NJ (US); Jirong Peng, Mequon, WI (US)

(73) Assignee: BETA PHARMA, INC., Wilmington, DE (US)

( * ) Notice: Subject to any disclaimer, the term of this patent is extended or adjusted under 35 U.S.C. 154(b) by 694 days.

(21) Appl. No.: 17/641,868

(22) PCT Filed: Sep. 23, 2020

(86) PCT No.: PCT/US2020/052096
§ 371 (c)(1),
(2) Date: Mar. 10, 2022

(87) PCT Pub. No.: WO2021/061695
PCT Pub. Date: Apr. 1, 2021

(65) Prior Publication Data
US 2022/0347177 A1    Nov. 3, 2022

Related U.S. Application Data

(60) Provisional application No. 62/904,567, filed on Sep. 23, 2019.

(51) Int. Cl.
*A61K 31/506* (2006.01)
*A61P 11/00* (2006.01)
*A61P 35/00* (2006.01)

(52) U.S. Cl.
CPC .......... *A61K 31/506* (2013.01); *A61P 11/00* (2018.01); *A61P 35/00* (2018.01)

(58) Field of Classification Search
CPC ................................................. A61K 31/506
USPC ........................................................ 514/210
See application file for complete search history.

(56) References Cited

U.S. PATENT DOCUMENTS

| | | | | |
|---|---|---|---|---|
| 9,878,994 | B2* | 1/2018 | Greco | C07D 401/14 |
| 10,590,111 | B2* | 3/2020 | Peng | C07D 403/04 |
| 2017/0210726 | A1* | 7/2017 | Greco | A61P 35/02 |
| 2017/0355696 | A1 | 12/2017 | Jiang | |
| 2017/0362203 | A1* | 12/2017 | Peng | C07D 403/14 |
| 2019/0152969 | A1 | 5/2019 | Jiang | |

FOREIGN PATENT DOCUMENTS

| | | |
|---|---|---|
| WO | 2016014904 A1 | 1/2016 |
| WO | 2016094821 A2 | 6/2016 |
| WO | 2018091999 A1 | 5/2018 |
| WO | 2018156812 A1 | 8/2018 |

OTHER PUBLICATIONS

European Search Report for European Application No. 20868541.2, Date of Mailing Sep. 18, 2023, 6 pages.
International Search Report issued in Application No. PCT/US2020/052096 on Dec. 17, 2020, 3 pages.
Written Opinion issued in Application No. PCT/US2020/052096 on Dec. 17, 2020, 5 pages.

* cited by examiner

*Primary Examiner* — Jeffrey H Murray
*Assistant Examiner* — Rilla Marie Samsell
(74) *Attorney, Agent, or Firm* — CANTOR COLBURN LLP

(57) ABSTRACT

Methods of treating EGFR mutant-related cancers with a combination of an EGFR inhibitor of Formula (I) and the CDK4/6 inhibitor of Formula (II) and use of combinations of these compounds in the manufacture of medicaments for the treatment of EGFR mutant-related cancers are disclosed:

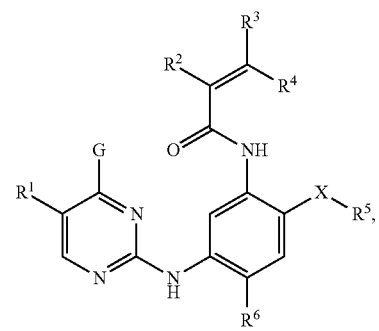

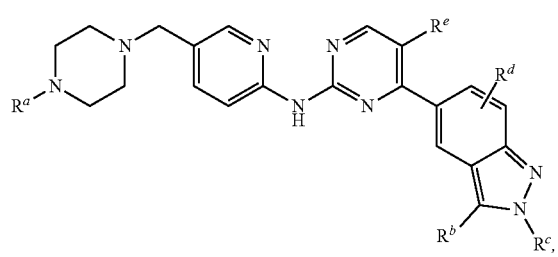

20 Claims, 2 Drawing Sheets

TREATMENT OF EGFR MUTANT-RELATED CANCERS USING A COMBINATION OF EGFR AND CDK4/6 INHIBITORS

CROSS-REFERENCE TO RELATED APPLICATIONS

This application is a § 371 U.S. National Stage application of International Application Ser. No. PCT/US2020/052096, filed Sep. 23, 2020, which claims the benefit of U.S. Provisional Application Ser. No. 62/904,567, filed Sep. 23, 2019, both of which are incorporated by reference in their entirety herein.

FIELD OF THE INVENTION

The invention is related to the field of treatments of epidermal growth factor receptor (EGFR) mutant-related cancers.

BACKGROUND OF THE INVENTION

The epidermal growth factor receptor (EGFR, Her1, ErbB1) is a principal member of the ErbB family of four structurally-related cell surface receptors with the other members being Her2 (Neu, ErbB2), Her3 (ErbB3) and Her4 (ErbB4). EGFR exerts its primary cellular functions though its intrinsic catalytic tyrosine protein kinase activity. The receptor is activated by binding with growth factor ligands, such as epidermal growth factor (EGF) and transforming growth factor-alpha (TGF-α), which transform the catalytically inactive EGFR monomer into catalytically active homo- and hetero-dimers. These catalytically active dimers then initiate intracellular tyrosine kinase activity, which leads to the autophosphorylation of specific EGFR tyrosine residues and elicits the downstream activation of signaling proteins. Subsequently, the signaling proteins initiate multiple signal transduction cascades (MAPK, Akt and JNK), which ultimately mediate the essential biological processes of cell growth, proliferation, motility and survival.

EGFR is found at abnormally high levels on the surface of many types of cancer cells and increased levels of EGFR have been associated with advanced disease, cancer spread and poor clinical prognosis. Mutations in EGFR can lead to receptor overexpression, perpetual activation or sustained hyperactivity and result in uncontrolled cell growth, i.e. cancer. Consequently, EGFR mutations have been identified in several types of malignant tumors, including metastatic lung, head and neck, bladder, breast, cervical, uterine, ovarian, squamous cell, gliomas, glioblastomas, colorectal, gastroesophageal, thyroid and pancreatic cancers. In human non-small cell lung cancer (NSCLC), mutations mainly occur in exons 18 to 21, which encode the adenosine triphosphate (ATP)-binding pocket of the kinase domain. The most clinically relevant drug-sensitive EGFR mutations are deletions in exon 19 that eliminate a common amino acid motif (LREA) and point mutations in exon 21, which lead to a substitution of arginine for leucine at position 858 (L858R). Together, these two activating mutations account for nearly 85% of the EGFR mutations observed in lung cancer. Both mutations have perpetual tyrosine kinase activity and as a result they are oncogenic.

In at least 50% of patients who are initially responsive to current therapy, disease progression is associated with the development of a secondary mutation, T790M in exon 20 of EGFR (sometimes referred to as the gatekeeper mutation). Unfortunately, inhibitors of EGFR are known to cause various undesired toxicities, especially at higher doses. In addition, acquired resistance to existing EGFR tyrosine kinase inhibitors remains a major challenge, especially for NSCLC.

Cyclin-dependent kinases are a family of protein kinases that regulate cell division and proliferation. Cell cycle progression is controlled by cyclins and their associated cyclin-dependent kinases, such as CDK1-CDK4 and CDK6, while other CDKs such as CDK7-CDK9 are critical to transcription. CDK binding to cyclins forms heterodimeric complexes that phosphorylate their substrates on serine and threonine residues, which in turn initiates events required for cell-cycle transcription and progression (Malumbres et al. *Trends Biochem. Sci.* 2005, 30, 630-641). Since uncontrolled cell proliferation is a hallmark of cancer, and most cancer cells exhibit deregulation of CDKs, inhibition of CDKs has emerged as a potential treatment for various cancers. Inhibitors with varying degrees of selectivity for CDKs have been reported. Inhibitors that are selective for CDK4 and CDK6 are a promising class of potential anticancer drugs because of their critical role in regulating cell proliferation and the increased toxic effects associated with the inhibition of the other CDKs.

It has been reported that the adverse effects of EGFR inhibitors can be attenuated to some extent through minimizing their dose levels, e.g., by enhancing the sensitivity of lung cancer cells, including resistant forms, through combination dosing with a selective cyclin-dependent dependent kinase inhibitor (Liu, M., et al., *Oncotarget* 2016, 7(51), 84951). However, development of new lower dosage treatment regimens for various EGFR mutant-related cancers that elicit improved efficacy, particularly against resistant forms, and cause fewer side effects is still in high demand.

SUMMARY OF THE INVENTION

The present invention meets the foregoing demand, based on a surprising discovery that Compound 1, a third-generation irreversible EGFR tyrosine kinase inhibitor that effectively inhibits the kinase domain of the T790M double mutant in addition to the activating mutations (see WO2016094821 A2), can be used in combination with Compound 2, preferably in synergistically effective amounts, a selective CDK4/6 inhibitor that has shown potent in vitro activity in an MCF7 human breast cancer cell line (see WO2016014904 A1), for treatment of human non-small cell lung cancer.

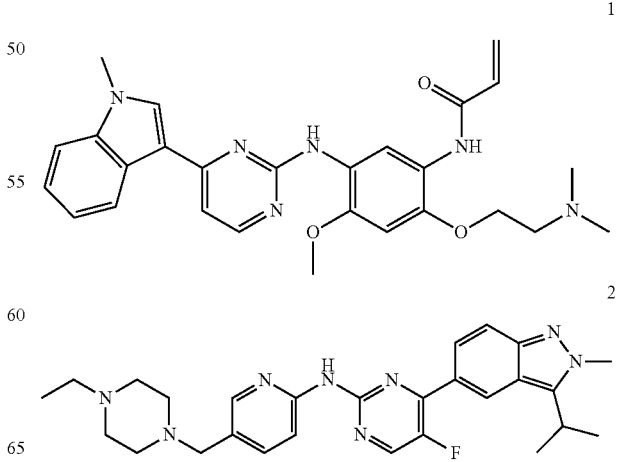

Because compound 1 overcomes the resistance observed with the currently used first and second generation reversible EGFR tyrosine kinase inhibitors, the new combination regimen should find broad application in the treatment of EGFR mutant related cancers, for example, lung cancer (especially non-small cell lung cancer), breast cancer, bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, and/or thyroid cancer. In particular, because of the superior brain-blood barrier (BBB) penetrability of these compounds, their combinations have a great potential in the treatment of metastatic brain cancer, especially those originated from EGFR mutant-related cancers, in particular, non-small cell lung cancer.

Thus, in one aspect, the present invention provides a method of treating a cancer associated with a mutant of epidermal growth factor receptor (EGFR) in a subject, the method comprising administering to the subject a therapeutically effective amount of an EGFR inhibitor of formula (I), or a pharmaceutically acceptable salt, solvate, or prodrug thereof, in combination with, preferably in a synergistically effective amount of, a cyclin-dependent kinase (CDK) inhibitor of formula (II), or a pharmaceutically acceptable salt, solvate, or prodrug thereof:

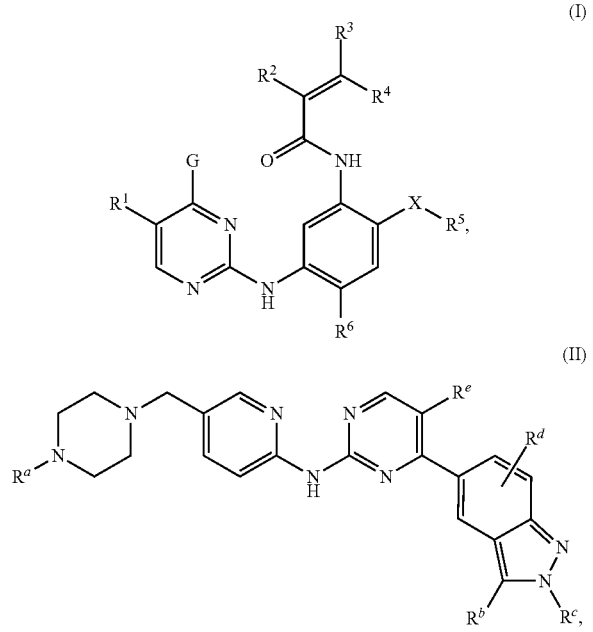

wherein in formula (I):

G is selected from substituted or unsubstituted 1H-indol-3-yl, substituted or unsubstituted 1H-indazol-3-yl, substituted or unsubstituted 2H-indazol-3-yl, and substituted or unsubstituted pyrazolo[1,5-α]-pyridin-3-yl, and substituted or unsubstituted 4,5,6,7-tetrahydropyrazolo[1,5-α]pyridin-3-yl;

X is selected from oxygen, sulfur, and methylene;

$R^1$ is selected from hydrogen, halogen, methyl, trifluoromethyl, and cyano;

$R^2$, $R^3$, and $R^4$ are the same or different and are independently selected from hydrogen, halogen, and trifluoromethyl;

$R^5$ is selected from lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are independently selected from hydrogen and lower alkyl; and $R^6$ is selected from lower alkoxy and lower alkyl;

and wherein in formula (II):

$R^a$ is hydrogen, $C_1$-$C_8$ alkyl, or $C_3$-$C_7$ cycloalkyl, or a metabolizable group that can be removed under physiological conditions to form the corresponding unsubstituted compound;

$R^b$ and $R^c$ are each independently hydrogen, $C_1$-$C_8$ alkyl, $C_3$-$C_7$ cycloalkyl, or $C_3$-$C_7$ cycloalkylmethyl;

$R^d$ is hydrogen, halogen, $C_1$-$C_8$ alkyl, or $C_3$-$C_7$ cycloalkyl; and $R^e$ is hydrogen or halogen.

In one embodiment, the present invention relates to a method of treatment for NSCLC employing a combination of the EGFR tyrosine kinase inhibitor N-[2-[2-(dimethylamino)ethoxy]-4-methoxy-5-[[4-(1-methyl-1H-indol-3-yl)-2-pyrimidinyl]amino]phenyl]-2-propenamide (1) and the selective CDK4/6 inhibitor N-[5-[(4-ethyl-1-piperazinyl)methyl]-2-pyridinyl]-5-fluoro-4-[2-methyl-3-(1-methylethyl)-2H-indazol-5-yl]-2-pyrimidinamine (2). The combination therapy of 1 and 2 surprisingly results in synergistic efficacy, thereby minimizing the dose of each compound and offering the potential to reduce adverse side effects.

In one embodiment, the invention is directed to a method of treating a human subject having non-small cell lung carcinoma harboring an EGFR mutation, the method comprising the step of administering an effective amount of the EGFR tyrosine kinase inhibitor of Formula 1, or a pharmaceutically acceptable salt thereof, in combination with a synergistically effective amount of the CDK4/6 inhibitor of Formula 2, or a pharmaceutically acceptable salt thereof. The non-small cell lung carcinoma can harbor the EGFR T790M resistance mutation. The salt form of the inhibitor of Formula 1 can be a methanesulfonate, and the salt form for the inhibitor of Formula 2 can be a hydrochloride.

In another embodiment, the invention is directed to a method of treating a human subject having an EGFR-mutant cancer that has developed an acquired resistance to an epidermal growth factor receptor tyrosine kinase inhibitor (EGFR-TKI) treatment, the method comprising the step of administering to the human subject an effective amount of the EGFR tyrosine kinase inhibitor of Formula 1, or a pharmaceutically acceptable salt thereof, in combination with a synergistically effective amount of the CDK4/6 inhibitor of Formula 2, or a pharmaceutically acceptable salt thereof. The EGFR-mutant cancer can be breast cancer. The breast cancer can be estrogen receptor-positive breast cancer, progesterone receptor-positive breast cancer, or HER2-positive breast cancer. The EGFR-mutant cancer can be bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, or thyroid cancer.

In another embodiment, the invention is directed to a method of treating a human subject having an EGFR-mutant cancer, wherein the subject is EGFR-TKI-treatment naive, the method comprising the step of administering to the human subject an effective amount of the EGFR tyrosine kinase inhibitor of Formula 1, or a pharmaceutically acceptable salt thereof, with a synergistically effective amount of the CDK4/6 inhibitor of Formula 2 or a pharmaceutically acceptable salt thereof.

In another aspect, the present invention relates to use of any combinations of compounds of formula (I) and compounds of formula (II), preferably in synergistically effective amounts, in the manufacture of a medicament for the treatment of an EGFR-mutant related cancer as disclosed herein.

Other aspects and benefits of the present invention will be better appreciated in view of the following detailed description, drawings, and claims.

DETAILED DESCRIPTION OF THE INVENTION

Figure 1:
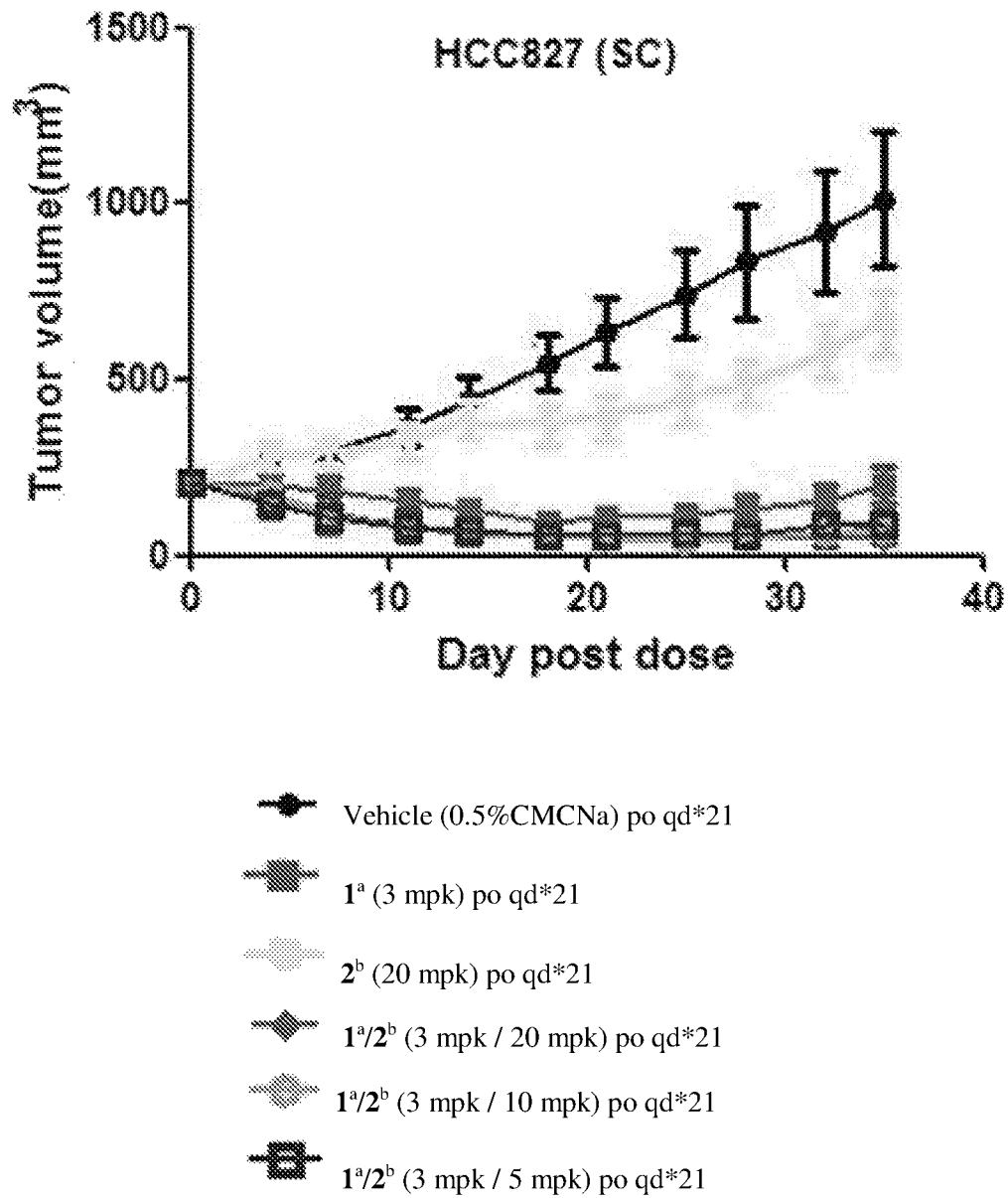
FIG. 1 illustrates a graph of the anti-tumor effects of EGFR tyrosine kinase inhibitor 1, CDK4/6 inhibitor 2 and their combinations in a HCC827 mouse xenograft tumor model (mean±SD, n=8).

In one aspect, the present invention provides a method of treating a cancer associated with a mutant of epidermal growth factor receptor (EGFR) in a subject, the method comprising administering to the subject a therapeutically effective amount of an EGFR inhibitor of formula (I), or a pharmaceutically acceptable salt, solvate, or prodrug thereof, in combination with a cyclin-dependent kinase (CDK) inhibitor of formula (II), or a pharmaceutically acceptable salt, solvate, or prodrug thereof, preferably in synergistically effective amounts:

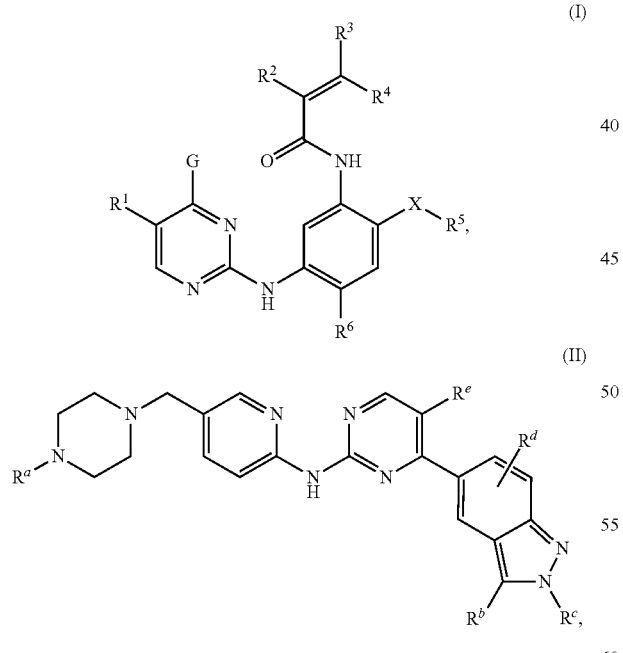

wherein in formula (I):
G is selected from substituted or unsubstituted 1H-indol-3-yl, substituted or unsubstituted 1H-indazol-3-yl, substituted or unsubstituted 2H-indazol-3-yl, and substituted or unsubstituted pyrazolo[1,5-α]-pyridin-3-yl, and substituted or unsubstituted 4,5,6,7-tetrahydropyrazolo[1,5-α]pyridin-3-yl;

X is selected from oxygen, sulfur, and methylene;
$R^1$ is selected from hydrogen, halogen, methyl, trifluoromethyl, and cyano;
$R^2$, $R^3$, and $R^4$ are the same or different and are independently selected from hydrogen, halogen, and trifluoromethyl;
$R^5$ is selected from lower alkyl, optionally substituted 3- to 6-membered heterocyclyl, $R^7R^8N$-(lower alkyl), and $R^7R^8N$-(cycloalkylalkyl), wherein $R^7$ and $R^8$ are the same or different and are independently selected from hydrogen and lower alkyl; and
$R^6$ is selected from lower alkoxy and lower alkyl;
and wherein in formula (II):
$R^a$ is hydrogen, $C_1$-$C_8$ alkyl, or $C_3$-$C_7$ cycloalkyl, or a metabolizable group that can be removed under physiological conditions to form the corresponding unsubstituted compound;
$R^b$ and $R^c$ are each independently hydrogen, $C_1$-$C_8$ alkyl, $C_3$-$C_7$ cycloalkyl, or $C_3$-$C_7$ cycloalkylmethyl;
$R^d$ is hydrogen, halogen, $C_1$-$C_8$ alkyl, or $C_3$-$C_7$ cycloalkyl; and
$R^e$ is hydrogen or halogen.

In one embodiment, sometimes preferred, in formula (II), $R^a$ is hydrogen.

In one embodiment, sometimes preferred, in formula (II), $R^a$ is $C_1$-$C_6$ alkyl.

In one embodiment, sometimes preferred, in formula (II), $R^a$ is methyl, ethyl, propyl, or isopropyl.

The phrase "a metabolizable group that can be removed under physiological conditions to form the corresponding unsubstituted compound," as used herein, refers to those groups that are hydrolysable under physiological conditions. In some embodiments, the metabolizable group is RC(O)—, wherein R includes, but is not limited to, H, methyl, ethyl, propyl, isopropyl, or the like, preferably, methyl or ethyl, and more preferably methyl. In some embodiments, the metabolizable group is ROC(O)—, wherein R includes, but is not limited to, methyl, ethyl, propyl, isopropyl, cyclopropyl, or the like, preferably methyl or ethyl, and more preferably methyl.

In one embodiment, sometimes preferred, in formula (II), $R^b$ is $C_1$-$C_6$ alkyl, $C_3$-$C_6$ cycloalkyl, or $C_3$-$C_6$ cycloalkylmethyl.

In one embodiment, sometimes preferred, in formula (II), $R^b$ is methyl, ethyl, propyl, isopropyl, cyclopropyl, cyclopentyl, cyclopropylmethyl, or cyclopentylmethyl.

In one embodiment, sometimes preferred, in formula (II), $R^c$ is $C_1$-$C_6$ alkyl or $C_3$-$C_6$ cycloalkyl.

In one embodiment, sometimes preferred, in formula (II), $R^c$ is methyl, ethyl, propyl, isopropyl, or cyclopropyl.

In one embodiment, sometimes preferred, in formula (II), $R^d$ is located at the 7-position of the indazole ring, characterized by formula IIa:

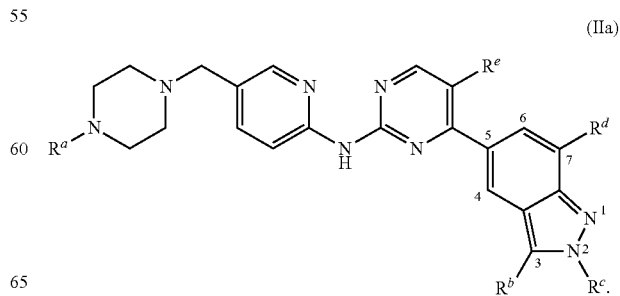

In one embodiment, sometimes preferred, in formula (II), $R^d$ is hydrogen or halogen.

In one embodiment, sometimes preferred, in formula (II), $R^e$ is hydrogen or fluoro.

In one embodiment, sometimes preferred, in formula (II), $R^a$ is methyl or ethyl; $R^b$ is isopropyl, cyclopropyl, cyclopropylmethyl, or cyclopentyl; $R^3$ is methyl or ethyl; $R^4$ is hydrogen or fluoro; and $R^5$ is hydrogen or fluoro.

In one embodiment, sometimes preferred, in formula (II), the compound of formula (II) is selected from the group consisting of:

(Ic)

(Id)

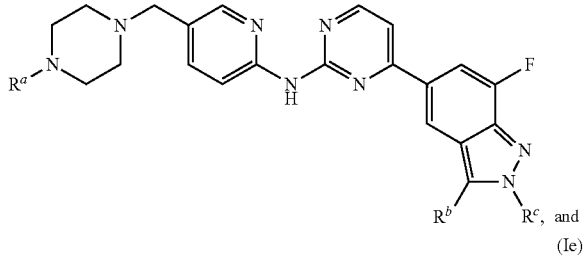

(Ie)

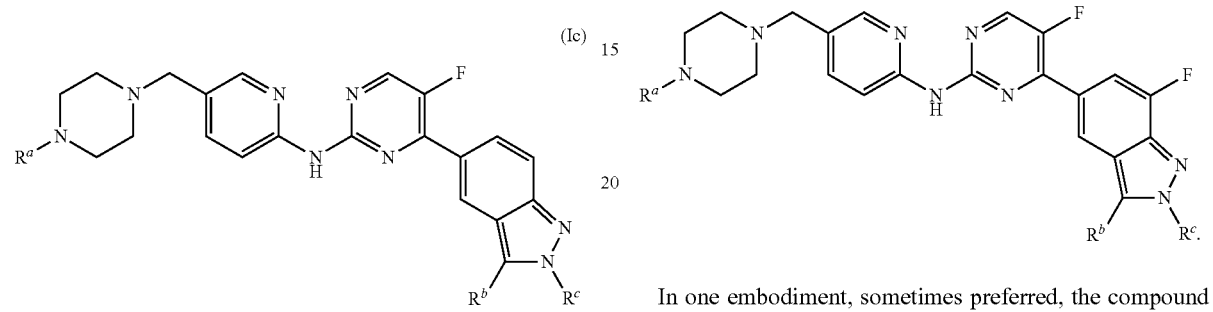

In one embodiment, sometimes preferred, the compound of formula (II) is selected from the list of Table 1.

TABLE 1

Selected examples of the compounds

| Example | Structure | Name |
| --- | --- | --- |
| II-1 (or 2) | 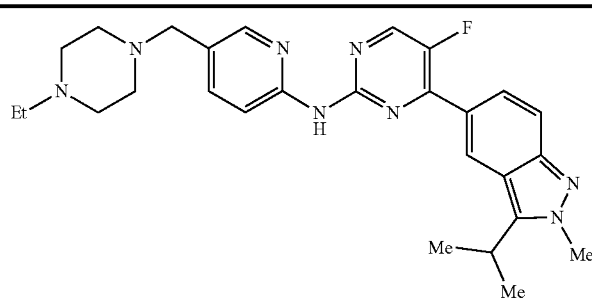 | N-(5-((4-ethylpiperazin-1-yl)methyl)pyridin-2-yl)-5-fluoro-4-(3-isopropyl-2-methyl-2H-indazol-5-yl)pyrimidin-2-amine |
| II-2 | 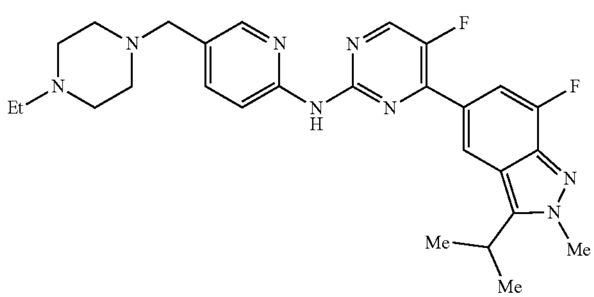 | N-(5-((4-ethylpiperazin-1-yl)methyl)pyridin-2-yl)-5-fluoro-4-(7-fluoro-3-isopropyl-2-methyl-2H-indazol-5-yl)pyrimidin-2-amine |
| II-3 | 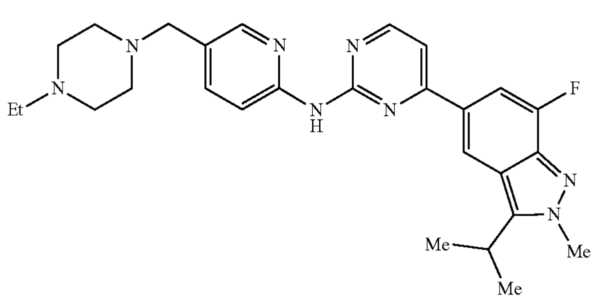 | N-(5-((4-ethylpiperazin-1-yl)methyl)pyridin-2-yl)-4-(7-fluoro-3-isopropyl-2-methyl-2H-indazol-5-yl)pyrimidin-2-amine |

TABLE 1-continued

Selected examples of the compounds

| Example | Structure | Name |
|---|---|---|
| II-4 | 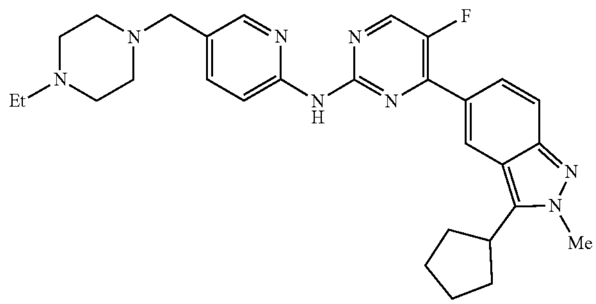 | 4-(3-cyclopentyl-2-methyl-2H-indazol-5-yl)-N-(5-((4-ethylpiperazin-1-yl)methyl)pyridin-2-yl)-5-fluoropyrimidin-2-amine |
| II-5 | 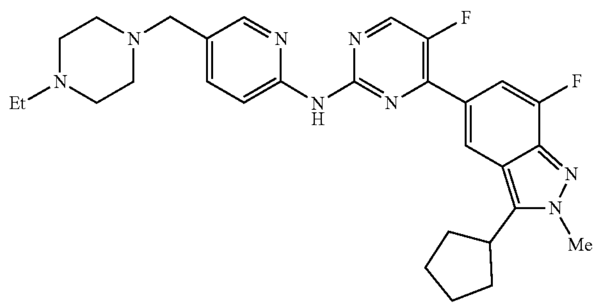 | 4-(3-cyclopentyl-7-fluoro-2-methyl-2H-indazol-5-yl)-N-(5-((4-ethylpiperazin-1-yl)methyl)pyridin-2-yl)-5-fluoropyrimidin-2-amine |
| II-6 | 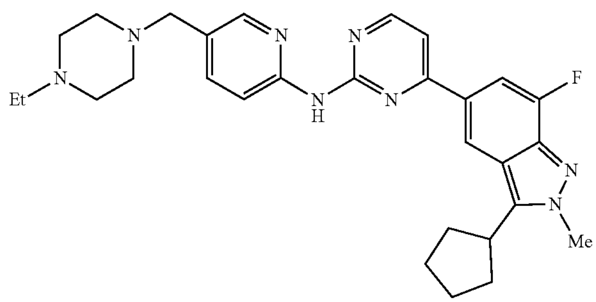 | 4-(3-cyclopentyl-7-fluoro-2-methyl-2H-indazol-5-yl)-N-(5-((4-ethylpiperazin-1-yl)methyl)pyridin-2-yl)pyrimidin-2-amine |
| II-7 | 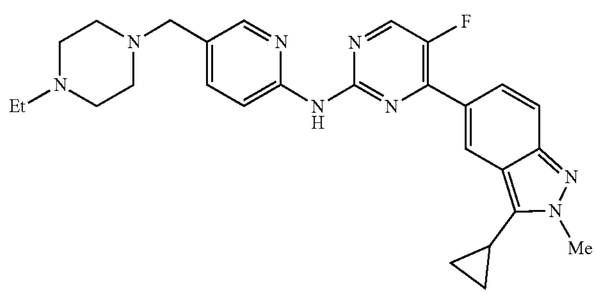 | 4-(3-cyclopropyl-2-methyl-2H-indazol-5-yl)-N-(5-((4-ethylpiperazin-1-yl)methyl)pyridin-2-yl)-5-fluoropyrimidin-2-amine |
| II-8 | 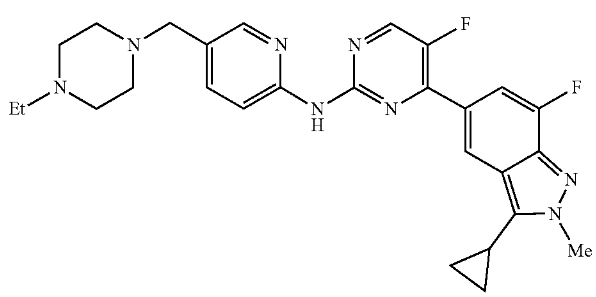 | 4-(3-cyclopropyl-7-fluoro-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---------|-----------|------|
| II-9 | 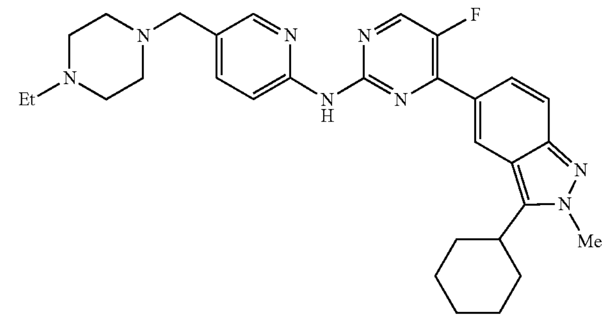 [SMILES: CCN1CCN(Cc2ccc(Nc3ncc(F)c(-c4ccc5nn(C)c(C6CCCCC6)c5c4)n3)nc2)CC1] | 4-(3-cyclohexyl-2-methyl-2H-indazol-5-yl)-N-(5-((4-ethylpiperazin-1-yl)methyl)pyridin-2-yl)-5-fluoropyrimidin-2-amine |
| II-10 | 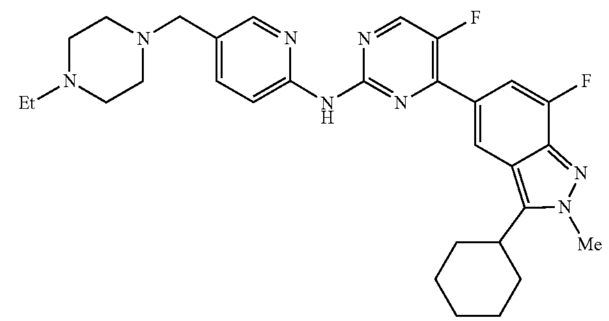 | 4-(3-cyclohexyl-7-fluoro-2-methyl-2H-indazol-5-yl)-N-(5-((4-ethylpiperazin-1-yl)methyl)pyridin-2-yl)-5-fluoropyrimidin-2-amine |
| II-11 | 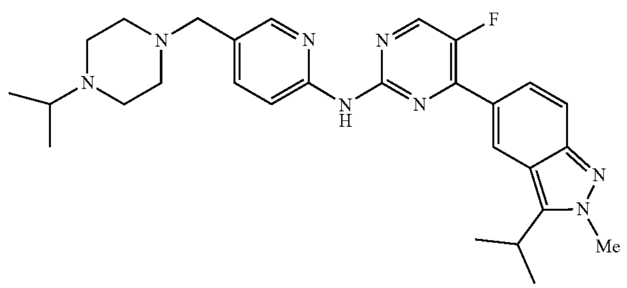 [SMILES: CC(C)c1c2cc(-c3nc(Nc4ccc(CN5CCN(C(C)C)CC5)cn4)ncc3F)ccc2nn1C] | 5-fluoro-4-(3-isopropyl-2-methyl-2H-indazol-5-yl)-N-(5-((4-isopropylpiperazin-1-yl)methyl)pyridin-2-yl)pyrimidin-2-amine |
| II-12 | 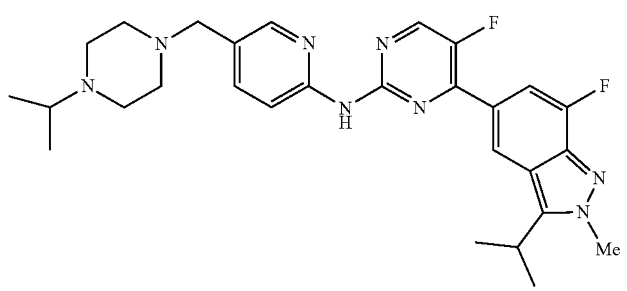 | 5-fluoro-4-(7-fluoro-3-isopropyl-2-methyl-2H-indazol-5-yl)-N-(5-((4-isopropylpiperazin-1-yl)methyl)pyridin-2-yl)pyrimidin-2-amine |
| II-13 | 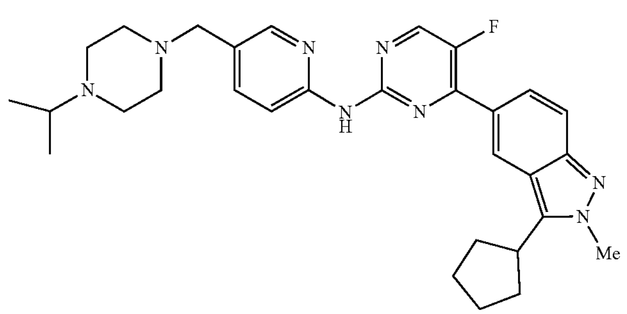 [SMILES: CC(C)N1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-isopropylpiperazin-1-yl)methyl)pyridin-2-yl)pyrimidin-2-amine |

TABLE 1-continued

Selected examples of the compounds

| Example | Structure | Name |
|---|---|---|
| II-14 | 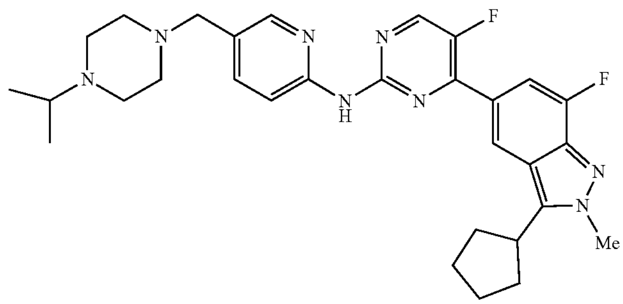 | 4-(3-cyclopentyl-7-fluoro-2-methyl-2H-indazol-5-yl)-5-fluoro-N-1-yl)methyl)pyridin-2-yl)pyrimidin-2-amine |
| II-15 | 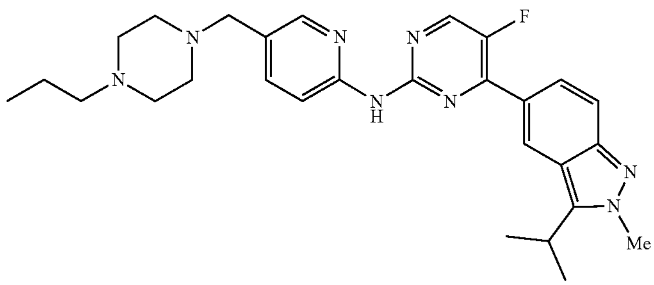 | 5-fluoro-4-(3-isopropyl-2-methyl-2H-indazol-5-yl)-N-(5-((4-propylpiperazin-1-yl)methyl)pyridin-2-yl)pyrimidin-2-amine |
| II-16 | 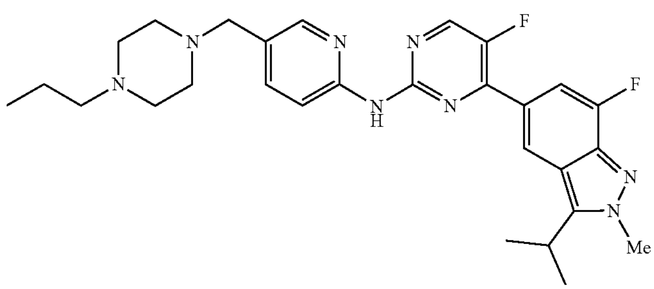 [SMILES: CCCN1CCN(Cc2ccc(Nc3ncc(F)c(-c4cc(F)c5nn(C)c(C(C)C)c5c4)n3)nc2)CC1] | 5-fluoro-4-(7-fluoro-3-isopropyl-2-methyl-2H-indazol-5-yl)-N-(5-((4-propylpiperazin-1-yl)methyl)pyridin-2-yl)pyrimidin-2-amine |
| II-17 | 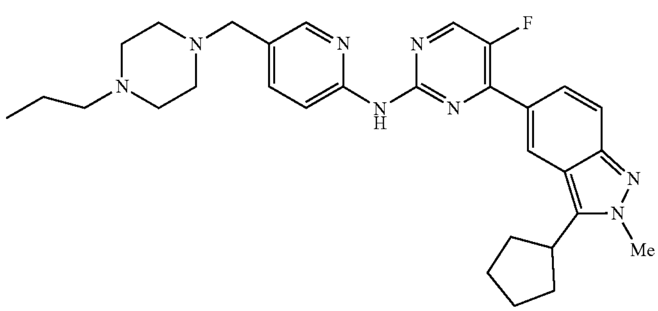 | 4-(3-cyclopentyl-2-methyl-2H-indazol-5-yl)-5-fluoro-N-(5-((4-propylpiperazin-1-yl)methyl)pyridin-2-yl)pyrimidin-2-amine |
| II-18 | 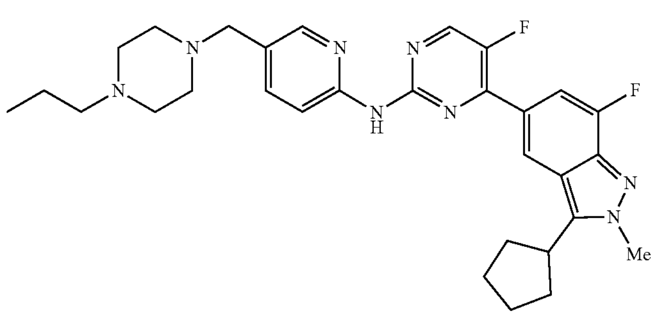 | 4-(3-cyclopentyl-7-fluoro-2-methyl-2H-indazol-5-yl)-5-fluoro-N-(5-((4-propylpiperazin-1-yl)methyl)pyridin-2-yl)pyrimidin-2-amine |

TABLE 1-continued

Selected examples of the compounds

| Example | Structure | Name |
|---|---|---|
| II-19 | 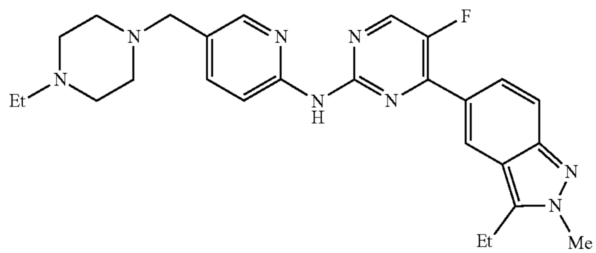 [SMILES: CCc1c2cc(-c3nc(Nc4ccc(CN5CCN(CC)CC5)cn4)ncc3F)ccc2nn1C] | 4-(3-ethyl-2-methyl-2H-indazol-5-yl)-N-(5-((4-ethylpiperazin-1-yl)methyl)pyridin-2-yl)-5-fluoropyrimidin-2-amine |
| II-20 | 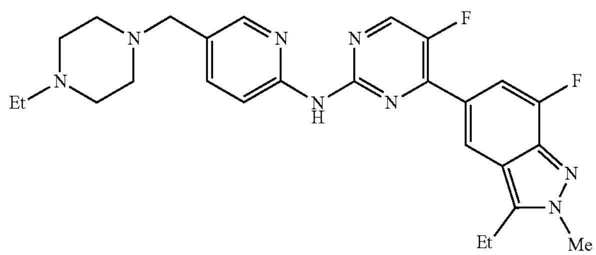 | 4-(3-ethyl-7-fluoro-2-methyl-2H-indazol-5-yl)-N-(5-((4-ethylpiperazin-1-yl)methyl)pyridin-2-yl)-5-fluoropyrimidin-2-amine |
| II-21 | 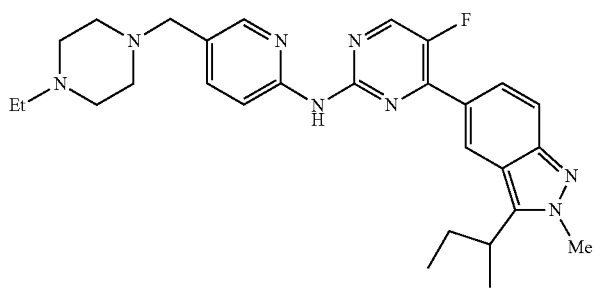 | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| II-22 | 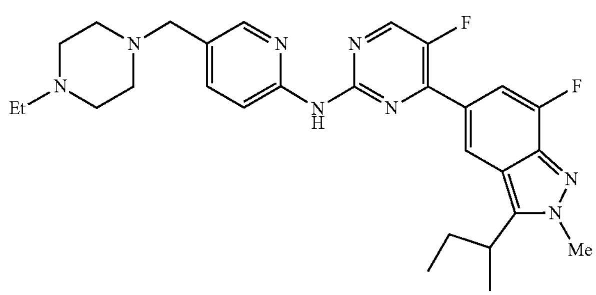 [SMILES: CCC(C)c1c2cc(-c3nc(Nc4ccc(CN5CCN(CC)CC5)cn4)ncc3F)cc(F)c2nn1C] | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |
| II-23 | 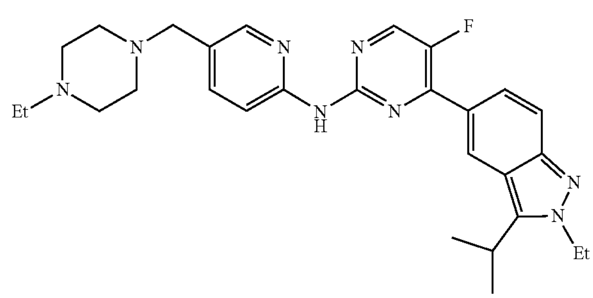 | 4-(2-ethyl-3-isopropyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---|---|---|
| II-24 | 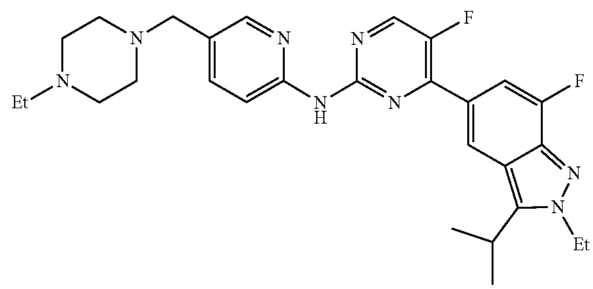 [SMILES: CCN1CCN(Cc2ccc(Nc3ncc(F)c(-c4cc(F)c5nn(CC)c(C(C)C)c5c4)n3)nc2)CC1] | 4-(2-ethyl-7-fluoro-3-isopropyl-2H-indazol-5-yl)-N-(5-((4-ethylpiperazin-1-yl)methyl)pyridin-2-yl)-5-fluoropyrimidin-2-amine |
| II-25 | 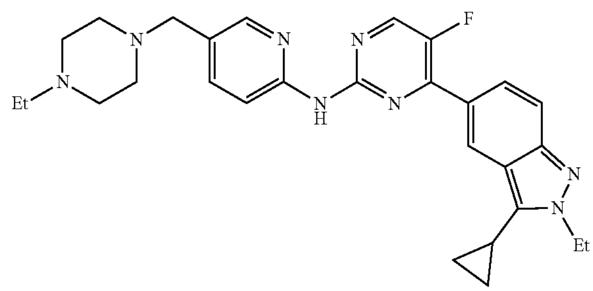 | 4-(3-cyclopropyl-2-ethyl-2H-indazol-5-yl)-N-(5-((4-ethylpiperazin-1-yl)methyl)pyridin-2-yl)-5-fluoropyrimidin-2-amine |
| II-26 | 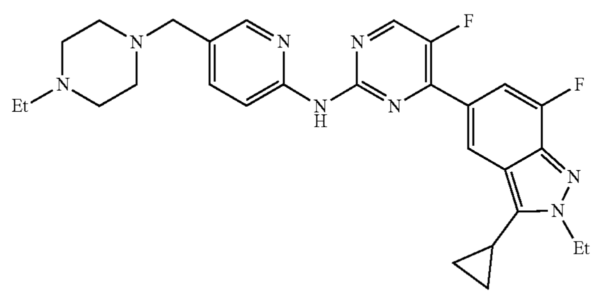 [SMILES: CCN1CCN(Cc2ccc(Nc3ncc(F)c(-c4cc(F)c5nn(CC)c(C6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)-5-fluoropyrimidin-2-amine |
| II-27 | 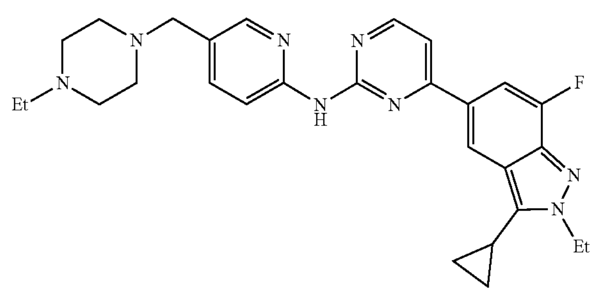 | 4-(3-(cyclopropylmethyl)-2-methyl-2H-indazol-5-yl)-N-(5-((4-ethylpiperazin-1-yl)methyl)pyridin-2-yl)-5-fluoropyrimidin-2-amine |
| II-28 | 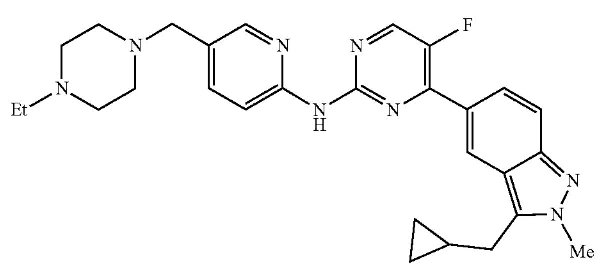 [SMILES: CCN1CCN(Cc2ccc(Nc3ncc(F)c(-c4ccc5nn(C)c(CC6CC6)c5c4)n3)nc2)CC1] | 4-(3-(cyclopropylmethyl)-7-fluoro-2-methyl-2H-indazol-5-yl)-N-(5-((4-ethylpiperazin-1-yl)methyl)pyridin-2-yl)-5-fluoropyrimidin-2-amine |

TABLE 1-continued

Selected examples of the compounds

| Example | Structure | Name |
|---------|-----------|------|
| II-29 | 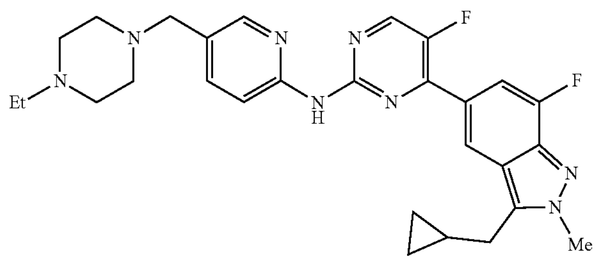 [SMILES: CCN1CCN(Cc2ccc(Nc3ncc(F)c(-c4cc(F)c5nn(C)c(CC6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)pyrimidin-2-amine |
| II-30 | 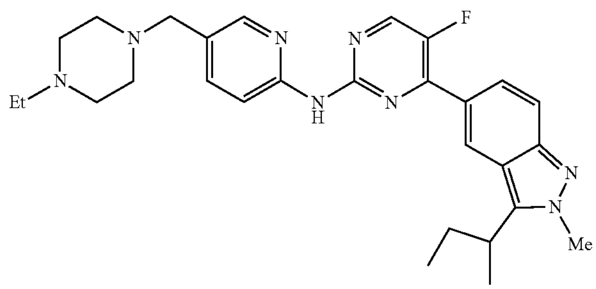 | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| II-31 | 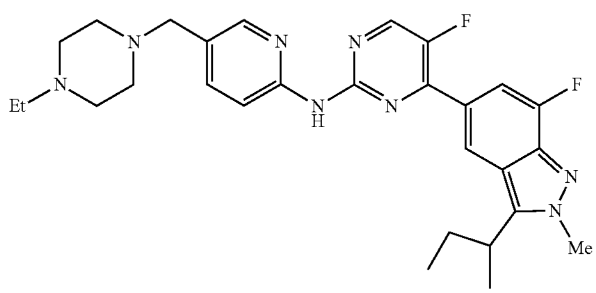 | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |
| II-32 | 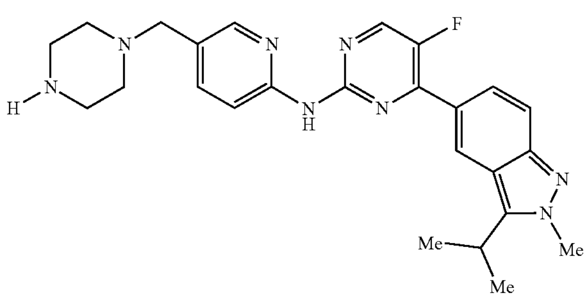 [SMILES: CC(C)c1c2cc(-c3nc(Nc4ccc(CN5CCNCC5)cn4)ncc3F)ccc2nn1C] | 5-fluoro-4-(3-isopropyl-2-methyl-2H-indazol-5-yl)-N-(5-(piperazin-1-ylmethyl)pyridin-2-yl)pyrimidin-2-amine |
| II-33 | 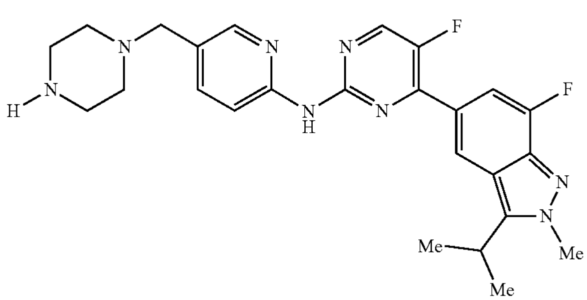 | 5-fluoro-4-(7-fluoro-3-isopropyl-2-methyl-2H-indazol-5-yl)-N-(5-(piperazin-1-ylmethyl)pyridin-2-yl)pyrimidin-2-amine |

TABLE 1-continued

Selected examples of the compounds

| Example | Structure | Name |
|---|---|---|
| II-34 | 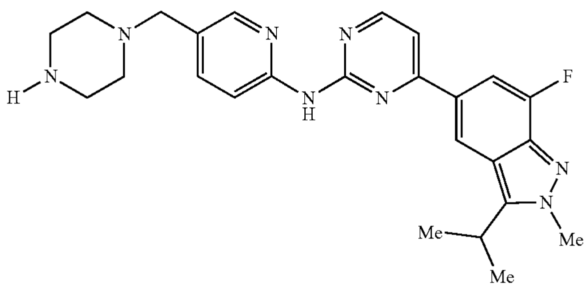 [SMILES: CC(C)c1c2cc(-c3ccnc(Nc4ccc(CN5CCNCC5)cn4)n3)cc(F)c2nn1C] | 4-(7-fluoro-3-isopropyl-2-methyl-2H-indazol-5-yl)-N-(5-(piperazin-1-ylmethyl)pyridin-2-yl)pyrimidin-2-amine |

Other examples of CDK4/6 inhibitors of formula (II) that may be used in the present invention include those disclosed in WO 2019/148161, which is hereby incorporated by reference in its entirety as if the whole text of the application were set forth herein.

In one embodiment, sometimes preferred, in formula (I):
G is selected from the group consisting of 1H-indol-3-yl, 1-methyl-1H-indol-3-yl, 1-(2-fluoroethyl)-1H-indol-3-yl, 1,2-dimethyl-1H-indol-3-yl, pyrazolo[1,5-α]-pyridin-3-yl, 4,5,6,7-tetrahydropyrazolo[1,5-α]pyridin-3-yl, 1-methyl-1H-indazol-3-yl, and 2-methyl-2H-indazol-3-yl.

In one embodiment, sometimes preferred, in formula (I):
$R^5$ is selected from $C_1$-$C_6$ alkyl, substituted or unsubstituted azetidinyl, substituted or unsubstituted pyrrolidinyl, substituted or unsubstituted piperidinyl, $R^7R^8N$—$(CH_2)_n$— (n=1 to 5), $R^7R^8N$—$(C_3$-$C_6$ cycloalkyl)-$(CH_2)_m$— (m=1 to 3), wherein $R^7$ and $R^8$ are the same or different and are independently selected from hydrogen and lower alkyl.

In one embodiment, sometimes preferred, in formula (I):
$R^5$ is selected from methyl, 1-(dimethylamino)-cyclopropylmethyl, 3-(dimethylamino)cyclobutyl, 1-methylazetidin-3-yl, (R)-1-methylpyrrolidin-3-yl, (S)-1-methylpyrrolidin-3-yl, and 1-methylpiperidin-4-yl, and 2-dimethylamino-ethyl.

In one embodiment, sometimes preferred, in formula (I), $R^1$ is hydrogen, halogen, or methyl.

In one embodiment, sometimes preferred, in formula (I), $R^1$ is hydrogen.

In one embodiment, sometimes preferred, in formula (I), $R^2$ is hydrogen or halogen.

In one embodiment, sometimes preferred, in formula (I), $R^4$ is hydrogen.

In one embodiment, sometimes preferred, in formula (I):
$R^2$ is hydrogen, F, or Cl;
$R^3$ is hydrogen, F, Cl, or —$CF_3$; and
$R^4$ is hydrogen.

In one embodiment, sometimes preferred, in formula (I), X is oxygen.

In one embodiment, sometimes preferred, in formula (I), X is sulfur.

In one embodiment, sometimes preferred, in formula (I), X is —$CH_2$—.

In one embodiment, sometimes preferred, the compound of formula (I) is a compound of formula (Ia):

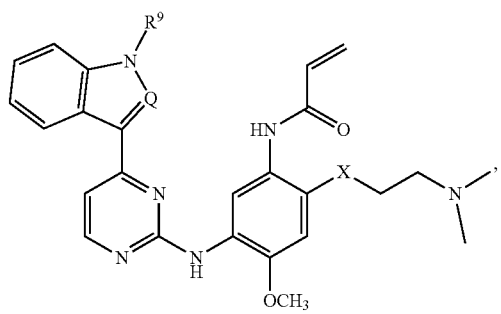

(Ia)

or a pharmaceutically acceptable salt, solvate, or prodrug thereof, wherein:
X is O, S, or $CH_2$;
Q is C—$R^{10}$ or N;
$R^9$ is $CH_3$ or $CH_2CH_2F$; and
$R^{19}$ is H or $CH_3$.

In one embodiment, sometimes preferred, in formula (Ia), Q is C—$R^{10}$.

In one embodiment, sometimes preferred, in formula (Ia), $R^9$ is $CH_3$.

In one embodiment, sometimes preferred, in formula (Ia), X is O.

In one embodiment, sometimes preferred, the compound of formula (Ia) has the following structure:

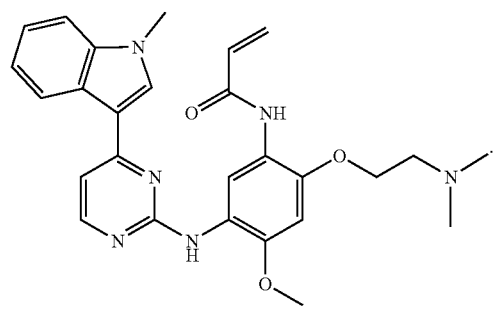

In one embodiment, sometimes preferred, the compound of formula (Ia) has the following structure:

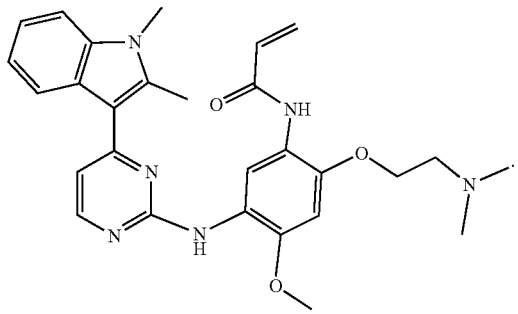

In one embodiment, sometimes preferred, in formula (Ia), X is S.

In one embodiment, sometimes preferred, the compound of formula (Ia) has the following structure:

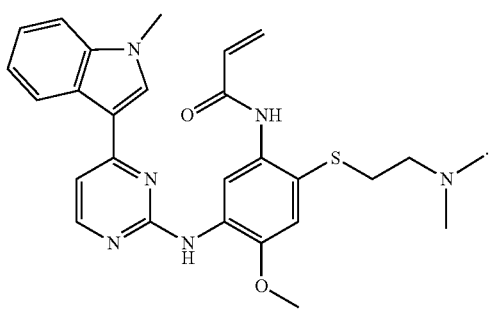

In one embodiment, sometimes preferred, in formula (Ia), X is $CH_2$.

In one embodiment, sometimes preferred, the compound of formula (Ia) has the following structure:

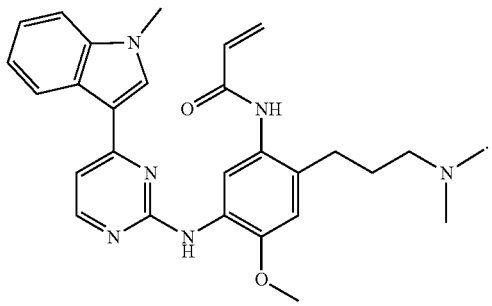

In one embodiment, sometimes preferred, in formula (Ia), $R^9$ is $CH_2CH_2F$.

In one embodiment, sometimes preferred, the compound of formula (Ia) has the following structure:

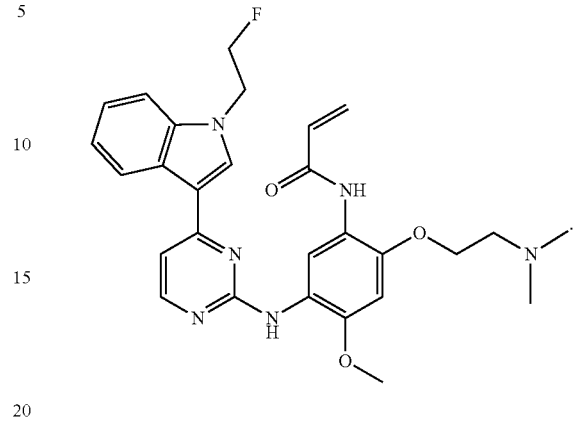

In one embodiment, sometimes preferred, in formula (Ia), Q is N.

In one embodiment, sometimes preferred, the compound of formula (Ia) has the following structure:

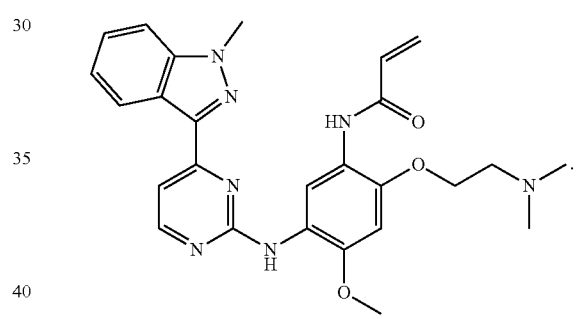

In one embodiment, sometimes preferred, the compound of formula (Ia) has the following structure:

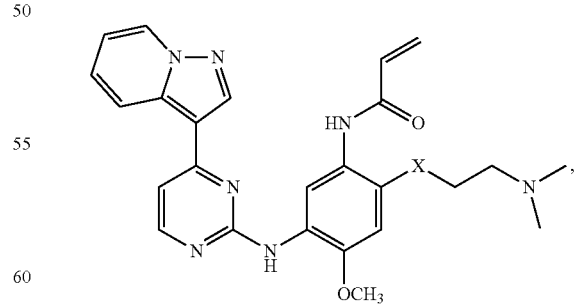

wherein X is O, S, or $CH_2$, and sometimes preferably X is O.

In one embodiment, sometimes preferred, the compound of formula (I) is selected from the group consisting of:
I-1 (or 1)
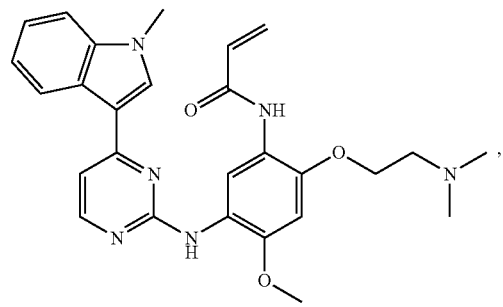
I-2
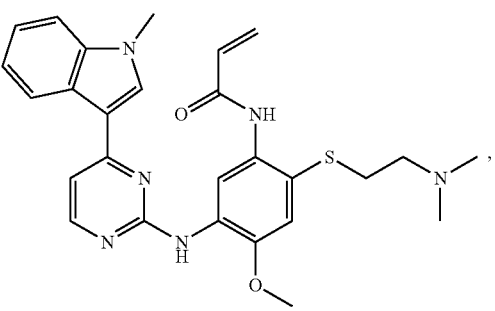
I-3
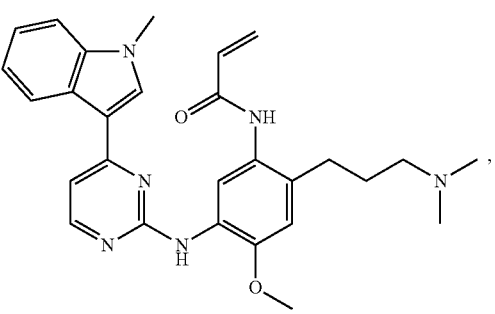
I-4
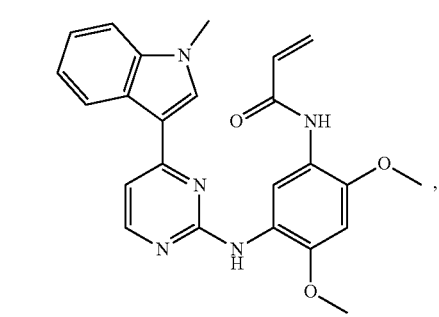
-continued
I-5
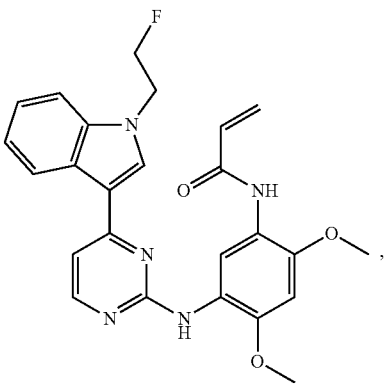
I-6
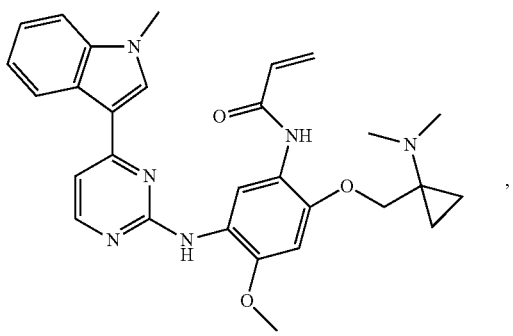
I-7
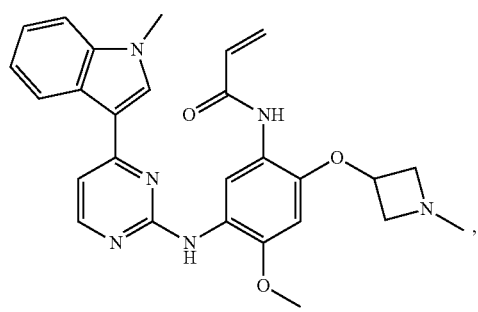
I-8
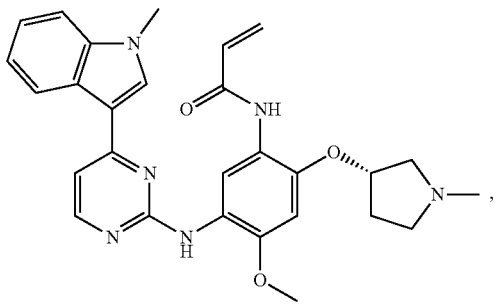
I-9
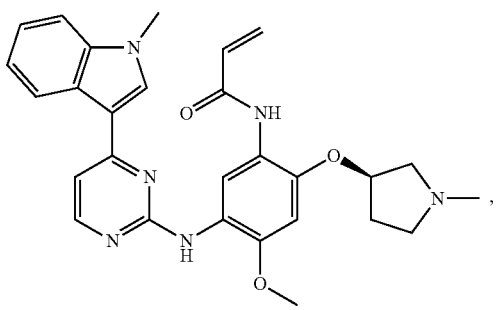

-continued
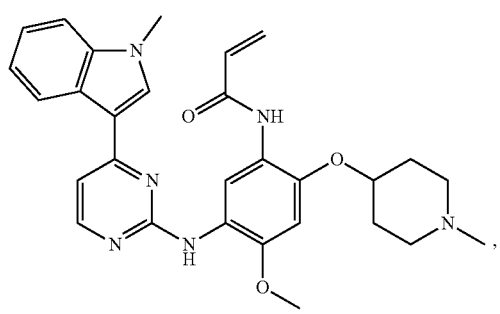
I-10
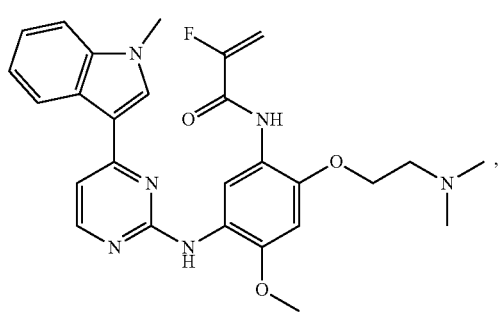
I-11
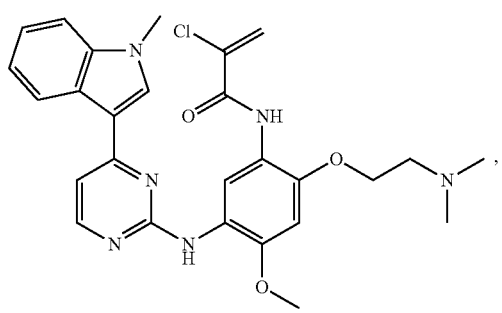
I-12
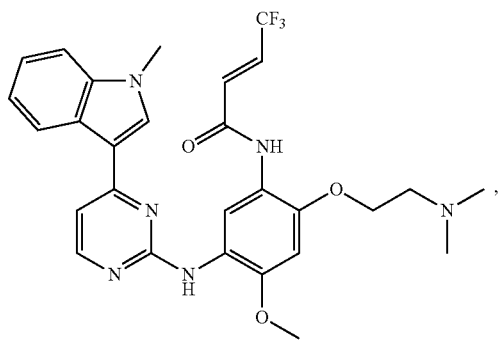
I-13
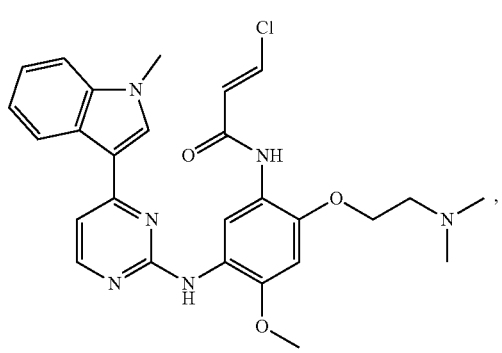
I-14
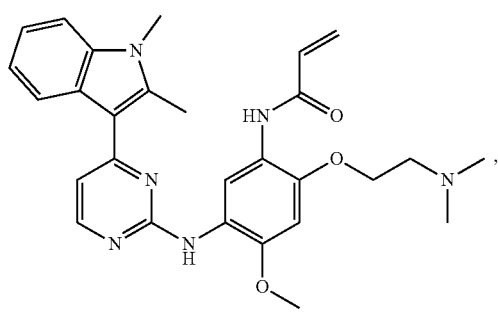
I-15
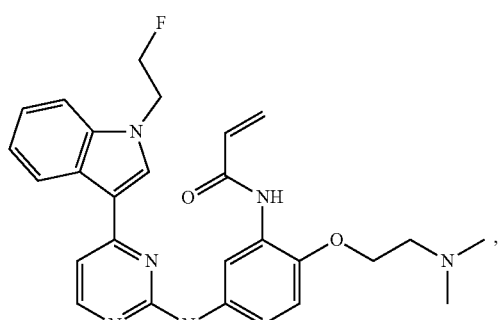
I-16
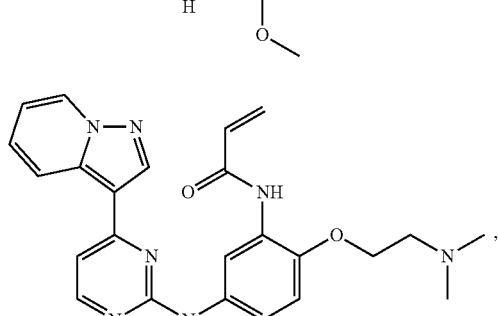
I-17
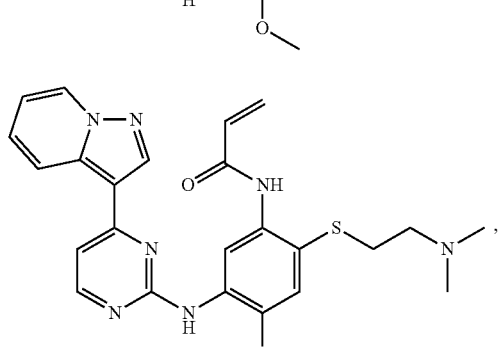
I-18
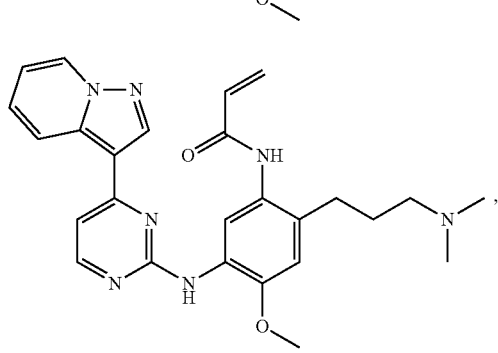
I-19

-continued
I-20
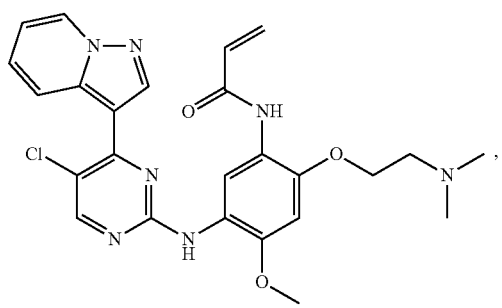
I-21
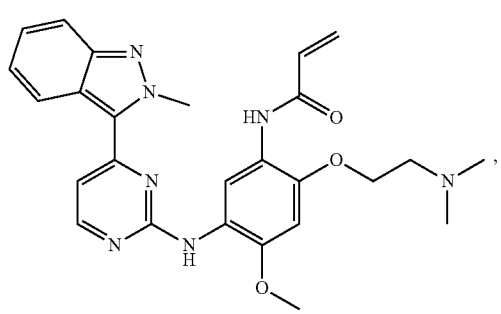
I-22
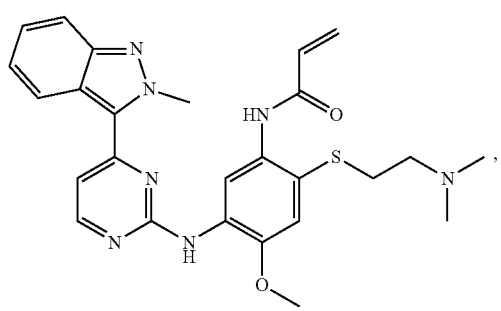
I-23
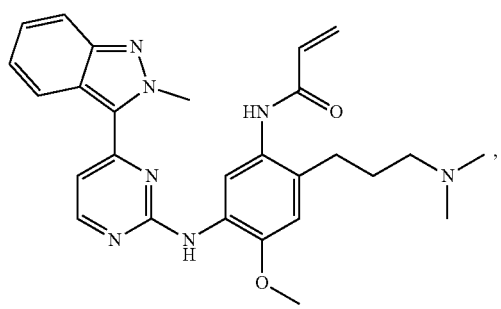
I-24
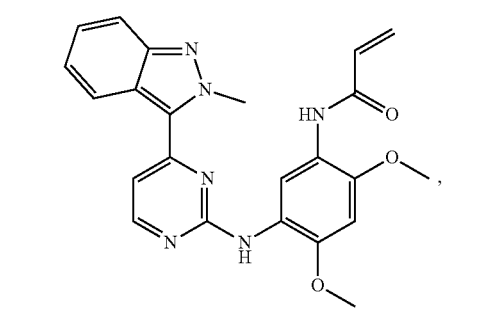
-continued
I-25
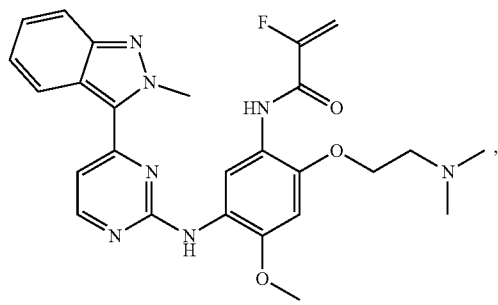
I-26
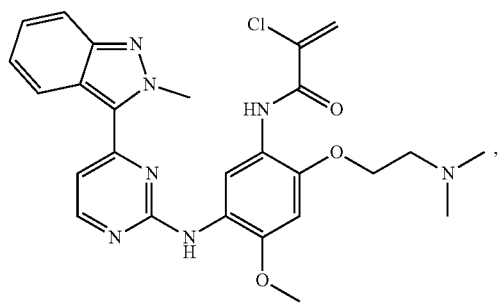
I-27
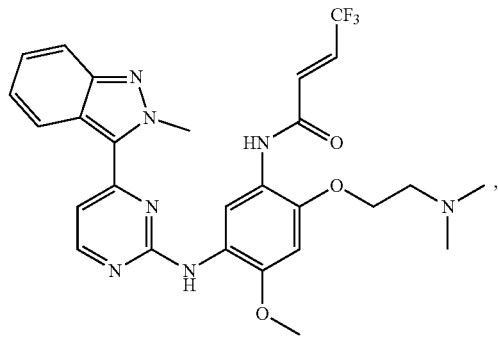
I-28
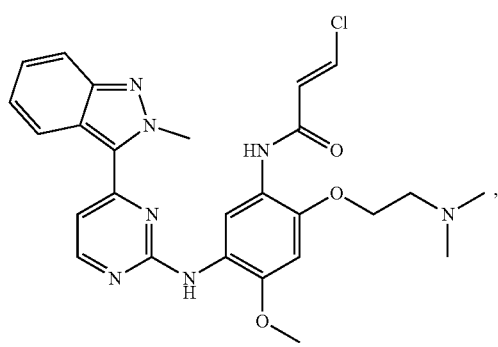
I-29
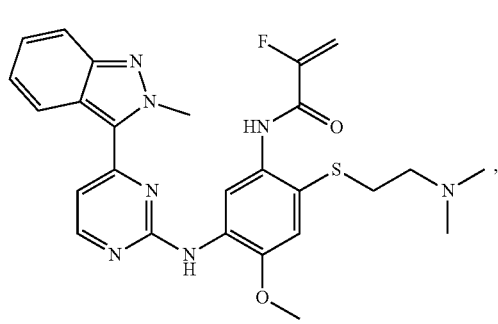

I-30
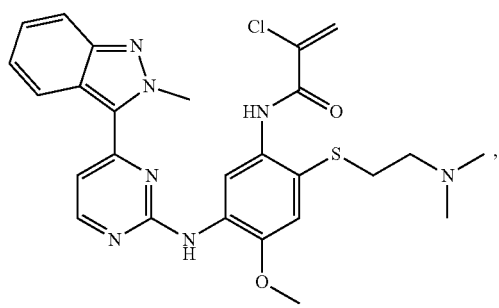
I-31
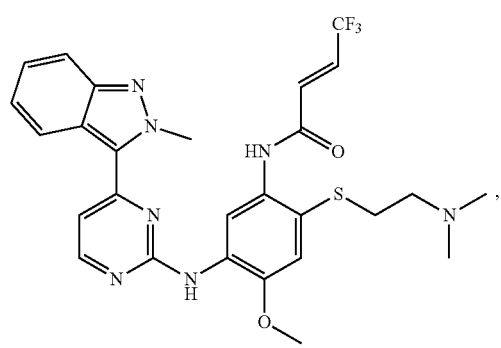
I-32
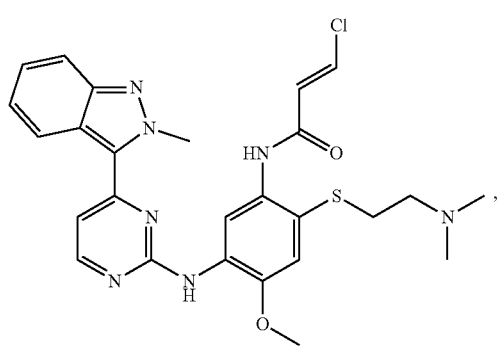
I-33
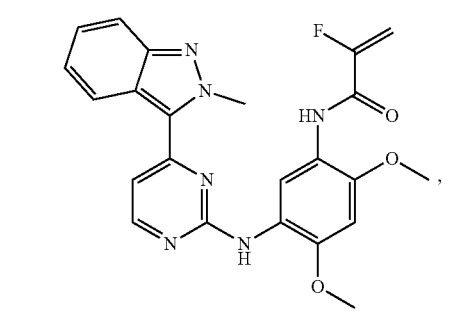
I-34
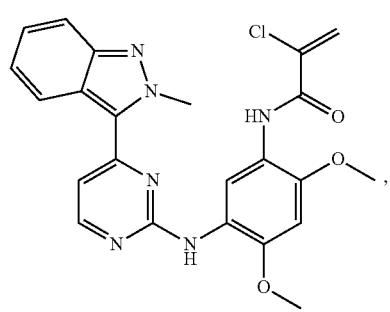
I-35
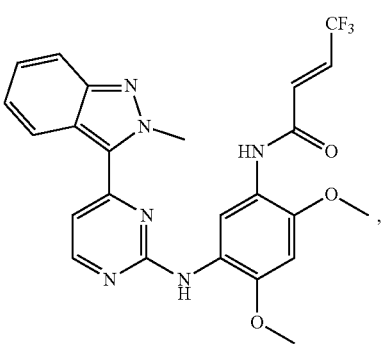
I-36
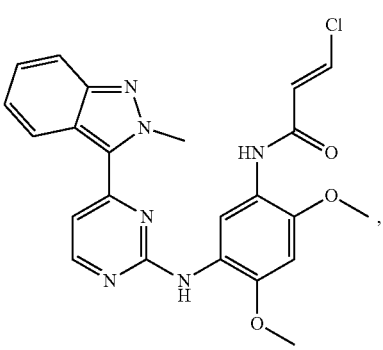
I-37
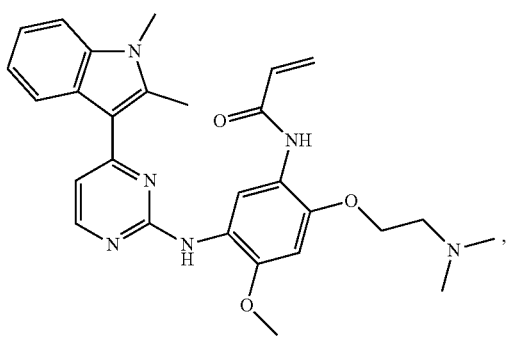
I-38
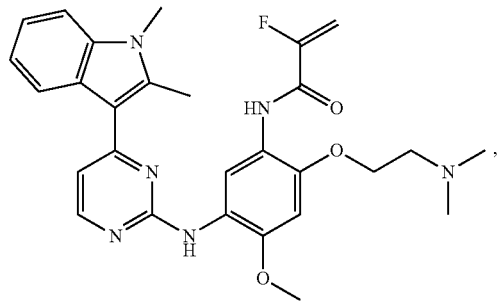
I-39
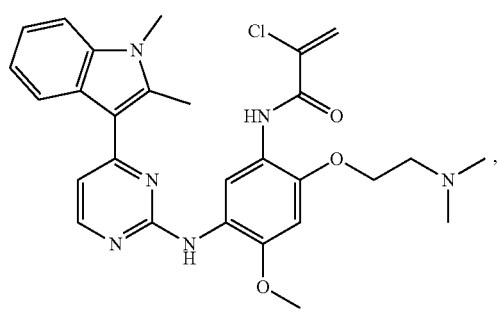

-continued
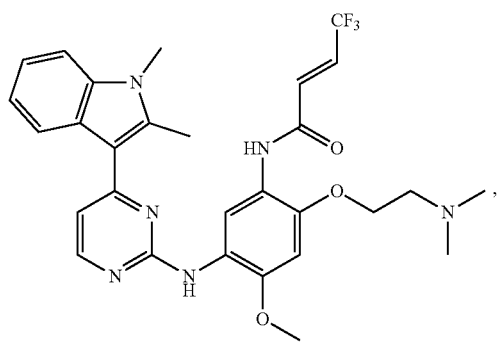
I-40
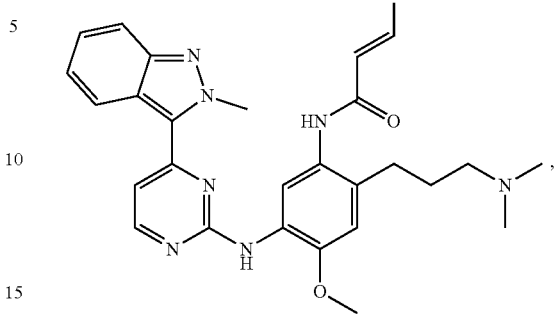
I-44
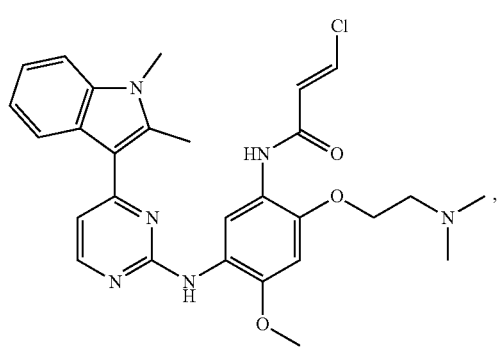
I-41
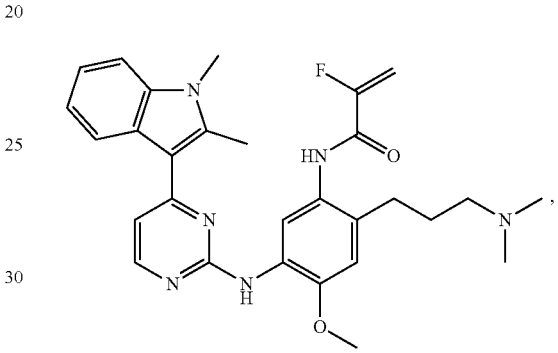
I-45
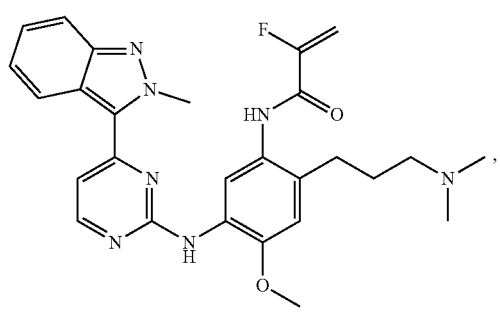
I-42
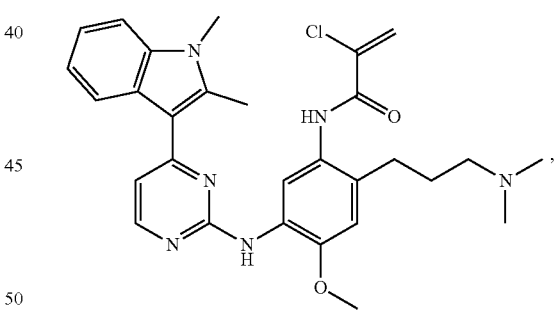
I-46
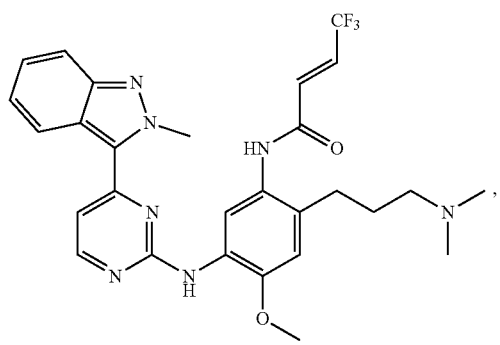
I-43
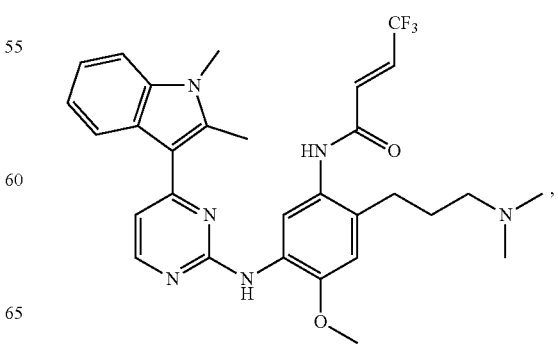
I-47

I-48
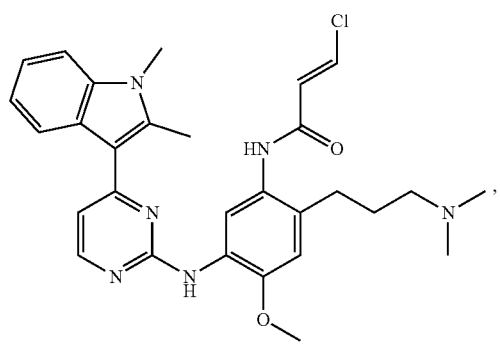
I-49
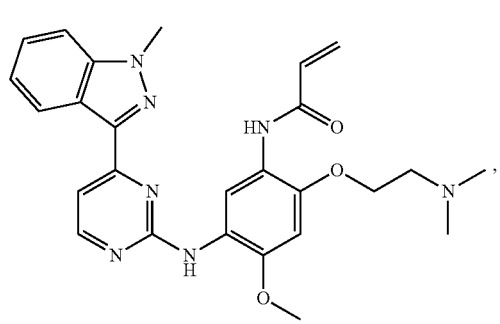
I-50
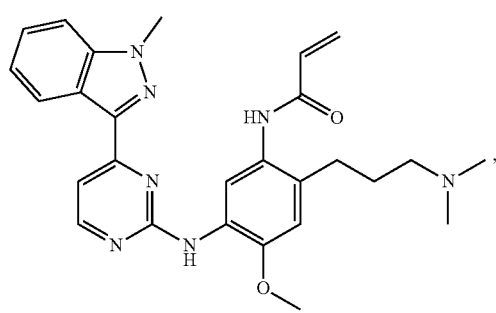
I-51
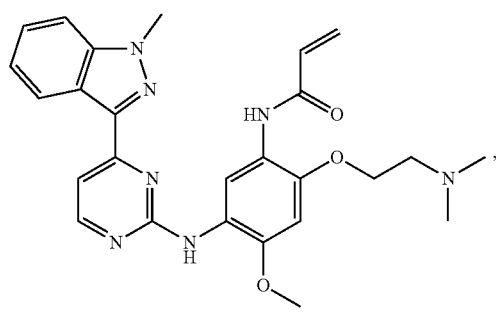
I-52
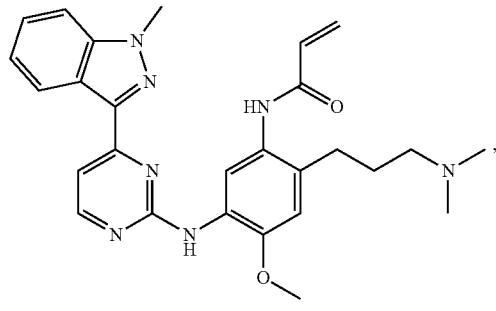 [SMILES: C=CC(=O)Nc1cc(Nc2nccc(-c3nn(C)c4ccccc34)n2)c(OC)cc1OCCN(C)C]
I-53
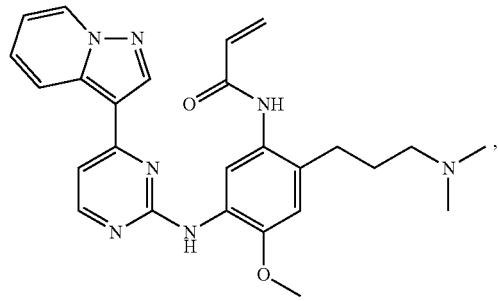
I-54
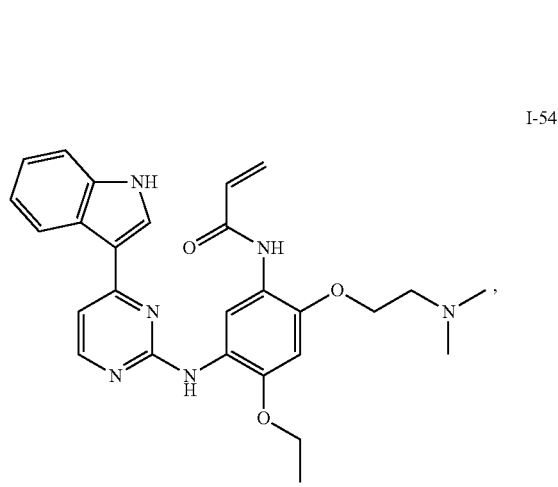
I-55
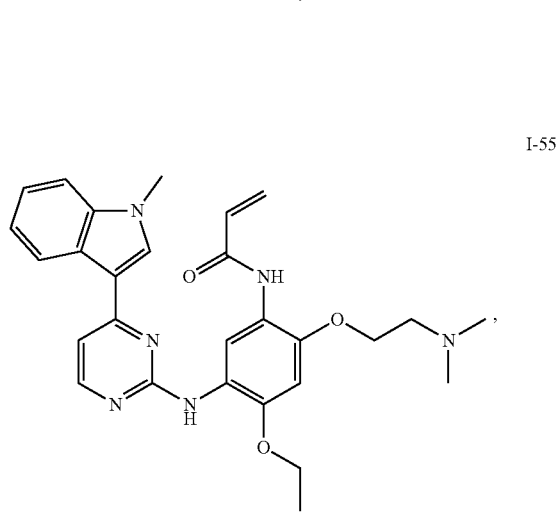
I-56
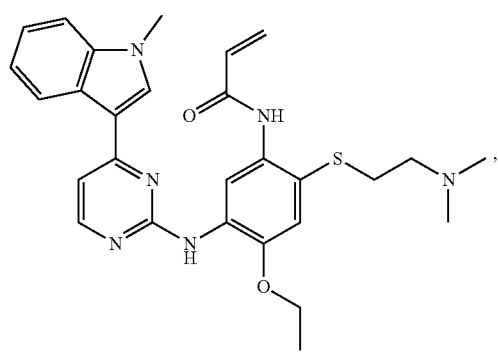

-continued
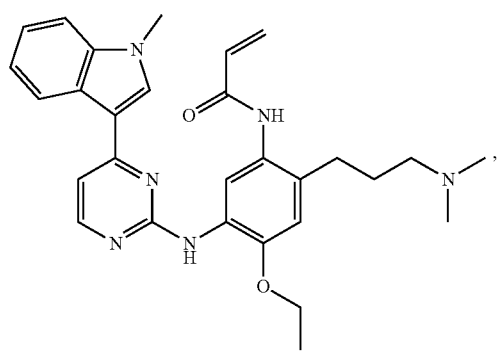
I-57
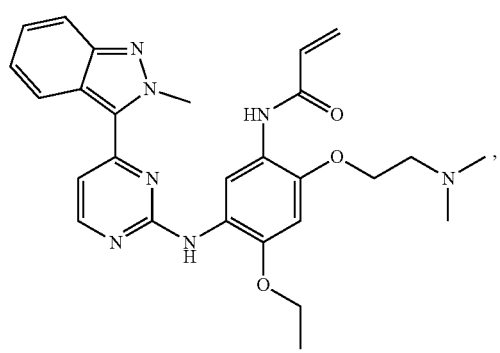
I-58
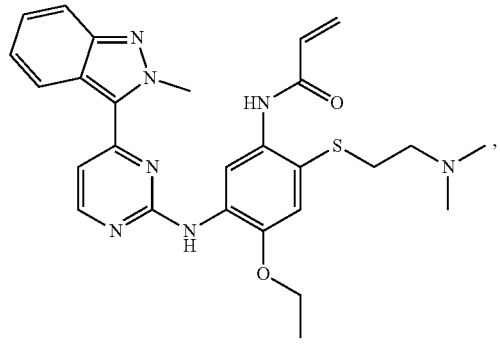
I-59
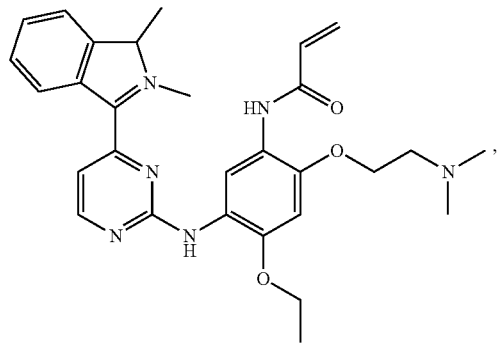
I-60
-continued
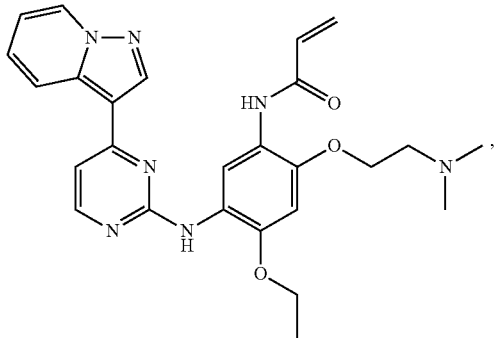
I-61
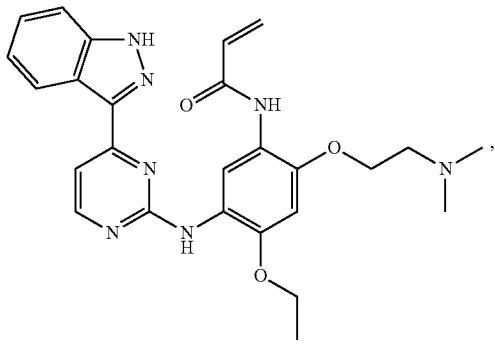
I-62
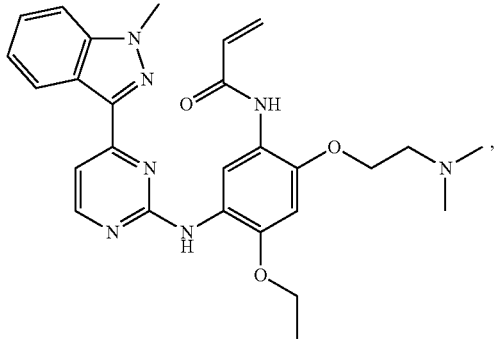
I-63
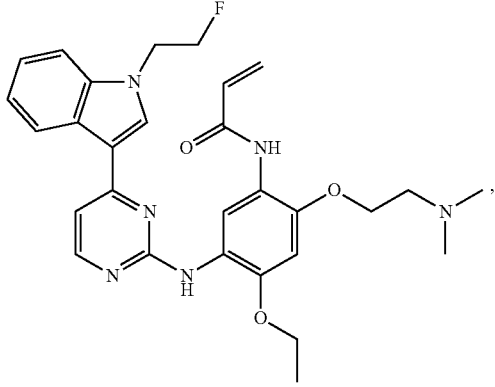
I-64

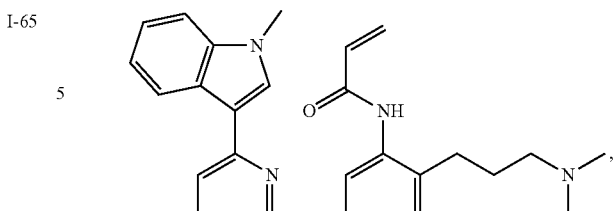
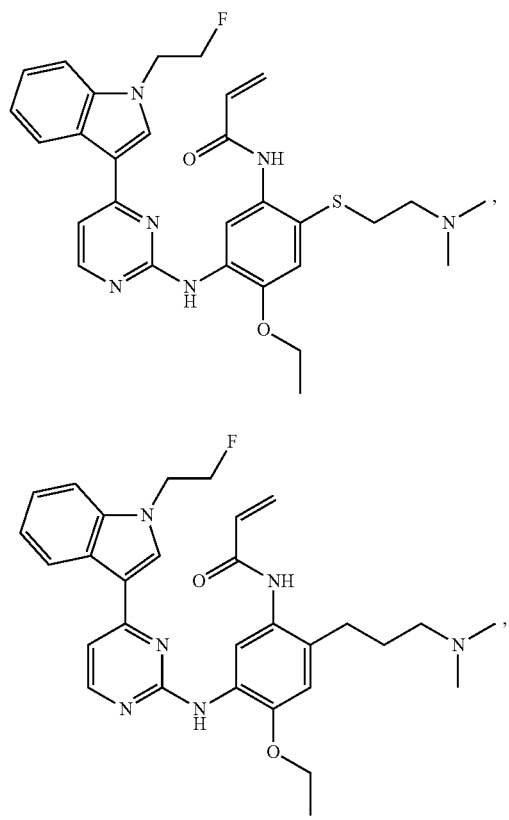
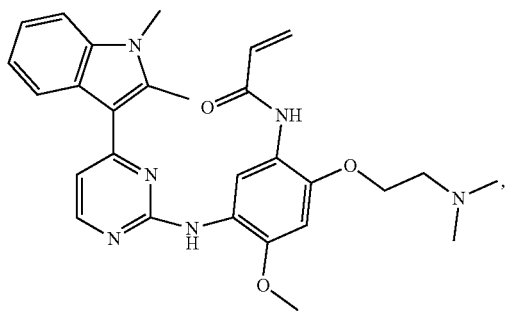
or a pharmaceutically acceptable salt, solvate, or prodrug thereof.
In one embodiment, sometimes preferred, the compound of formula (I) is selected from the group consisting of:
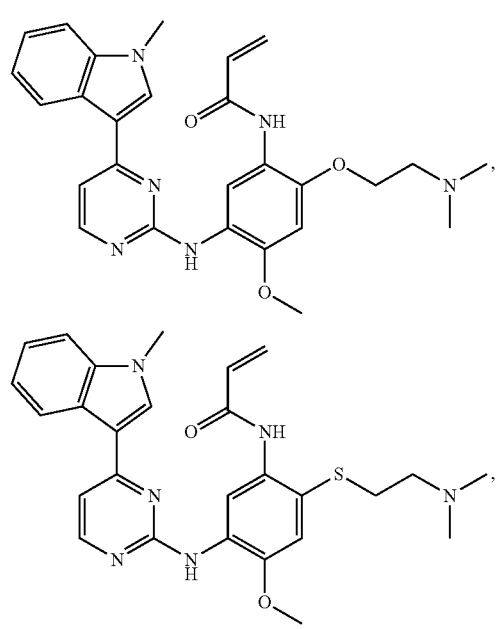
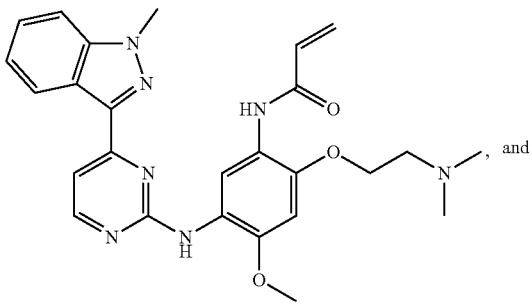
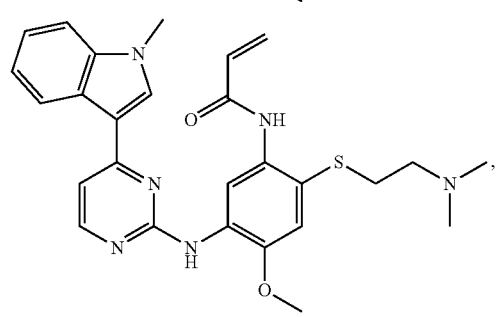
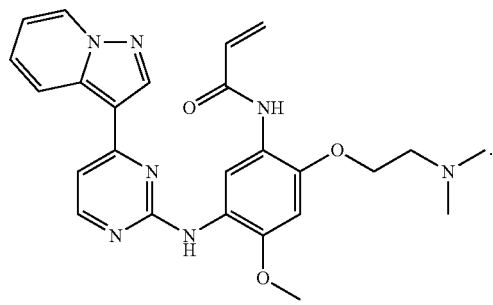
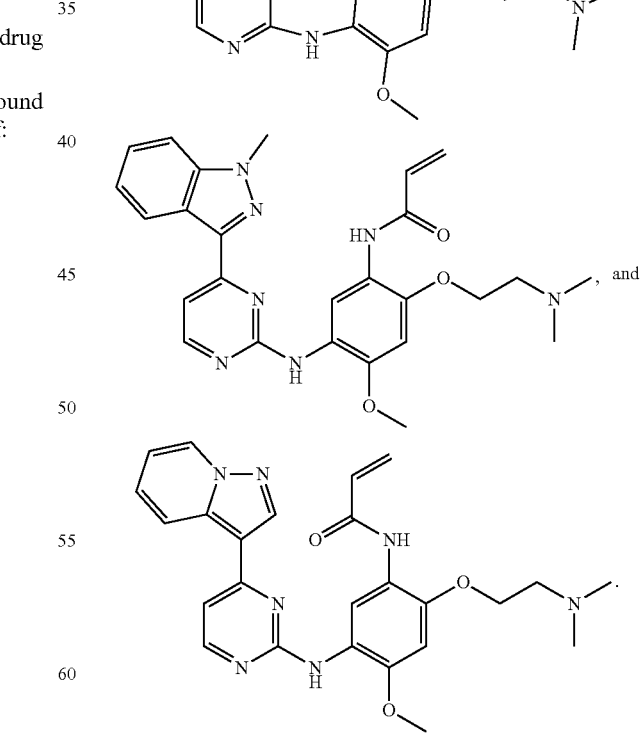
As a person of ordinary skill in the art would understand, the compounds of formula (I) or (II) as described in the present disclosure encompass any plausible combinations of the respective embodiments described herein so long as they would not violate chemical bonding principles, but form stable compounds.

In one embodiment, sometimes preferably, the present invention provides a method of treating a human subject having non-small cell lung carcinoma harboring an EGFR mutation, comprising the step of administering an effective amount of the EGFR tyrosine kinase inhibitor of Formula 1:

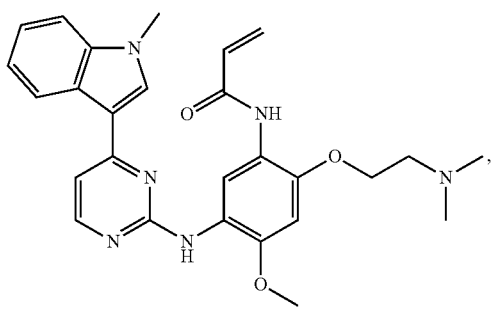

1 or a pharmaceutically acceptable salt, solvate, or prodrug thereof, in combination with a synergistically effective amount of the CDK4/6 inhibitor of Formula 2:

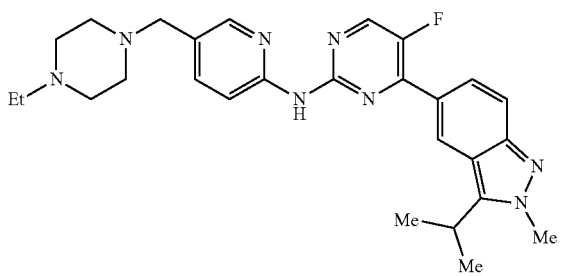

2 or a pharmaceutically acceptable salt, solvate, or prodrug thereof.

In one embodiment, sometimes preferably, the present invention provides a method of treating a human subject having non-small cell lung carcinoma harboring an EGFR mutation, comprising the step of administering an effective amount of the EGFR tyrosine kinase inhibitor of Formula 1:

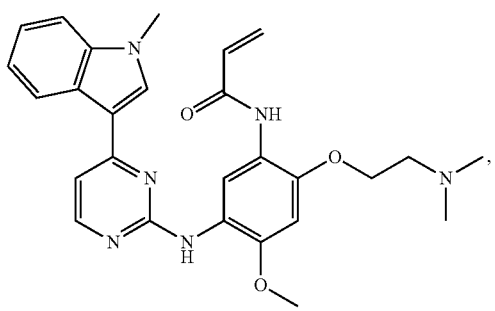

1 or a pharmaceutically acceptable salt, solvate, or prodrug thereof, in combination with a synergistically effective amount of the CDK4/6 inhibitor of Formula II-32:

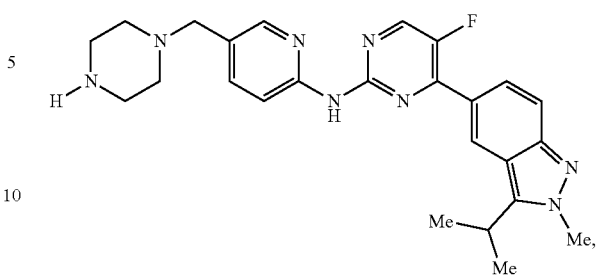

II-32 or a pharmaceutically acceptable salt, solvate, or prodrug thereof.

In one embodiment, sometimes preferably, the non-small cell lung carcinoma harbors the EGFR T790M resistance mutation.

In one embodiment, sometimes preferably, the salt form of the inhibitor of Formula 1 is a methanesulfonate salt, and the salt form of the inhibitor of Formula 2 is a hydrochloride.

In another embodiment, sometimes preferably, the present invention provides a method of treating a human subject having an EGFR-mutant cancer that has developed an acquired resistance to an epidermal growth factor receptor tyrosine kinase inhibitor (EGFR-TKI) treatment, comprising the step of administering to the human subject an effective amount of the EGFR tyrosine kinase inhibitor of Formula 1, or a pharmaceutically acceptable salt, solvate, or prodrug thereof, in combination with a synergistically effective amount of the CDK4/6 inhibitor of Formula 2, or a pharmaceutically acceptable salt, solvate, or prodrug thereof.

In a particular preferred embodiment, the EGFR-mutant cancer is breast cancer.

In a particular preferred embodiment, the breast cancer is estrogen receptor-positive breast cancer, progesterone receptor-positive breast cancer, or HER2-positive breast cancer.

In another embodiment, sometimes preferred, the EGFR-mutant cancer is bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, or thyroid cancer.

In another embodiment, sometimes preferably, the present invention provides a method of treating a human subject having an EGFR-mutant cancer, wherein the subject is EGFR-TKI-treatment naive, comprising the step of administering to the human subject an effective amount of the EGFR tyrosine kinase inhibitor of Formula 1, or a pharmaceutically acceptable salt, solvate, or prodrug thereof, with a synergistically effective amount of the CDK4/6 inhibitor of Formula 2 or a pharmaceutically acceptable salt, solvate prodrug thereof.

In another aspect, the present invention provides use of a compound of formula (I), or a pharmaceutically acceptable salt, solvate, or prodrug thereof, in combination with a synergistically effective amount of the CDK4/6 inhibitor of Formula 2, or a pharmaceutically acceptable salt, solvate, or prodrug thereof, in the manufacture of a medicament for treatment of a cancer associated with a mutant of epidermal growth factor receptor (EGFR) in a subject.

In some embodiments, the cancer is selected from the group consisting of lung cancer, breast cancer, brain cancer, bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, or thyroid cancer.

In some preferred embodiments, the cancer is lung cancer, sometimes preferably non-small cell lung cancer.

In some preferred embodiments, the cancer is breast cancer, sometimes preferably estrogen receptor-positive breast cancer, progesterone receptor-positive breast cancer, or HER2-positive breast cancer.

In some preferred embodiments, the cancer is brain cancer, sometimes preferably metastatic brain cancer, in particular, metastatic cancer originated from EGFR mutant-related non-small cell lung cancer.

In some embodiments, the EGFR inhibitor and CDK4/6 inhibitor may be combined together in the manufacture of a combo therapeutic agent in an appropriate portion that would cause synergistic effect on the treatment of the subject. For example, a pharmaceutical composition can include a therapeutically effective amount of EGFR inhibitor (the first compound), a therapeutically effective amount of CD4/6 inhibitor (the second compound), and a pharmaceutically acceptable carrier.

In some embodiments, the EGFR inhibitor and CDK4/6 inhibitor may be administered separately as distinct regimens concurrently.

In some embodiments, the EGFR inhibitor may be administered in a time period prior to the administration of the CDK4/6 inhibitor.

In some other embodiments, the EGFR inhibitor may be administered at a time later than administration of the CDK4/6 inhibitor.

In one specific embodiment, the invention provides a method of treating a human subject having non-small cell lung carcinoma harboring an EGFR mutation, where the method comprises the step of administering an effective amount of the EGFR tyrosine kinase inhibitor of Formula 1, or a pharmaceutically acceptable salt thereof, in combination with the CDK4/6 inhibitor of Formula 2, or a pharmaceutically acceptable salt thereof, preferably in synergistically effective amounts. The administration can be simultaneous or sequential. The non-small cell lung carcinoma of the method can further harbor the EGFR T790M resistance mutation. In a preferred embodiment, the Formula 1 inhibitor salt form is methanesulfonate, sometimes preferably mono-methanesulfonate, and the Formula 2 inhibitor salt form is hydrochloride.

In one specific embodiment, the invention provides a method of treating a human subject having an EGFR-mutant cancer that has developed an acquired resistance to an epidermal growth factor receptor tyrosine kinase inhibitor (EGFR-TKI) treatment, where the method comprises the step of administering to the human subject an effective amount of the EGFR tyrosine kinase inhibitor of Formula 1, or a pharmaceutically acceptable salt thereof, in combination with a synergistically effective amount of the CDK4/6 inhibitor of Formula 2, or a pharmaceutically acceptable salt thereof. The administration can be simultaneous or sequential. The EGFR-mutant cancer is selected from the group consisting of bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, and thyroid cancer. In a preferred embodiment, the EGFR-mutant cancer is breast cancer. The breast cancer can be estrogen receptor-positive breast cancer, progesterone receptor-positive breast cancer, or HER2-positive breast cancer. In a preferred embodiment, the Formula 1 inhibitor salt form is methanesulfonate, sometimes preferably mono-methanesulfonate, and the Formula 2 inhibitor salt form is hydrochloride.

In one specific embodiment, the invention provides a method of treating a human subject having an EGFR-mutant cancer, where the subject is EGFR-TKI-treatment naive, and where the method comprises the step of administering to the human subject an effective amount of the EGFR tyrosine kinase inhibitor of Formula 1, or a pharmaceutically acceptable salt thereof, with the CDK4/6 inhibitor of Formula 2, or a pharmaceutically acceptable salt thereof, preferably in synergistically effective amounts. The administration can be simultaneous or sequential. The EGFR-mutant cancer is selected from the group consisting of bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, and thyroid cancer. In a preferred embodiment, the EGFR-mutant cancer is breast cancer. The breast cancer can be estrogen receptor-positive breast cancer, progesterone receptor-positive breast cancer, or HER2-positive breast cancer. In a preferred embodiment, the Formula 1 inhibitor salt form is methanesulfonate, sometimes preferably mono-methanesulfonate, and the Formula 2 inhibitor salt form is hydrochloride.

As a person of ordinary skill in the art would appreciate, any feasible combination of a compound of formula (I), or a pharmaceutically acceptable salt, solvate, or prodrug thereof, with a compound of formula (II), or a pharmaceutically acceptable salt, solvate, or prodrug thereof, in any embodiment disclosed herein, so long as such combination can generate some synergistic effect in the treatment on a subject in need of such treatment, is encompassed in the present invention.

When any compound is used in the present invention, it is inclusive of any of its pharmaceutically acceptable forms, including but not limited to isomers, tautomers, salts, solvates, polymorphs, prodrugs, and the like. It should be understood that the term "compound" includes any or all of such forms, whether explicitly stated or not, although at times, only certain terms, such as "salt" and "prodrug", are explicitly stated.

Unless specifically defined otherwise, all terms as used herein take their ordinary meanings as a person of ordinary skill in the art would interpret or understand.

The term "a," "an," or "the," as used herein, represents both singular and plural forms. In general, when either a singular or a plural form of a noun is used, it denotes both singular and plural forms of the noun.

When the term "about" is applied to a parameter, it indicates that the parameter can vary by ±10%, preferably within ±5%, inclusive of any number of from the lower limit to the upper limit. When the term "about" is applied to a range, it is applicable to both the lower and upper limits of the range. As would be understood by a person skilled in the art, when a parameter is not critical, a number is often given only for illustration purpose, instead of being limiting.

"Alkoxy" means the group —OR wherein R is alkyl, as defined herein. Representative examples include methoxy, ethoxy, propoxy, isopropoxy, sec-butoxy, tert-butoxy, or the like.

"Alkyl" refers to a group derived from a straight or branched chain saturated hydrocarbon by removal of a hydrogen from one of the saturated carbons. The alkyl group preferably contains from one to eight carbon atoms, sometimes preferably one to six carbon atoms, and sometimes even more preferably one to four carbon atoms. Representative examples of alkyl group include, but are not limited to, methyl, ethyl, n-propyl, isopropyl, n-butyl, sec-butyl, tert-butyl, pentyl, hexyl, or the like. A "lower alkyl," "lower alkoxy," or "lower haloalkyl" means an alkyl group, or the alkyl part, having one to four, sometimes preferably one to three or one to two, carbon atoms.

The term "cyano," as used herein, refers to —CN.

The term "cycloalkyl," as used herein, refers to a group derived from a monocyclic saturated carbocycle, having preferably three to eight, more preferably three to six, carbon atoms, by removal of a hydrogen atom from the saturated carbocycle. Representative examples of cycloalkyl groups include, but are not limited to, cyclopropyl, cyclopentyl, and cyclohexyl.

The terms "halo" and "halogen," as used herein, refer to F, Cl, Br, or I.

The term "haloalkyl," as used herein, refers an alkyl group substituted by at least one halogen atom. The haloalkyl group can be an alkyl group of which all hydrogen atoms are substituted by halogens. Representative examples of haloalkyl include, but are not limited to, trifluoromethyl, fluoromethyl, difluoromethyl, bromomethyl, 1-chloroethyl, perchloroethyl, 2-fluoroethyl, or the like.

The term "heterocyclyl," as used herein, refers to a 3- to 10-membered monocyclic or bicyclic, nonaromatic group comprising one or more, preferably one to three, heteroatoms independently selected from nitrogen (N), oxygen, and sulfur (S, S(O) or S(O)$_2$) in the nonaromatic ring(s). The heterocyclyl groups of the present disclosure can be attached to the parent molecular moiety through a carbon atom or a nitrogen atom in the group. A heterocylcyl group can be saturated or unsaturated, for example, containing one or more double bond(s) in the ring. Unless otherwise stated, the valency of the group may be located on any atom of any ring within the radical, valency rules permitting. Examples may include, but are not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, tetrahydrofuranyl, 2-oxopiperidinyl, thiomorpholinyl, pyrazolidinyl, imidazolinyl, imidazolidinyl, or the like.

When any group, for example, "cycloalkyl" or "heterocyclyl," is said to be "substituted or unsubstituted" or "optionally substituted," unless specifically defined, it means that the group is or is not substituted by from one to five, sometimes preferably one to three or one to two, substituents independently selected from halogen, $C_1$-$C_6$ alkyl, $C_1$-$C_6$ alkoxy, $C_1$-$C_6$ haloalkyl, and cyano.

The term "solvate," as used herein, means a physical association of a compound of this invention with one or more, preferably one to three, solvent molecules, whether organic or inorganic. This physical association includes hydrogen bonding. In certain instances the solvate will be capable of isolation, for example when one or more, preferably one to three, solvent molecules are incorporated in the crystal lattice of the crystalline solid. Exemplary solvates include, but are not limited to, hydrates, ethanolates, methanolates, and isopropanolates. Methods of solvation are generally known in the art.

"Prodrug" refers to compounds that can be transformed in vivo to yield the active parent compound under physiological conditions, such as through hydrolysis in blood. Common examples include, but are not limited to, ester and amide forms of a compound having an active form bearing a carboxylic acid moiety. Amides and esters of the compounds of the present invention may be prepared according to conventional methods. In particular, in the present invention, a prodrug may also be formed by acylation of an amino group or a nitrogen atom in a heterocyclyl ring structure, which acyl group can be hydrolyzed in vivo. Such acyl group includes, but is not limited to, a $C_1$-$C_6$ acyl, preferably $C_1$-$C_4$ acyl, and more preferably $C_1$-$C_2$ (formyl or acetyl) group, or benzoyl. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The term "subject", as used herein, refers to a human or other mammalian animal, such as monkeys, dogs, cats, horses, and the like. The term is intended encompass, sometimes is interchangeable with, "patient."

The term "administering" or "administration", as used herein, refers to providing a compound or pharmaceutical composition to a subject suffering from or at risk of the diseases or conditions to be treated or prevented.

Any route of administration may be suitable for the present invention. In one embodiment, the compound(s) of the present invention may be administered to the subject in a solid dosage form such as tablet, capsule, or the like. In one embodiment, the compound(s) of the present invention may be administered to the subject via intravenous injection. In another embodiment, the compounds of the present invention may be administered to the subject via any other suitable systemic deliveries, such as oral, parenteral, intranasal, sublingual, rectal, or transdermal administrations.

The term "therapeutically effective amount", as used herein, refers to an amount of a compound or composition that will elicit desired or intended biological or medical response of a subject as sought for by a medical doctor, veterinarian, or researcher. The therapeutically effective amount of the compounds and the specific pharmaceutically acceptable carrier will vary depending upon, e.g., the age, weight, sex of the subject, the mode of administration, and the diseases or conditions being treated.

The term "pharmaceutically acceptable," when used before a compound, salt, prodrug, composition, or carrier, means that such compound, salt, prodrug, composition or carrier is suitable for administration to a subject for the treatment without causing intolerable side effects to the subject in view of the treatment needed.

The term "pharmaceutically acceptable carrier," as used herein, refers to materials compatible with the compounds used in the present invention and useful for the purpose of administering the compounds in the method of the present invention, which are preferably non-toxic, or otherwise inert and pharmaceutically acceptable. A pharmaceutically acceptable carrier may be solid, liquid, or gaseous materials, and includes any and all dry powder, solvents, dispersion media, coatings, antibacterial and antifungal agents, isotonic agents, absorption delaying agents, and the like. Examples of such carriers include oils such as corn oil, buffers such as phosphate-buffered saline (PBS), saline, polyethylene glycol, glycerin, polypropylene glycol, dimethylsulfoxide, an amide such as dimethylacetamide, a protein such as albumin, and a detergent such as Tween 80, mono- and oligopolysaccharides such as glucose, lactose, cyclodextrins, starch, and the like.

As described herein, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. See S. M. Berge, et al., "Pharmaceutical Salts," J. Pharm. Sci. 1977, 66, 1-19.

The formulation used in the present invention may also contain stabilizers, preservatives, buffers, antioxidants, or other additives known to those of skill in the art. The use of such media and agents for pharmaceutically-active substances is well known in the art.

The term "synergistic", or the like, as used herein, refers to an effect caused by combination of two or more agents that is more than the additive effects of the two or more agents used individually. Such synergistic effect of a combination therapy includes higher efficacy, lower side effect, or both. In some embodiments, the synergistic effect includes the substantially lowered side effects of both therapeutic inhibitors owing to the lowered dosages of both, while the collective therapeutic efficacy is kept at about the same or improved level. In some embodiments, the synergistic effect includes substantially improved efficacy in inhibiting proliferation of cancer cells while the side effects caused by both agents are kept at about same or lower level. A synergistic effect permits the effective treatment of a disease using lower doses of individual agents. Overall, a synergistic combination of the two or more agents may result in an improved treatment of a disease as compared to single therapies.

Combination therapy may allow use of lower doses of the first therapeutic agent, e.g., EGFR inhibitor, or the second therapeutic agent, e.g., CD4/6 inhibitor, or lower doses of both therapeutic agents than would normally be required when either drug is used alone. The present invention encompasses any and all of such "synergistic" effects.

The pharmaceutical compositions may contain the EGFR inhibitor and the CDK4/6 inhibitor used in the method of this invention in a total amount of from 0.01% to 99% by weight of the total composition, preferably from 0.1% to 80% by weight of the total composition, and more preferably 0.1% to 50% by weight of the total composition. The weight ratio between the EGFR inhibitor and the CDK4/6 inhibitor can be in the range of from 1:20 to 20:1, sometimes preferably 1:15 to 15:1, and sometimes more preferably 1:10 to 10:1.

For systemic administration, the daily dosage of EGFR inhibitor as employed for adult human treatment will range from about 0.01 mg/kg to about 150 mg/kg, preferably about 0.05 mg/kg to about 100 mg/kg, and sometimes more preferably about 0.1 mg/kg to about 50 mg/kg.

EXAMPLES

Materials

N-[2-[2-(Dimethylamino)ethoxy]-4-methoxy-5-[[4-(1-methyl-1H-indol-3-yl)-2-pyrimidinyl]amino]phenyl]-2-propenamide methane sulfonate salt ($1 \cdot CH_3SO_3H$)

Preparation of compounds of formula (I) in general, Compound 1 in particular, has been described in WO 2016/094821 A2, and the corresponding mono-methanesulfonate salts, in particular that of Compound 1, has been described in WO 2018/232235 A1, which are both hereby incorporated by reference in their entireties as if they are fully recited herein.

N-[5-[(4-Ethyl-1-piperazinyl)methyl]-2-pyridinyl]-5-fluoro-4-[2-methyl-3-(1-methylethyl)-2H-indazol-5-yl]-2-pyrimidinamine hydrochloride salt ($2 \cdot HCl$)

Preparation of compounds of formula (II) in general, Compound 2 in particular, has been described in WO 2016/014904 A1, which is hereby incorporated by reference in its entirety as if it is fully recited herein. Compound 2 (500 mg, 1.02 mmol) prepared according to WO 2016/014904 A1 was dissolved in 20 mL of methanol and treated with 1 equivalent of HCl (1.02 mmol). The resulting suspension was stirred at room temperature for 24 h and centrifuged at 10,000 rpm for 5 min. The solid was isolated and dried under vacuum at 40° C. for 24 h to afford the HCl salt of 2 (37 mg) as a light yellow powder.

Example 1. Antitumor Activity of 1 and 2 and their Combinations in the HCC827 Mouse Xenograft Model Cell Culture and Implantation. HCC827 cells were cultured in a $CO_2$ incubator in culture media containing modified RPMI (Hyclone, Cat: SH30809.01); 10% fetal bovine serum (Gibco, Cat: 10099-141); 100 U/ml penicillin and 100 µg/ml streptomycin (Hyclone, Cat: SV30010). Cells were digested with 0.25% trypsin (Hyclone, Cat: SH30042.01) and subcultured every four days. When the required cells was in the logarithmic growth phase, the cell counts were collected and the tumors were subcutaneously implanted in Balb/c nude female mice (14-19 g) at $1 \times 10^7/0.2$ mL/mouse (50% Matrigel CORNING, Cat: 354234) in the right back side of each mouse. 8 days after implantation, 56 mice with tumor volume of 132-289 mm$^3$ were selected and randomly divided into 7 groups according to tumor volume and body weight.

Test Sample Preparation Formulation and Administration. A stock solution of 1 as the methanesulfonate salt was prepared at 0.3 mg/mL in normal saline. A stock solution of 2 as the hydrochloride salt was prepared 2.0 mg/mL in sterile water. The vehicle control was a solution of 0.5% sodium carboxymethyl cellulose in sterile water. All stock solutions were stored at 2-8° C. and prepared fresh on a weekly basis. The stock solutions were administered orally either individually or in combination at the indicated salt dosages depicted in FIG. 1 and Table 2 once a day for 14 days. Dosing was suspended when body weight lost more than 15%.

Tumor Volume Determination and Data Analysis. The tumor volumes were determined twice per week by measuring the length and width of each tumor with a Vernier caliper and calculating the tumor volume. All tumors were harvested on day 35 and weighed. The Tumor Weight Inhibition Rate ($IR_{TW}\%$) was calculated via the equation: $IR_{TW}\%=(1-(TW_{(treated)}/TW_{(control)}))\times 100\%$, where TW is defined as tumor weight. Histograms were generated using Prism GraphPad (mean±S.E.M.), and T analysis was used for statistical analysis. A p value less than 0.05 represents a significant difference between groups and a p value less than 0.01 represents a highly significant difference between groups.

Example 2. Antitumor Activity of 1 and 2 and their Combinations in the NCI-H1975-Luc Mouse Xenograft Model Cell Culture and Implantation. NCI-H1975-Luc cells (ATCC) were cultured in culture media containing modified RPMI 1640 medium, 1 mM Na pyruvate, 10 mM HEPES, 2.8 mL 45% glucose (1.25 g), 2 mM L-glutamine, 5 µg/ml blasticidin, 10% non-heat-inactivated fetal bovine serum (FBS), and 1×penicillin/streptomycin/L-glutamine (PSG). Cells were digested with 0.25% trypsin and 2.21 mM ethylenediaminetetraacetic acid (EDTA) in Hank's Balanced Salt Solution (HBSS). The tumors were subcutaneously implanted with serum-free RPMI 1640 medium at $5\times 10^6$ trypan-excluding cells in Hsd:Athymic Nude-Foxn1$^{nu}$ female mice at age 6-7 weeks (20.7-22.7 g) at 0.200 µL/mouse (50% Matrigel) in the high right axilla of each mouse. All mice were sorted into study groups based on caliper estimation of tumor burden. The mice were distributed to ensure that the mean tumor burden for all groups was within 10% of the overall mean tumor burden for the study population.

Test Sample Preparation Formulation and Administration. A stock cloudy white suspension of 1 as the methanesulfonate salt was prepared at 0.5 mg freebase/mL in 0.5% methylcellulose in sterile water. A clear colorless stock solution of 2 as the hydrochloride salt was prepared at 2.0 mg freebase/mL in sterile water. The vehicle control for 1 was a solution of 0.5% sodium carboxymethyl cellulose in sterile water and the vehicle control for 2 was sterile water. The stock solutions were prepared fresh on a daily basis and administered orally either individually or in combination at the indicated free base dosages depicted in FIG. 2 once a day for 14 days.

Tumor Growth and Tumor Volume Determination. The mean estimated tumor burden for all groups in the experiment on the first day of treatment was 172 mm$^3$, and all of the groups in the experiment were well-matched (range of group means, 168-175 mm$^3$). All animals weighed at least 17.9 g at the initiation of therapy. Mean group body weights at first treatment were also well-matched (range of group means, 20.7-22.7 g). A tumor burden of 1000 mm$^3$ was chosen for evaluation of efficacy by time to progression. In the Control Group, the median time to progression was 12.5 days, and the median tumor volume doubling time was 4.0 days. Control animals experienced a 1.4 g (6.4%) mean weight gain during the treatment regimen. There were no spontaneous regressions in the Control Group. The tumor volumes were determined on days 4, 6, 7, 10, 12, 14, 17, 19, 21 and 24 by measuring each tumor with a caliper and calculating the tumor volume.

Time to Progression (TP). Time to progression is a surrogate for lifespan or time on study. It is used for studies that involve IACUC mandated euthanasia of animals for excessive tumor burdens (even if the animals otherwise appear normal). Time to progression data is analyzed by Kaplan Meier methods just as traditional life span data. The Time to Progression (TP) for an individual animal is the number of days between initiation of treatment and the death or required euthanasia of that animal. The day of first treatment is the day of first treatment in the study as a whole and is not specific to the group in question. When euthanasia is prompted for excessive tumor burden (>1000 mm$^3$), the day of euthanasia is calculated from a log-linear interpolation between the adjacent data points on either side of the tumor burden limit, not from the actual day of euthanasia. Animals euthanized for scheduled sampling or other causes unrelated to disease progression or therapy are excluded from this calculation. The median Time to Progression for a group is used to calculate the % Increase in Time to Progression (% ITP). The % Increase in Time to Progression (% ITP) is calculated by the following equation:

$$\% \, ITP = \left\{ \frac{[(\text{median Treated } TP) - (\text{median Control } TP)]}{\text{median Control } TP} \right\} * 100.$$

Figure 2:
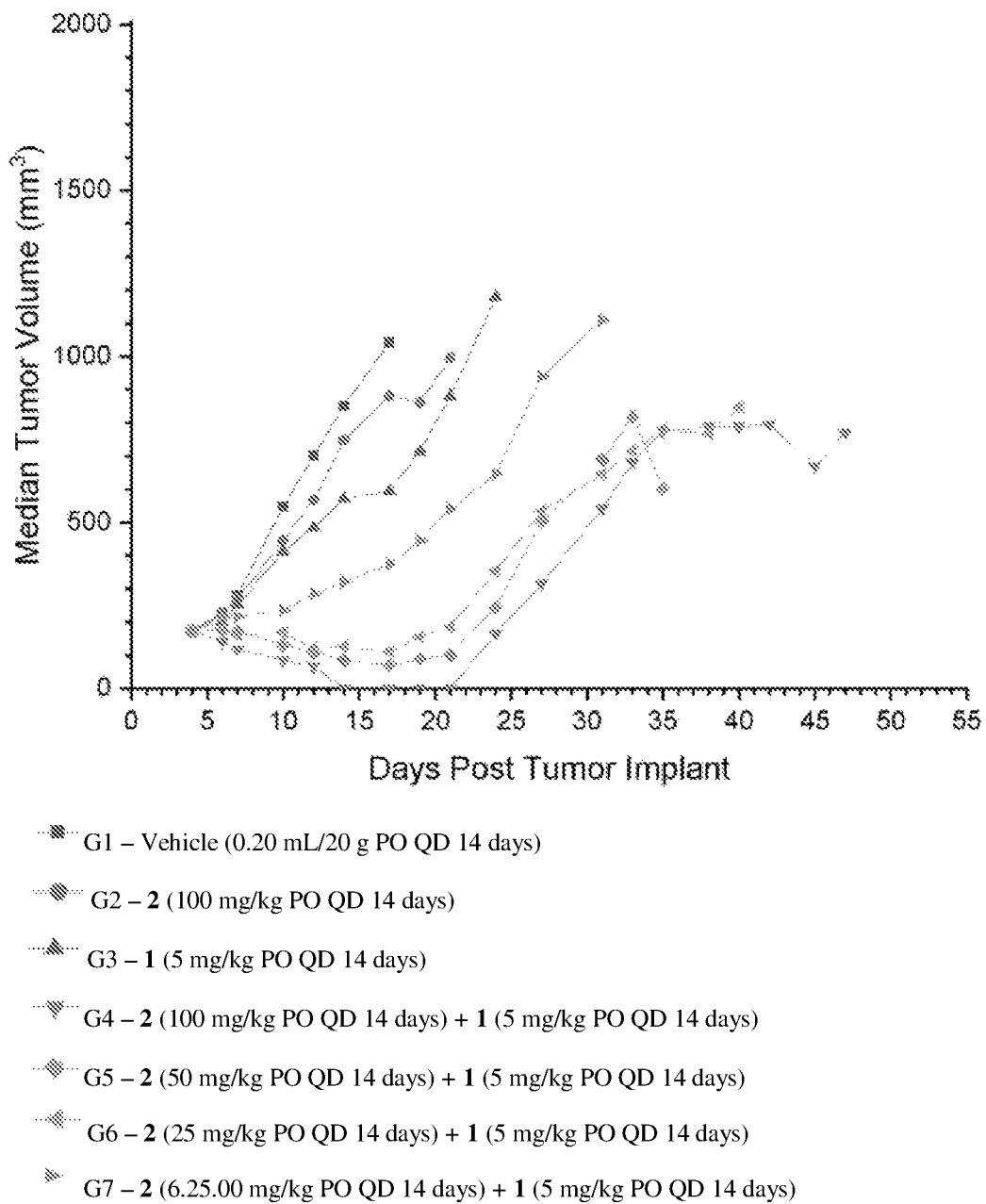
FIG. 2 illustrates a graph of the anti-tumor effects of EGFR tyrosine kinase inhibitor 1, CDK4/6 inhibitor 2 and their combinations in a NCI-H1975-Luc mouse xenograft tumor model (mean±SD, n=10).

The sensitivity of lung cancer cells towards EGFR tyrosine kinase inhibitor 1 is enhanced by simultaneous dosing with the selective CDK4/6 inhibitor 2 in the HCC827 and NCI-H1975 human non-small cell lung carcinoma mouse xenograft models as shown in FIGS. 1 and 2, respectively. HCC827 tumors harbor the delE746-A750 activating mutation whereas NCI-H1975 tumors harbor both the L858R activating mutation and the T790M resistance mutation.

In the HCC827 mouse xenograft model (Example 1), compound 1 (as the methane sulfonate salt) was dosed at 3 mg/kg by itself and in combination with compound 2 (as the hydrochloride salt) at either 5, 10 or 20 mg/kg once a day for 21 days. As shown by the tumor growth curves (FIG. 1), the efficacy of a 3 mg/kg dose of 1 in this model is increased in a dose-dependent manner upon co-dosing with increasing amounts of 2. A similar increase in efficacy was also observed in the tumor weight inhibition rates (Table 2). The tumor weight inhibition rate of a 3 mg/kg dose of 1 improved in a dose-dependent manner from 83.1% to 95.6% when it was co-dosed with increasing amounts (5-20 mg/kg) of 2.

A synergistic antitumor effect was also observed with combinations of compounds 1 and 2 in a NCI-H1975-Luc human non-small cell lung carcinoma mouse xenograft model (Example 2) as shown in FIG. 2. Compound 1 was dosed at 5 mg/kg by itself and in combination with 2 at either 6.25, 25, 50 or 100 mg/kg once a day for 14 days. As shown by the tumor growth curves in FIG. 2, the efficacy of a 5 mg/kg dose of 1 in this model is clearly increased in a dose dependent manner upon co-dosing with increasing amounts of 2, with the 100 mg/kg dose being the most effective. Combination treatments of 1 and 2 produced a percent increase in time to progression (% ITP) ranging from 90-257%.

TABLE 2

Effects of 1 and 2 on Tumor Weight in the HCC827 Mouse Xenograft Model [a]

| Group [b] | Tumor Weight (g)[c] | Tumor Weight Inhibition Rate (%)[d] |
|---|---|---|
| Vehicle Control (0.5% CMC Na) [e] | 0.8406 ± 0.4170 | |
| 1 (3 mg/kg) | 0.1423 ± 0.1152 | 83.1[f] |
| 2 (20 mg/kg) | 0.5864 ± 0.2235 | 30.2 |
| 1 (3 mg/kg) + 2 (20 mg/kg) | 0.0370 ± 0.0281 | 95.6[f] |
| 1 (3 mg/kg) + 2 (10 mg/kg) | 0.0522 ± 0.0418 | 93.8[f] |
| 1 (3 mg/kg) + 2 (5 mg/kg) | 0.0666 ± 0.0573 | 92.1[f] |

[a] Compounds 1 and 2 were administered as a 1.0 methanesulfonate and a 1.0 hydrochloride salts, respectively.
[b] All groups were dosed orally QD for 21 days and the tumors were harvested on day 35.
[c] Mean ± standard deviation (n = 8).
[d] Tumor Weight Inhibition Rate: $(IR_{TW} \%) = (1-(TW_{(treated)}/TW_{(control)})) \times 100\%$.
[e] 0.5% CMC Na is 0.5% sodium carboxymethyl cellulose in sterile water.
[f] $p < 0.01$, indicating highly statistically significant relative to control.

The results from both HCC827 and NCI-H1975-Luc xenograph studies demonstrate the ability to minimize the efficacious dose of the EGFR tyrosine kinase inhibitor 1 by combination therapy with the CDK4/6 inhibitor 2. The net effect of minimizing the amounts of 1 and 2 administered has the potential to reduce adverse side effects.

All of the patent or non-patent publications cited herein are hereby incorporated by reference. It will be understood by those of skill in the art that numerous and various modifications can be made to the compounds, compositions, and/or methods of the present invention without departing from the spirit of the invention. Therefore, the various embodiments of the present invention described herein are illustrative only and are not intended to limit the scope of the invention in any way. Many equivalents to the specific embodiments of the invention described herein may exist and are all intended to be encompassed by the present invention.

What is claimed is:

1. A method of treating a cancer associated with a mutant of epidermal growth factor receptor (EGFR) in a subject, the method comprising administering to the subject a therapeutically effective amount of an EGFR inhibitor of formula (I), or a pharmaceutically acceptable salt, solvate, or prodrug thereof, in combination with a synergistically effective amount of cyclin-dependent kinase (CDK) inhibitor of formula (II), or a pharmaceutically acceptable salt, solvate, or prodrug thereof; wherein the synergistically effective amount formula (II) comprises approximately 6.25 to 100 mg/kg of formula (II):

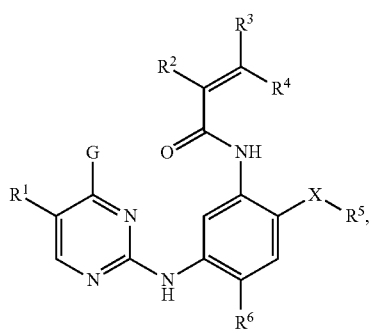

(I)

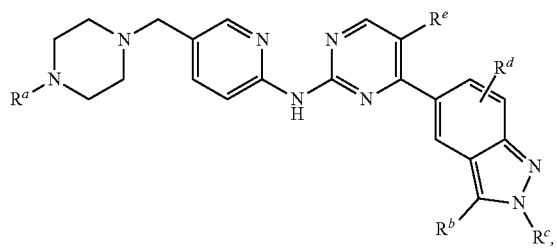

(II)

wherein in formula (I):

G is selected from the group consisting of substituted or unsubstituted 1H-indol-3-yl, substituted or unsubstituted 1H-indazol-3-yl, substituted or unsubstituted 2H-indazol-3-yl, and substituted or unsubstituted pyrazolo[1,5-a]-pyridin-3-yl, and substituted or unsubstituted 4,5,6,7-tetrahydropyrazolo[1,5-a]pyridin-3-yl;

X is oxygen, sulfur, or methylene;

$R^1$ is hydrogen, halogen, methyl, trifluoromethyl, or cyano;

$R^2$, $R^3$, and $R^4$ are the same or different and are independently selected from the group consisting of hydrogen, halogen, and trifluoromethyl;

$R^5$ is selected from the group consisting of lower alkyl, optionally substituted 3- to 6-membered heterocyclyl, $R^7R^8$N-(lower alkyl), and $R^7R^8$N-(cycloalkylalkyl), wherein $R^7$ and $R^8$ are the same or different and are independently selected from hydrogen and lower alkyl; and $R^6$ is lower alkoxy or lower alkyl;

and wherein in formula (II):

$R^a$ is hydrogen, $C_1$-$C_8$ alkyl, or $C_3$-$C_7$ cycloalkyl;

$R^b$ and $R^c$ are each independently selected from the group consisting of hydrogen, $C_1$-$C_8$ alkyl, $C_3$-$C_7$ cycloalkyl, and $C_3$-$C_7$ cycloalkylmethyl;

$R^d$ is hydrogen, halogen, $C_1$-$C_8$ alkyl, or $C_3$-$C_7$ cycloalkyl; and $R^e$ is hydrogen or halogen.

2. The method of claim 1, wherein $R^a$ is $C_1$-$C_6$ alkyl; $R^b$ is $C_1$-$C_6$ alkyl, $C_3$-$C_6$ cycloalkyl, or $C_3$-$C_6$ cycloalkylmethyl; and $R^c$ is $C_1$-$C_6$ alkyl or $C_3$-$C_6$ cycloalkyl.

3. The method of claim 1, wherein $R^a$ is methyl, ethyl, propyl, or isopropyl; $R^b$ is methyl, ethyl, propyl, isopropyl, cyclopropyl, cyclopentyl, cyclopropylmethyl, or cyclopentylmethyl; and $R^c$ is methyl, ethyl, propyl, isopropyl, or cyclopropyl.

4. The method of claim 1, wherein $R^d$ is hydrogen or halogen located at the 7-position of the indazole ring, and $R^e$ is hydrogen or fluoro, characterized by formula Ia:

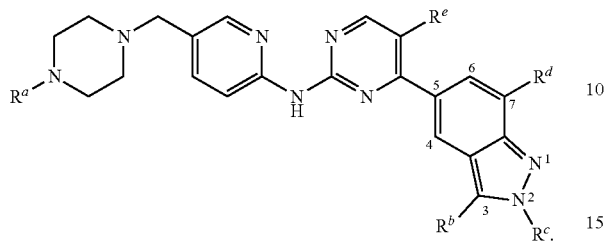

(IIa)

5. The method of claim 1, wherein $R^a$ is methyl or ethyl; $R^b$ is isopropyl, cyclopropyl, cyclopropylmethyl, or cyclopentyl; and $R^4$ is hydrogen or fluoro.

6. The method of claim 1, wherein the compound of formula (II) is selected from the group consisting of:

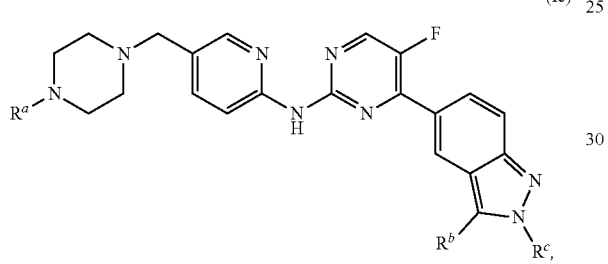

(Ic)

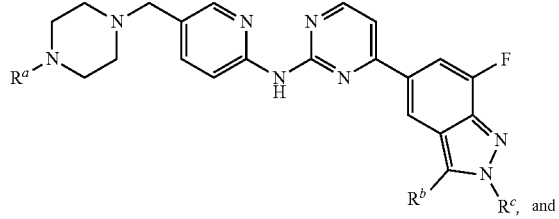

(Id)

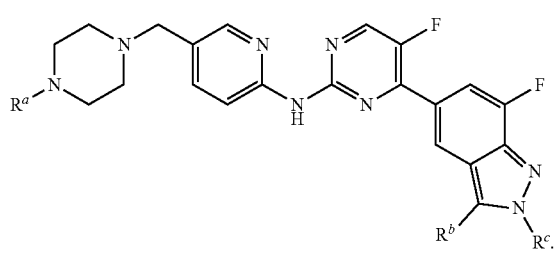

(Ie)

7. The method of claim 1, wherein the compound of formula (II) is selected from the list of Table 1 herein

| Example | Structure | Name |
|---|---|---|
| II-1 (or 2) | 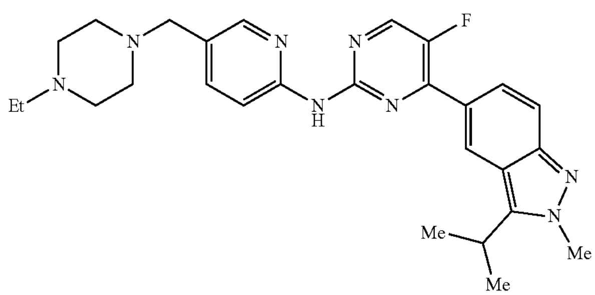 [SMILES: CCN1CCN(Cc2ccc(Nc3ncc(F)c(-c4ccc5nn(C)c(C(C)C)c5c4)n3)nc2)CC1] | N-(5-((4-ethylpiperazin-1-yl)methyl)pyridin-2-yl)-5-fluoro-4-(3-isopropyl-2-methyl-2H-indazol-5-yl)pyrimidin-2-amine |
| II-2 | 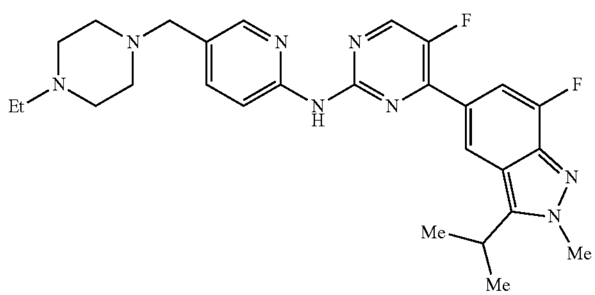 [SMILES: CCN1CCN(Cc2ccc(Nc3ncc(F)c(-c4cc(F)c5nn(C)c(C(C)C)c5c4)n3)nc2)CC1] | N-(5-((4-ethylpiperazin-1-yl)methyl)pyridin-2-yl)-5-fluoro-4-(7-fluoro-3-isopropyl-2-methyl-2H-indazol-5-yl)pyrimidin-2-amine |

-continued

| Example | Name |
|---------|------|
| II-3 | N-(5-((4-ethylpiperazin-1-yl)methyl)pyridin-2-yl)-4-(7-fluoro-3-isopropyl-2-methyl-2H-indazol-5-yl)pyrimidin-2-amine |
| II-4 | 4-(3-cyclopentyl-2-methyl-2H-indazol-5-yl)-N-(5-((4-ethylpiperazin-1-yl)methyl)pyridin-2-yl)-5-fluoropyrimidin-2-amine |
| II-5 | 4-(3-cyclopentyl-7-fluoro-2-methyl-2H-indazol-5-yl)-N-(5-((4-ethylpiperazin-1-yl)methyl)pyridin-2-yl)-5-fluoropyrimidin-2-amine |
| II-6 | 4-(3-cyclopentyl-7-fluoro-2-methyl-2H-indazol-5-yl)-N-(5-((4-ethylpiperazin-1-yl)methyl)pyridin-2-yl)pyrimidin-2-amine |
| II-7 | 4-(3-cyclopropyl-2-methyl-2H-indazol-5-yl)-N-(5-((4-ethylpiperazin-1-yl)methyl)pyridin-2-yl)-5-fluoropyrimidin-2-amine |

| Example | Structure | Name |
|---|---|---|
| II-8 | 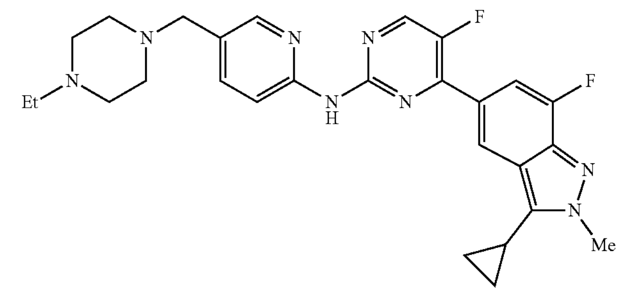 [SMILES: CCN1CCN(Cc2ccc(Nc3ncc(F)c(-c4cc(F)c5nn(C)c(C6CC6)c5c4)n3)nc2)CC1] | 4-(3-cyclopropyl-7-fluoro-2-methyl-2H-indazol-5-yl)-N-(5-((4-ethylpiperazin-1-yl)methyl)pyridin-2-yl)-5-fluoropyrimidin-2-amine |
| II-9 | 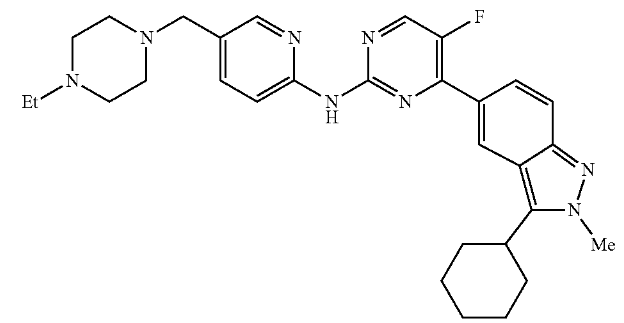 [SMILES: CCN1CCN(Cc2ccc(Nc3ncc(F)c(-c4ccc5nn(C)c(C6CCCCC6)c5c4)n3)nc2)CC1] | 4-(3-cyclohexyl-2-methyl-2H-indazol-5-yl)-N-(5-((4-ethylpiperazin-1-yl)methyl)pyridin-2-yl)-5-fluoropyrimidin-2-amine |
| II-10 | 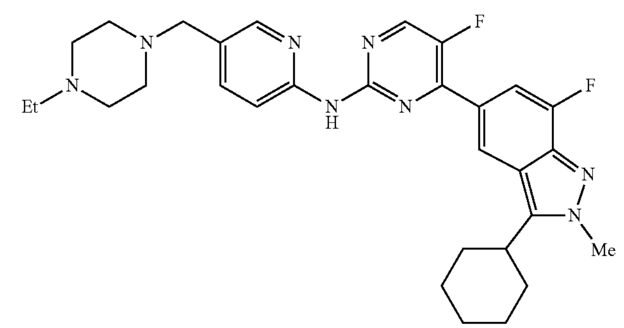 [SMILES: CCN1CCN(Cc2ccc(Nc3ncc(F)c(-c4cc(F)c5nn(C)c(C6CCCCC6)c5c4)n3)nc2)CC1] | 4-(3-cyclohexyl-7-fluoro-2-methyl-2H-indazol-5-yl)-N-(5-((4-ethylpiperazin-1-yl)methyl)pyridin-2-yl)-5-fluoropyrimidin-2-amine |
| II-11 | 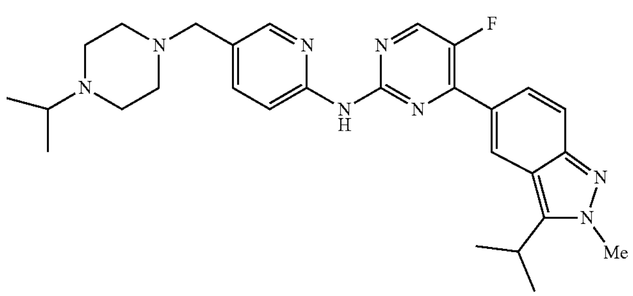 [SMILES: CC(C)c1c2cc(-c3nc(Nc4ccc(CN5CCN(C(C)C)CC5)cn4)ncc3F)ccc2nn1C] | 5-fluoro-4-(3-isopropyl-2-methyl-2H-indazol-5-yl)-N-(5-((4-isopropylpiperazin-1-yl)methyl)pyridin-2-yl)pyrimidin-2-amine |
| II-12 | 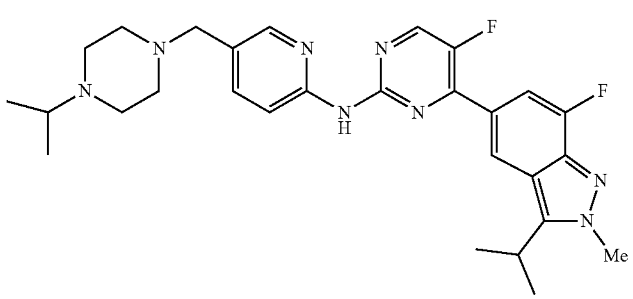 [SMILES: CC(C)c1c2cc(-c3nc(Nc4ccc(CN5CCN(C(C)C)CC5)cn4)ncc3F)cc(F)c2nn1C] | 5-fluoro-4-(7-fluoro-3-isopropyl-2-methyl-2H-indazol-5-yl)-N-(5-((4-isopropylpiperazin-1-yl)methyl)pyridin-2-yl)pyrimidin-2-amine |

| Example | Structure | Name |
|---|---|---|
| II-13 | 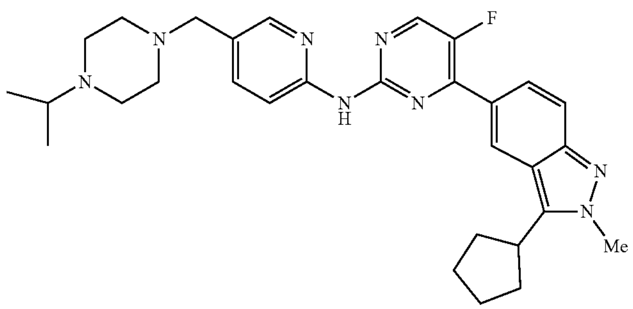 [SMILES: CC(C)N1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-isopropylpiperazin-1-yl)methyl)pyridin-2-yl)pyrimidin-2-amine |
| II-14 | 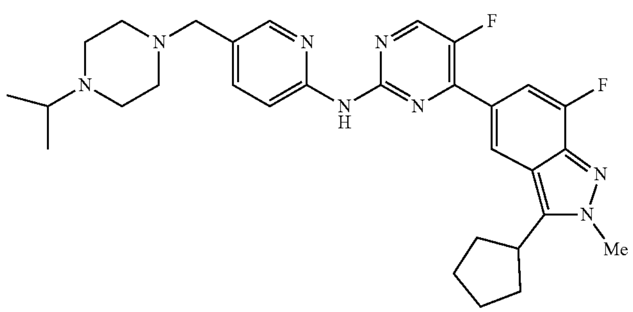 [SMILES: CC(C)N1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-isopropylpiperazin-1-yl)methyl)pyridin-2-yl)pyrimidin-2-amine |
| II-15 | 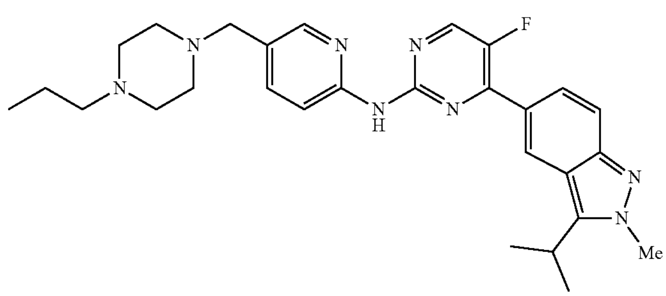 [SMILES: CCCN1CCN(Cc2ccc(Nc3ncc(F)c(-c4ccc5nn(C)c(C(C)C)c5c4)n3)nc2)CC1] | 5-fluoro-4-(3-isopropyl-2-methyl-2H-indazol-5-yl)-N-(5-((4-propylpiperazin-1-yl)methyl)pyridin-2-yl)pyrimidin-2-amine |
| II-16 | 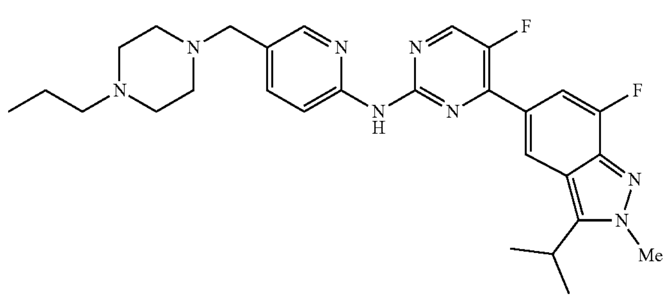 [SMILES: CCCN1CCN(Cc2ccc(Nc3ncc(F)c(-c4cc(F)c5nn(C)c(C(C)C)c5c4)n3)nc2)CC1] | 5-fluoro-4-(7-fluoro-3-isopropyl-2-methyl-2H-indazol-5-yl)-N-(5-((4-propylpiperazin-1-yl)methyl)pyridin-2-yl)pyrimidin-2-amine |
| II-17 | 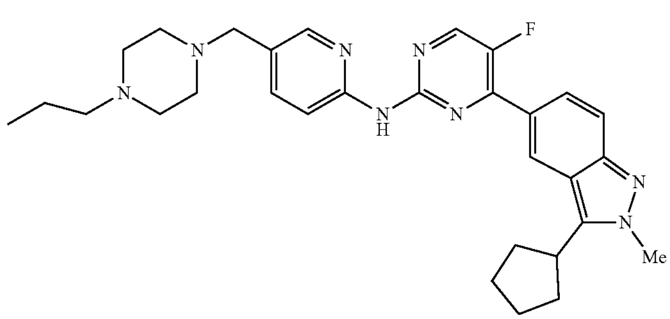 [SMILES: CCCN1CCN(Cc2ccc(Nc3ncc(F)c(-c4ccc5nn(C)c(C6CCCC6)c5c4)n3)nc2)CC1] | 4-(3-cyclopentyl-2-methyl-2H-indazol-5-yl)-5-fluoro-N-(5-((4-propylpiperazin-1-yl)methyl)pyridin-2-yl)pyrimidin-2-amine |

-continued

| Example | Structure | Name |
|---|---|---|
| II-18 | 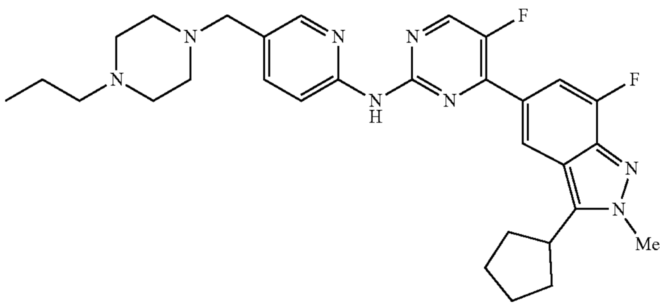 [SMILES: CCCN1CCN(Cc2ccc(Nc3ncc(F)c(-c4cc(F)c5nn(C)c(C6CCCC6)c5c4)n3)nc2)CC1] | 4-(3-cyclopentyl-7-fluoro-2-methyl-2H-indazol-5-yl)-5-fluoro-N-(5-((4-propylpiperazin-1-yl)methyl)pyridin-2-yl)pyrimidin-2-amine |
| II-19 | 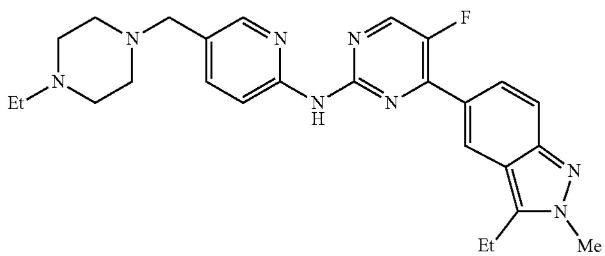 [SMILES: CCc1c2cc(-c3nc(Nc4ccc(CN5CCN(CC)CC5)cn4)ncc3F)ccc2nn1C] | 4-(3-ethyl-2-methyl-2H-indazol-5-yl)-N-(5-((4-ethylpiperazin-1-yl)methyl)pyridin-2-yl)-5-fluoropyrimidin-2-amine |
| II-20 | 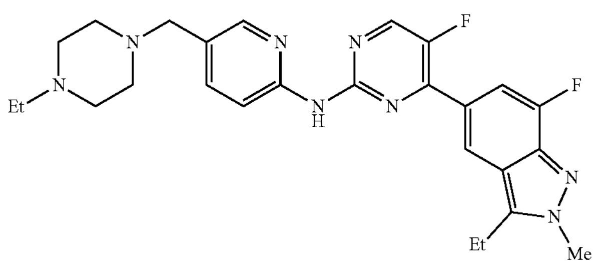 [SMILES: CCc1c2cc(-c3nc(Nc4ccc(CN5CCN(CC)CC5)cn4)ncc3F)cc(F)c2nn1C] | 4-(3-ethyl-7-fluoro-2-methyl-2H-indazol-5-yl)-N-(5-((4-ethylpiperazin-1-yl)methyl)pyridin-2-yl)-5-fluoropyrimidin-2-amine |
| II-21 | 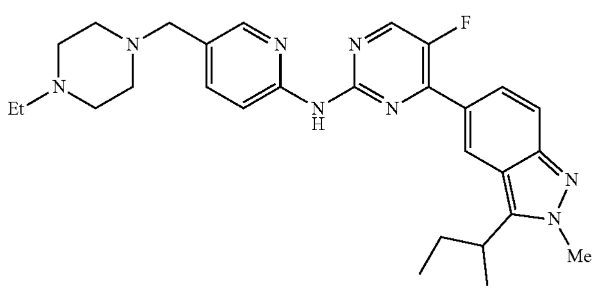 [SMILES: CCC(C)c1c2cc(-c3nc(Nc4ccc(CN5CCN(CC)CC5)cn4)ncc3F)ccc2nn1C] | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| II-22 | 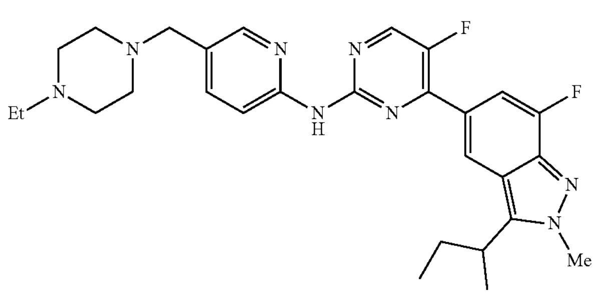 [SMILES: CCC(C)c1c2cc(-c3nc(Nc4ccc(CN5CCN(CC)CC5)cn4)ncc3F)cc(F)c2nn1C] | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |

-continued

| Example | Structure | Name |
|---|---|---|
| II-23 | 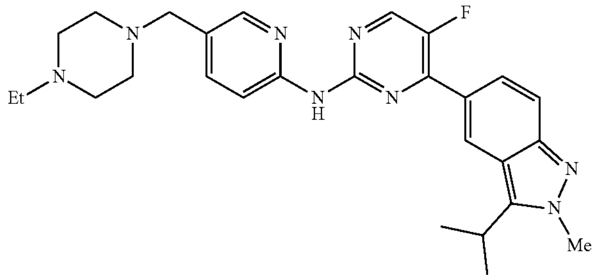 [SMILES: CCN1CCN(Cc2ccc(Nc3ncc(F)c(-c4ccc5nn(C)c(C(C)C)c5c4)n3)nc2)CC1] | 4-(2-ethyl-3-isopropyl-2H-indazol-5-yl)-N-(5-((4-ethylpiperazin-1-yl)methyl)pyridin-2-yl)-5-fluoropyrimidin-2-amine |
| II-24 | 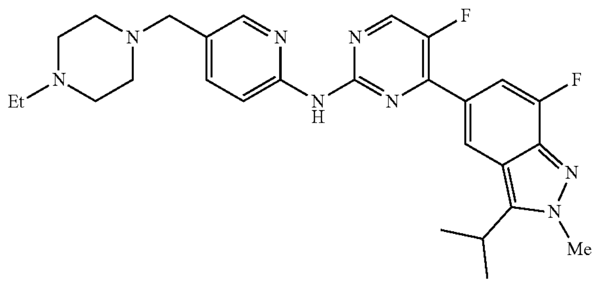 [SMILES: CCN1CCN(Cc2ccc(Nc3ncc(F)c(-c4cc(F)c5nn(C)c(C(C)C)c5c4)n3)nc2)CC1] | 4-(2-ethyl-7-fluoro-3-isopropyl-2H-indazol-5-yl)-N-(5-((4-ethylpiperazin-1-yl)methyl)pyridin-2-yl)-5-fluoropyrimidin-2-amine |
| II-25 | 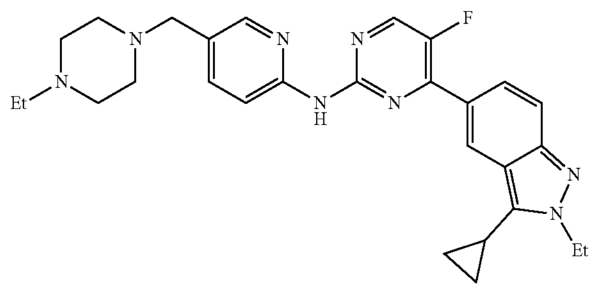 [SMILES: CCN1CCN(Cc2ccc(Nc3ncc(F)c(-c4ccc5nn(CC)c(C6CC6)c5c4)n3)nc2)CC1] | 4-(3-cyclopropyl-2-ethyl-2H-indazol-5-yl)-N-(5-((4-ethylpiperazin-1-yl)methyl)pyridin-2-yl)-5-fluoropyrimidin-2-amine |
| II-26 | 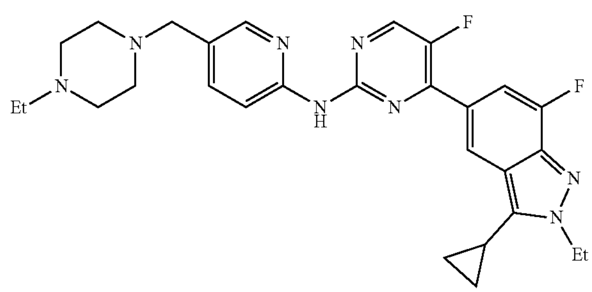 [SMILES: CCN1CCN(Cc2ccc(Nc3ncc(F)c(-c4cc(F)c5nn(CC)c(C6CC6)c5c4)n3)nc2)CC1] | 4-(3-cyclopropyl-2-ethyl-7-fluoro-2H-indazol-5-yl)-N-(5-((4-ethylpiperazin-1-yl)methyl)pyridin-2-yl)-5-fluoropyrimidin-2-amine |
| II-27 | 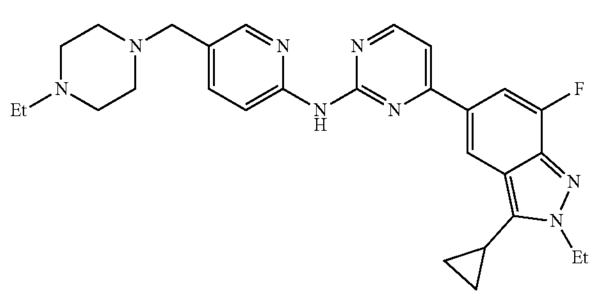 [SMILES: CCN1CCN(Cc2ccc(Nc3nccc(-c4cc(F)c5nn(CC)c(C6CC6)c5c4)n3)nc2)CC1] | 4-(3-(cyclopropylmethyl)-2-methyl-2H-indazol-5-yl)-N-(5-((4-ethylpiperazin-1-yl)methyl)pyridin-2-yl)-5-fluoropyrimidin-2-amine |

-continued

| Example | Name |
|---------|------|
| II-28 | 4-(3-(cyclopropylmethyl)-7-fluoro-2-methyl-2H-indazol-5-yl)-N-(5-((4-ethylpiperazin-1-yl)methyl)pyridin-2-yl)-5-fluoropyrimidin-2-amine |
| II-29 | 4-(3-cyclopropyl-2-ethyl-7-fluoro-2H-indazol-5-yl)-N-(5-((4-ethylpiperazin-1-yl)methyl)pyridin-2-yl)pyrimidin-2-amine |
| II-30 | 4-(3-(sec-butyl)-2-methyl-2H-indazol-5-yl)-N-(5-((4-ethylpiperazin-1-yl)methyl)pyridin-2-yl)-5-fluoropyrimidin-2-amine |
| II-31 | 4-(3-(sec-butyl)-7-fluoro-2-methyl-2H-indazol-5-yl)-N-(5-((4-ethylpiperazin-1-yl)methyl)pyridin-2-yl)-5-fluoropyrimidin-2-amine |
| II-32 | 5-fluoro-4-(3-isopropyl-2-methyl-2H-indazol-5-yl)-N-(5-(piperazin-1-ylmethyl)pyridin-2-yl)pyrimidin-2-amine |

| Example | Structure | Name |
|---|---|---|
| II-33 | 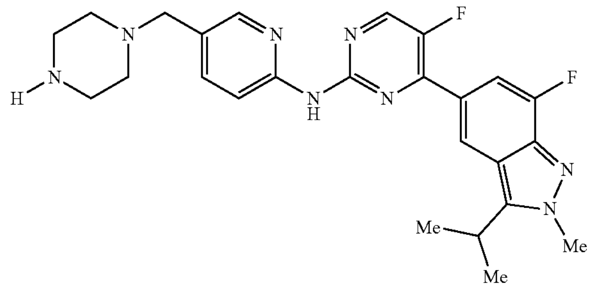 [SMILES: CC(C)c1c2cc(-c3nc(Nc4ccc(CN5CCNCC5)cn4)ncc3F)cc(F)c2nn1C] | 5-fluoro-4-(7-fluoro-3-isopropyl-2-methyl-2H-indazol-5-yl)-N-(5-(piperazin-1-ylmethyl)pyridin-2-yl)pyrimidin-2-amine |
| II-34 | 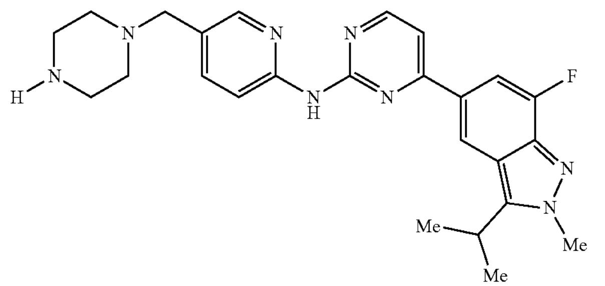 [SMILES: CC(C)c1c2cc(-c3ccnc(Nc4ccc(CN5CCNCC5)cn4)n3)cc(F)c2nn1C] | 4-(7-fluoro-3-isopropyl-2-methyl-2H-indazol-5-yl)-N-(5-(piperazin-1-ylmethyl)pyridin-2-yl)pyrimidin-2-amine. |

8. The method of claim 1, wherein:
G is selected from the group consisting of 1H-indol-3-yl, 1-methyl-1H-indol-3-yl, 1-(2-fluoroethyl)-1H-indol-3-yl, 1,2-dimethyl-1H-indol-3-yl, pyrazolo[1,5-a]-pyridin-3-yl, 4,5,6,7-tetrahydropyrazolo[1,5-a]pyridin-3-yl, 1-methyl-1H-indazol-3-yl, and 2-methyl-2H-indazol-3-yl; $R^1$ is hydrogen, halogen, or methyl; $R^2$ is hydrogen, F, or Cl; $R^3$ is hydrogen, F, Cl, or —$CF_3$; $R^1$ is hydrogen or halogen; and $R^5$ is selected from $C_1$-$C_6$ alkyl, substituted or unsubstituted azetidinyl, substituted or unsubstituted pyrrolidinyl, substituted or unsubstituted piperidinyl, $R^7R^8N$—$(CH_2)_n$— (n=1 to 5), $R^7R^8N$—($C_3$-$C_6$ cycloalkyl)-$(CH_2)_m$— (m=1 to 3), wherein $R^7$ and $R^8$ are the same or different and are independently selected from hydrogen and lower alkyl.

9. The method of claim 1, wherein:
$R^1$ to $R^4$ are each hydrogen; and $R^5$ is selected from methyl, 1-(dimethylamino)-cyclopropylmethyl, 3-(dimethylamino)cyclobutyl, 1-methylazetidin-3-yl, (R)-1-methylpyrrolidin-3-yl, (S)-1-methylpyrrolidin-3-yl, and 1-methylpiperidin-4-yl, and 2-dimethylaminoethyl.

10. The method of claim 1, wherein the compound of formula (I) is a compound of formula (Ia):

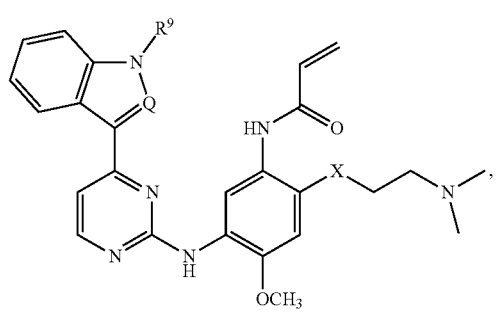

(Ia)

or a pharmaceutically acceptable salt, solvate, or prodrug thereof, wherein:
X is O, S, or $CH_2$;
Q is C—$R^{10}$ or N
$R^9$ is $CH_3$ or $CH_2CH_2F$; and
$R^{10}$ is H or $CH_3$.

11. The method of claim 1, wherein the compound of formula (I) is selected from the group consisting of:

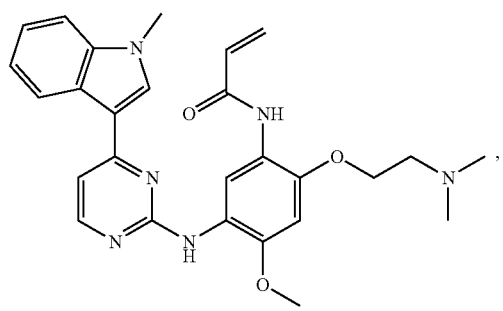

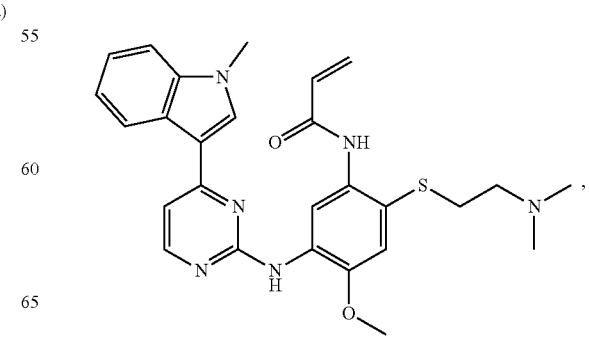

69
-continued
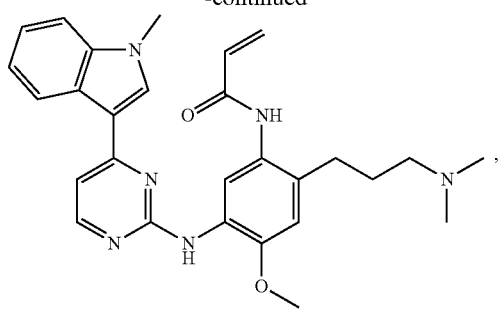
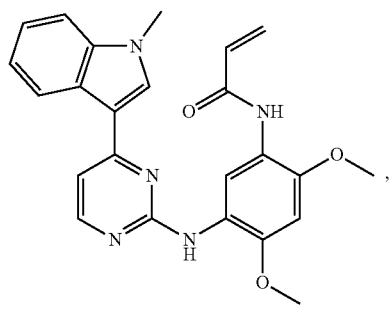
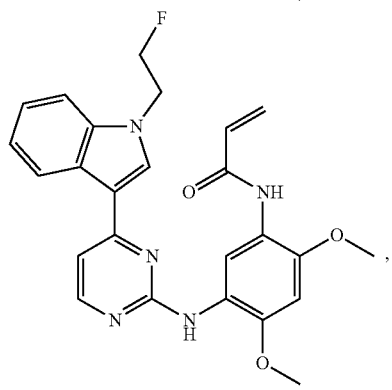
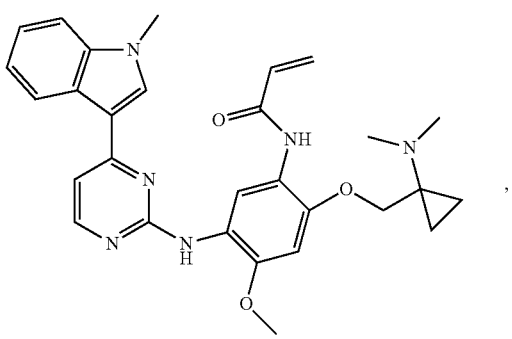
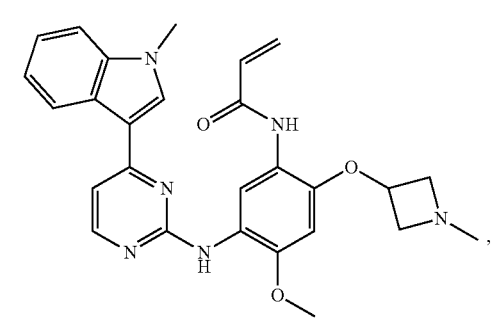
70
-continued
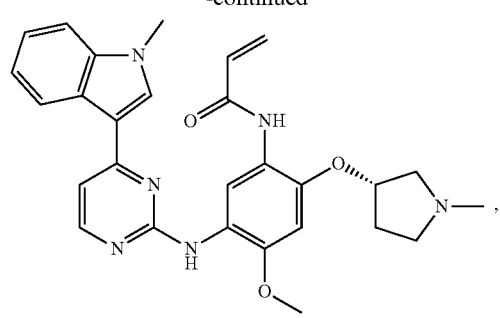
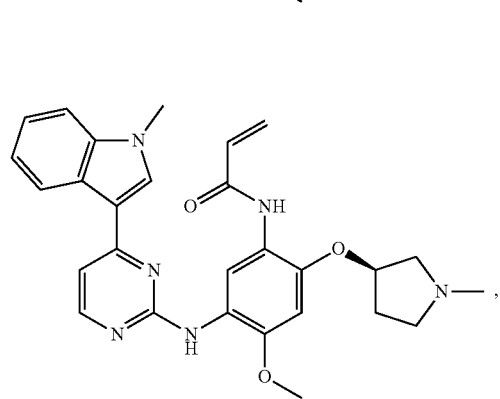
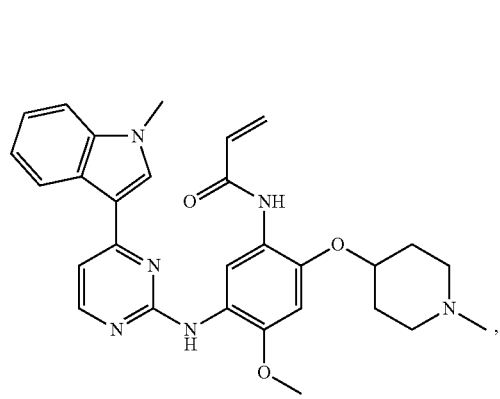
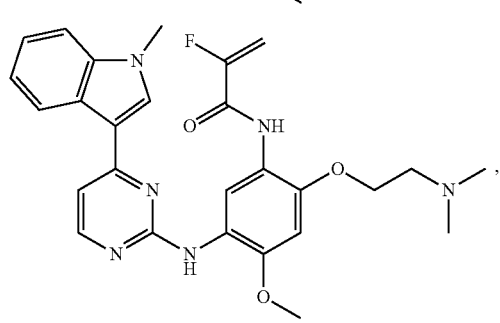
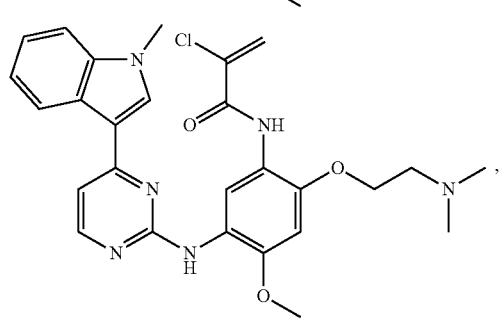

-continued
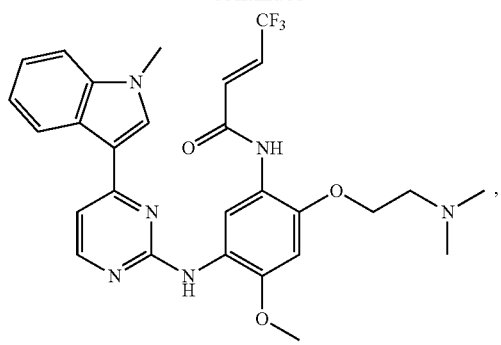
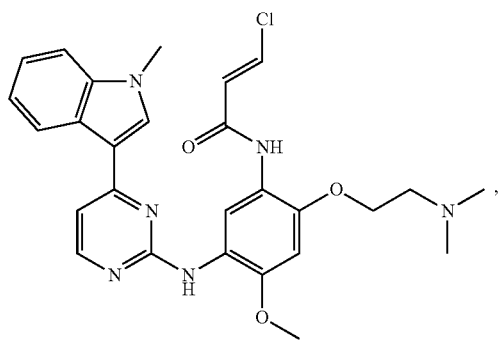
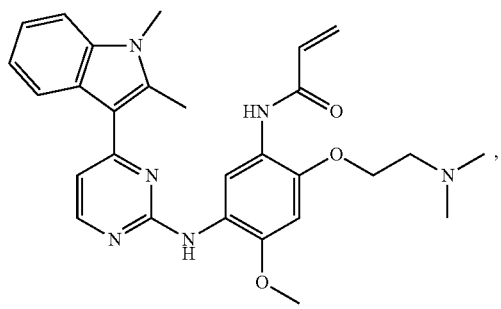
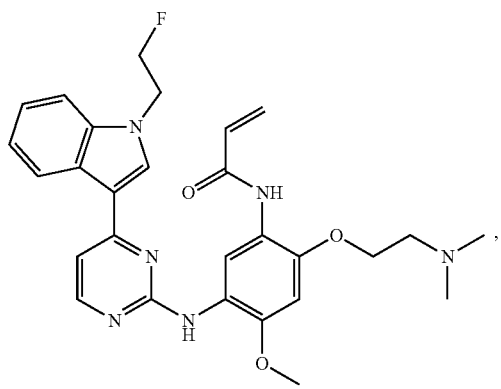
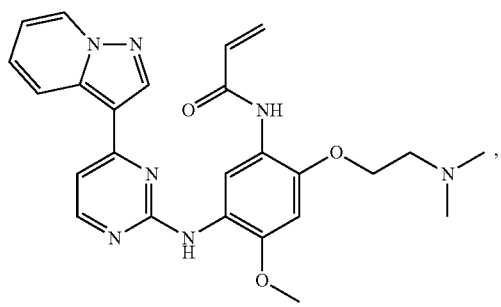
-continued
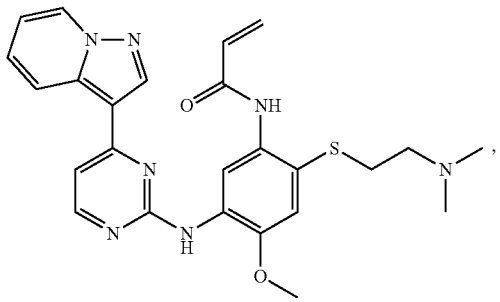
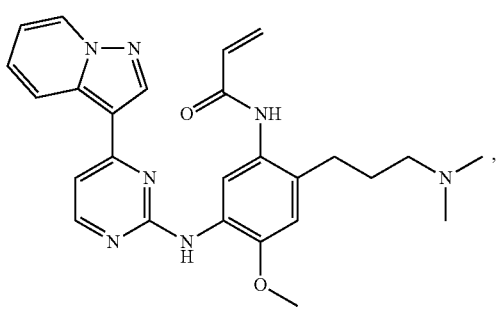
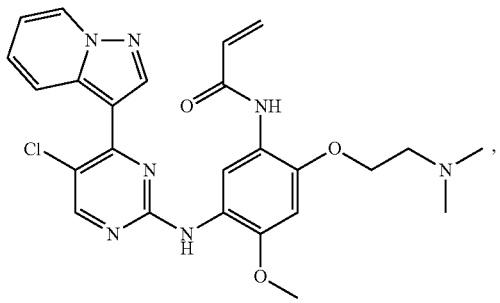
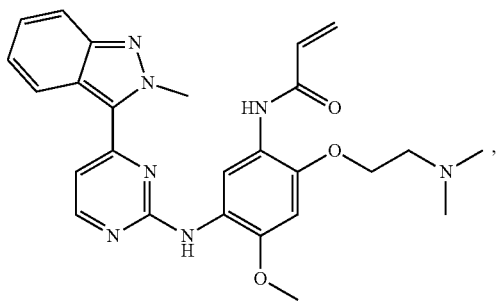
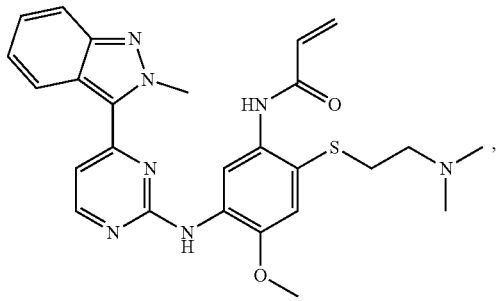

-continued
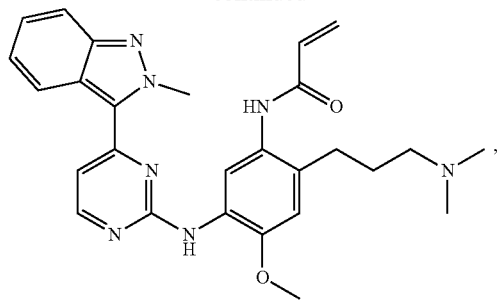
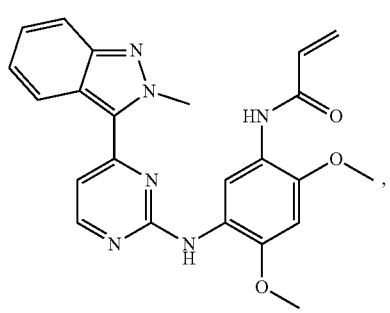
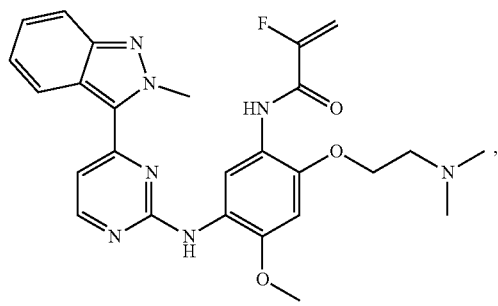
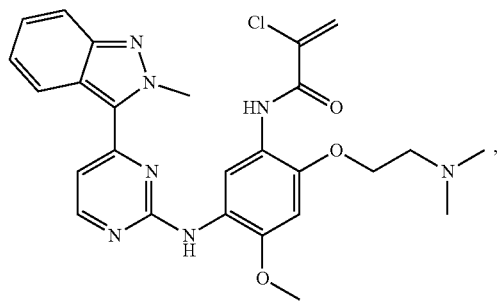
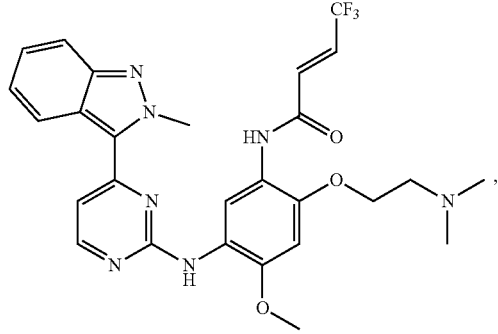
-continued
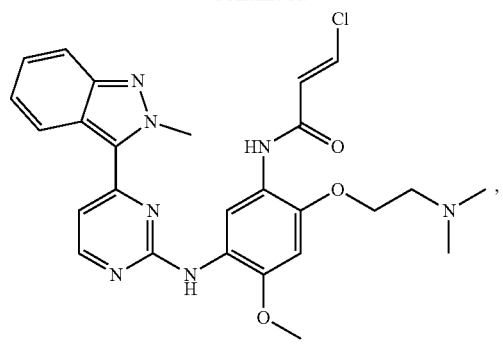
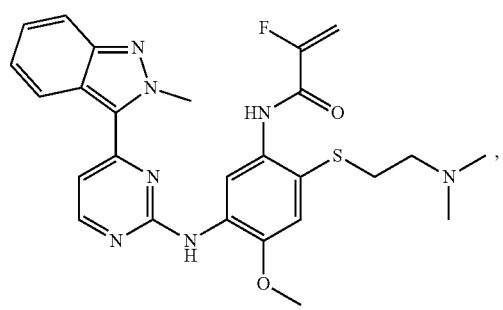
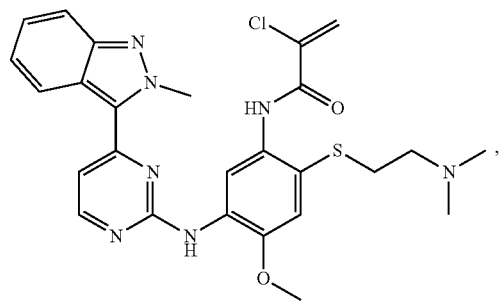
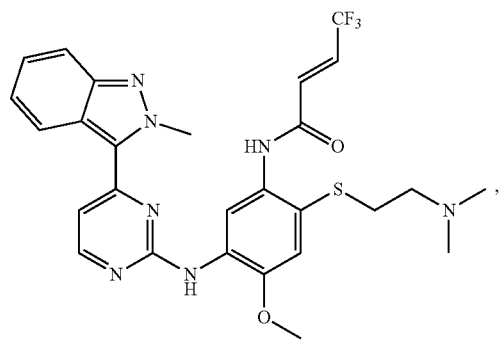
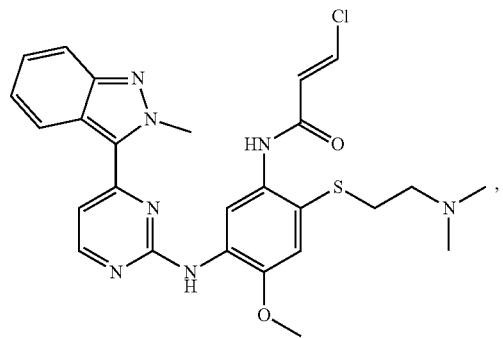

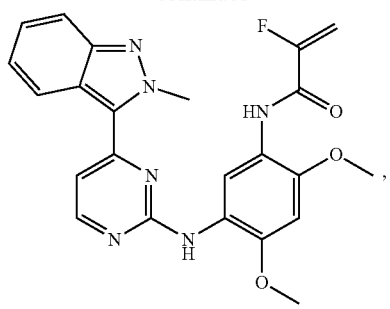
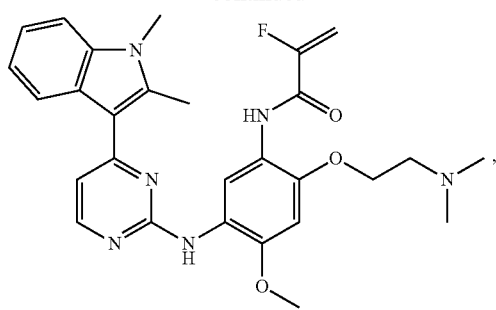
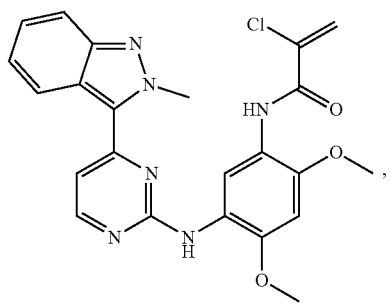
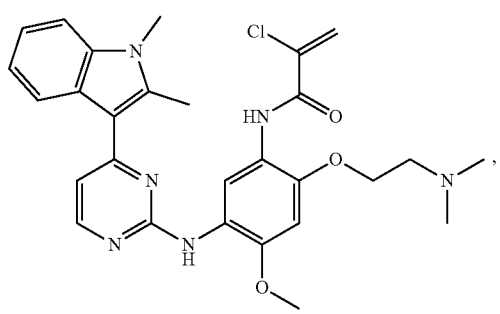
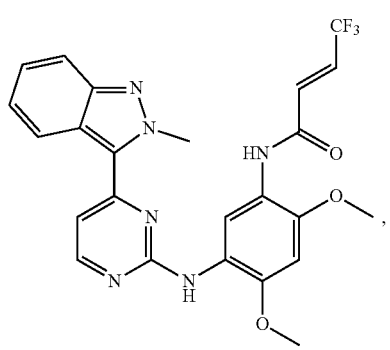
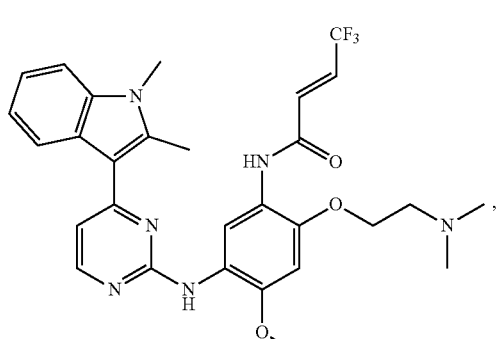
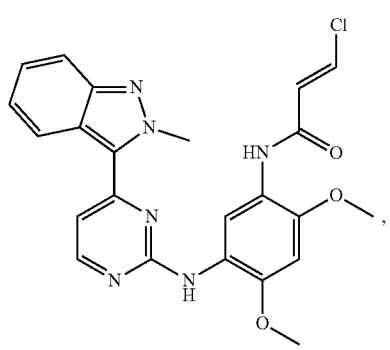
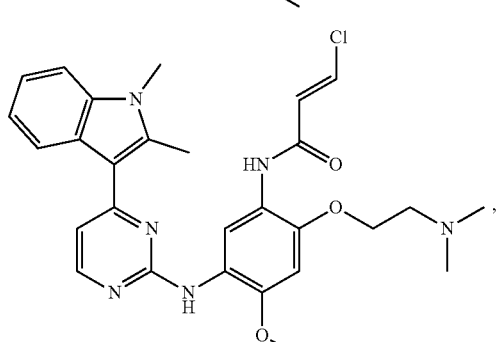
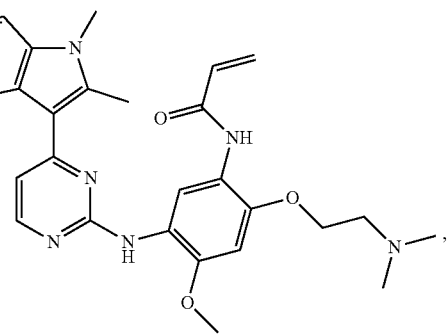
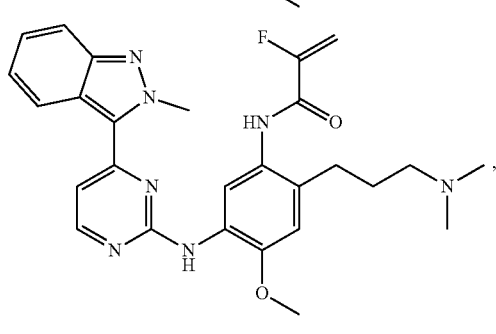

77
-continued
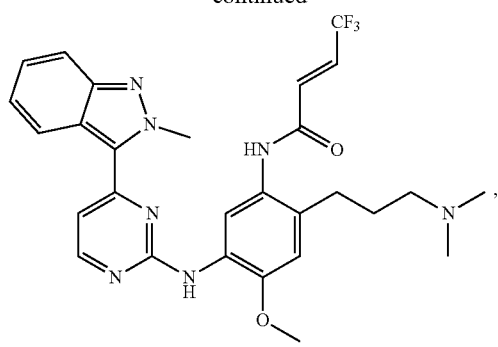
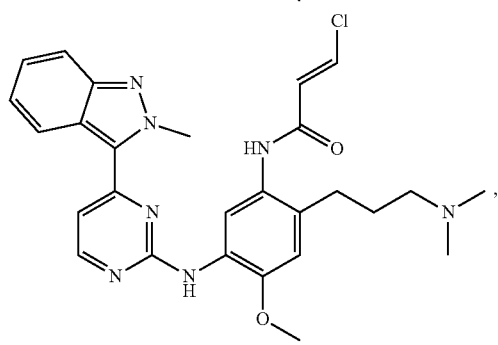
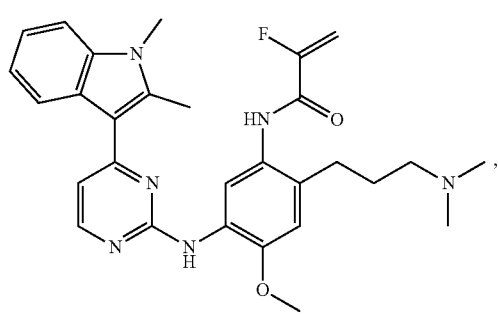
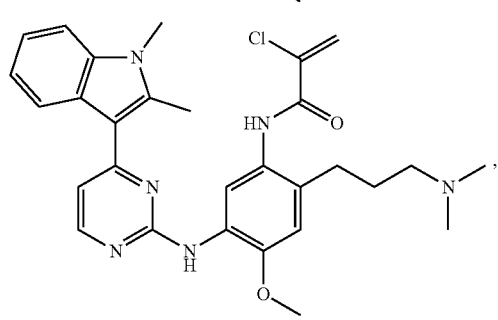
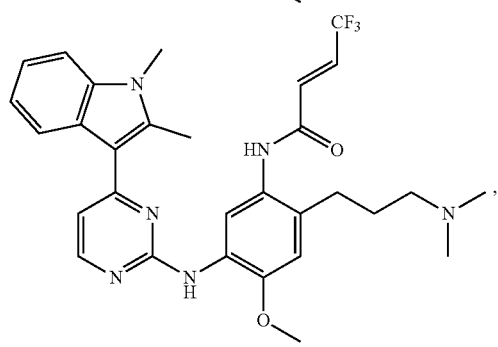
78
-continued
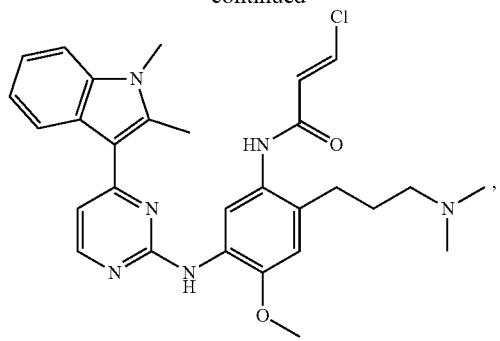
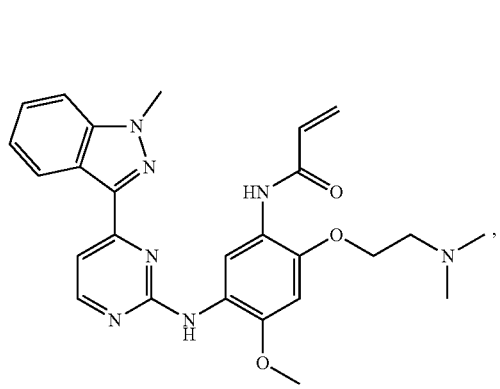
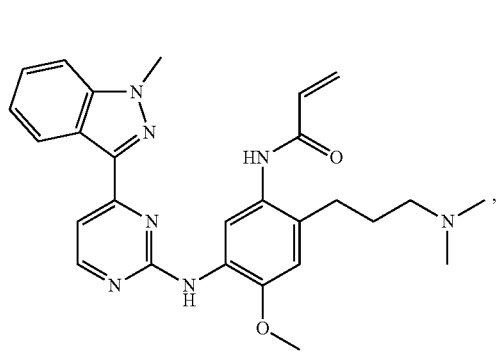
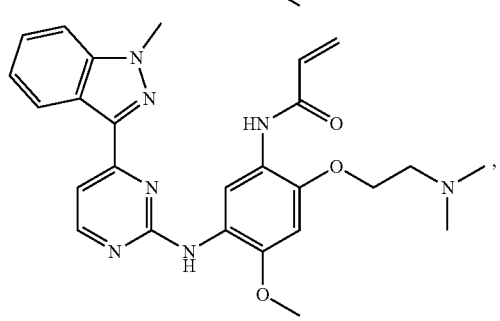
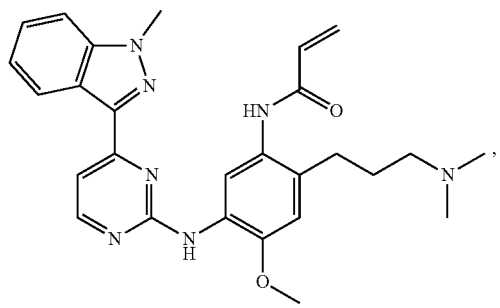

79
-continued
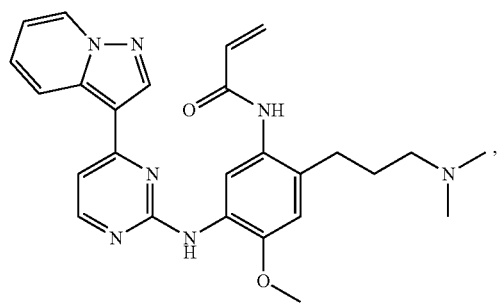
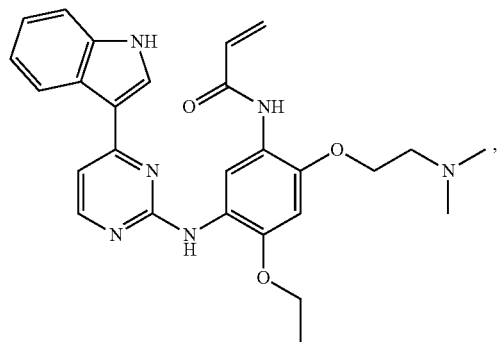
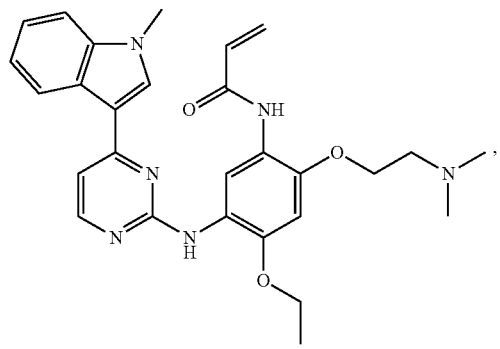
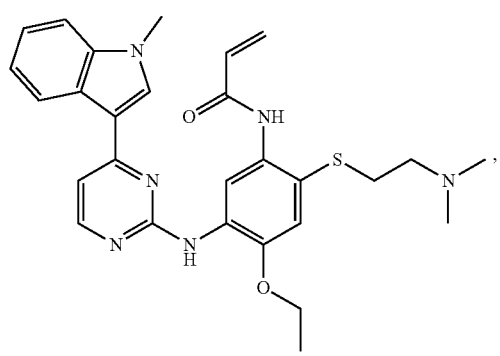
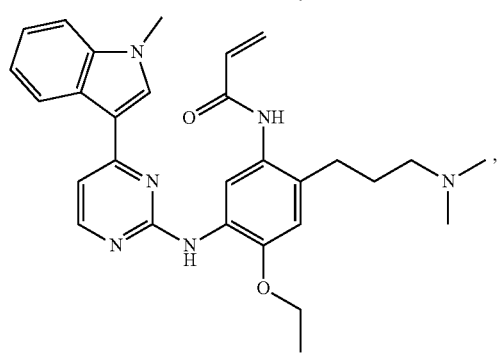
80
-continued
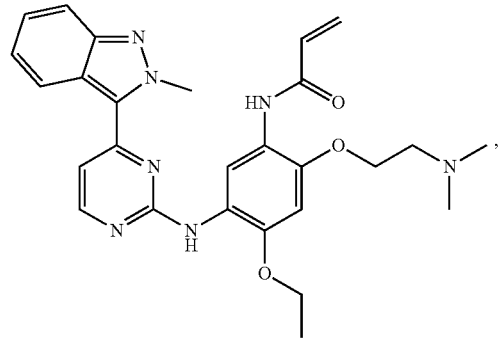
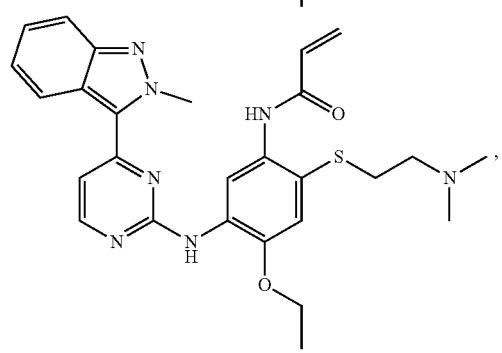
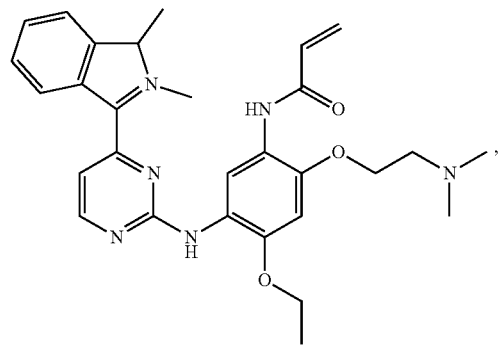
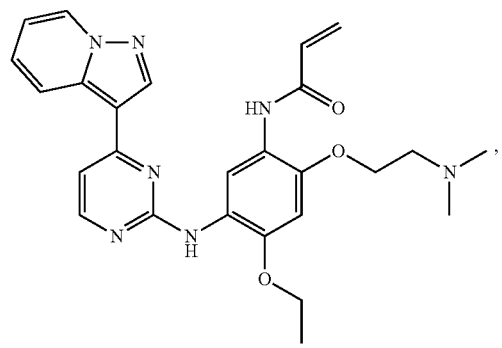
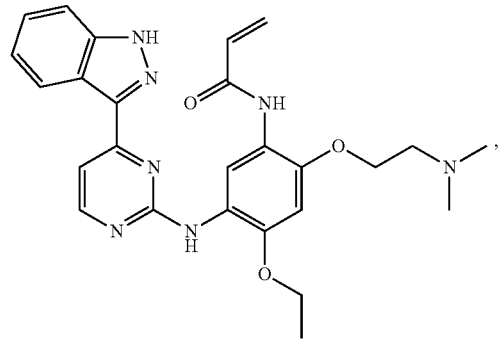

-continued
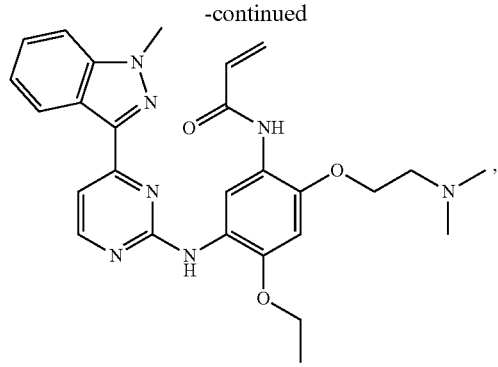
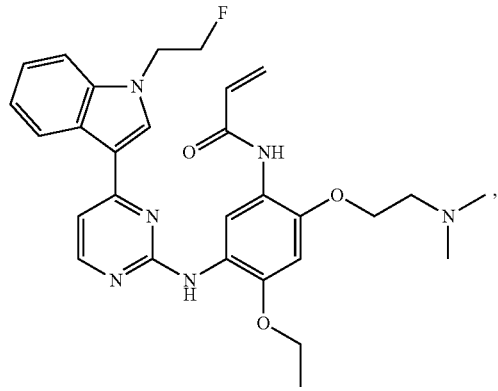
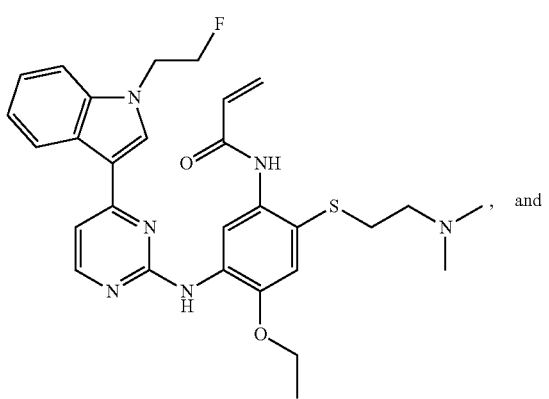
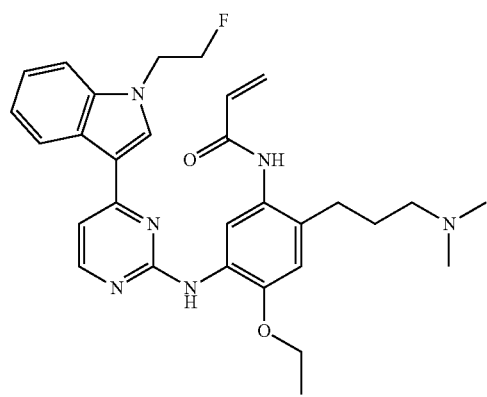 [SMILES: C=CC(=O)Nc1cc(Nc2nccc(-c3cn(CCF)c4ccccc34)n2)c(OCC)cc1CCCN(C)C]
or a pharmaceutically acceptable salt, solvate, or prodrug thereof.
12. The method of claim 1, where the compound of formula (I) is selected from the group consisting of:
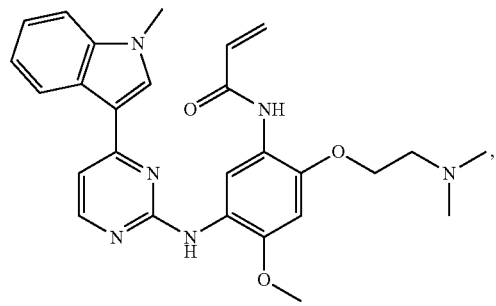
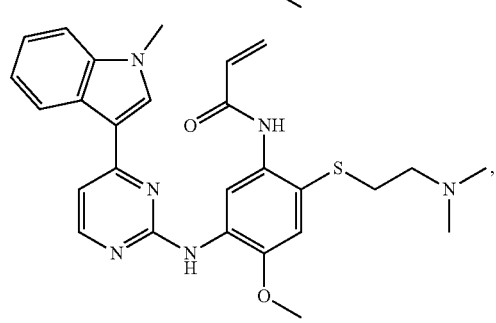
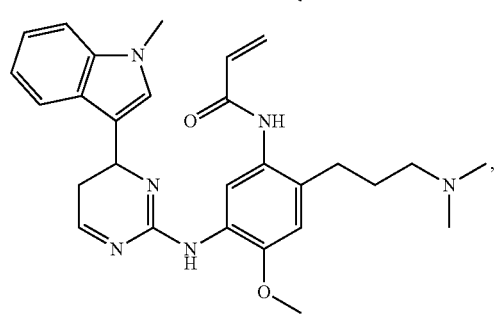
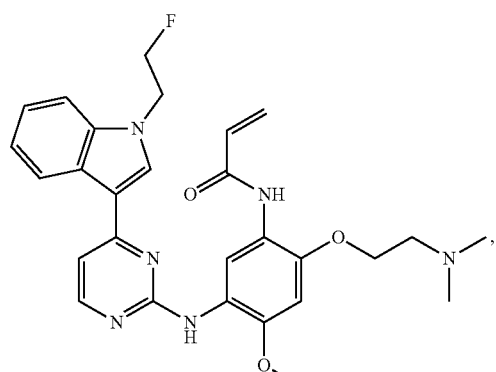
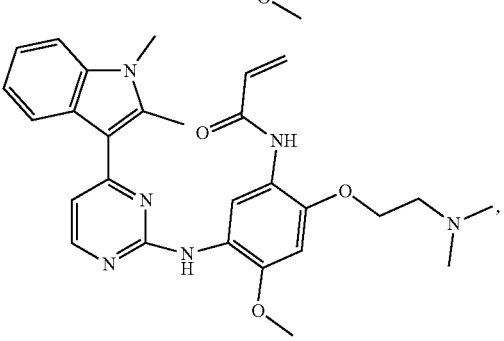

-continued

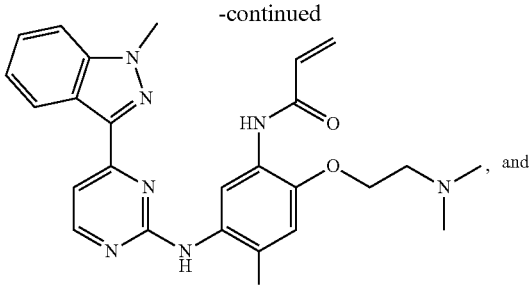
, and

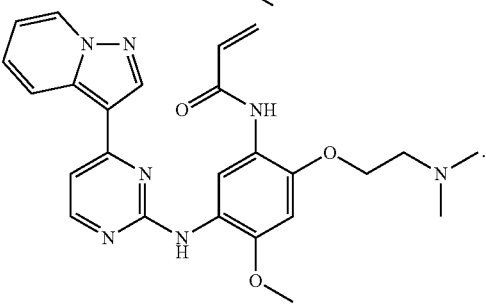
.

13. A method of treating a human subject having non-small cell lung carcinoma harboring an EGFR mutation, comprising a step of administering an effective amount of an EGFR tyrosine kinase inhibitor of Formula 1

(1)

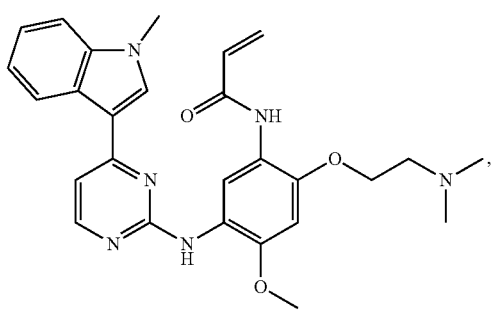

or a pharmaceutically acceptable salt thereof, in combination with a synergistically effective amount of a CDK4/6 inhibitor of Formula 2

(2)

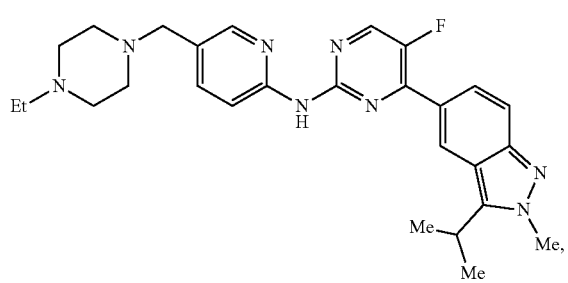

or a pharmaceutically acceptable salt thereof; wherein the synergistically effective amount formula 2 comprises approximately 6.25 to 100 mg/kg of formula 2.

14. The method claim 13, wherein the non-small cell lung carcinoma harbors an EGFR T790M resistance mutation.

15. The method claim 13, wherein the salt form of the inhibitor of Formula 1 is a methanesulfonate, and the salt form of the inhibitor of Formula 2 is a hydrochloride.

16. A method of treating a human subject having an EGFR-mutant cancer that has developed an acquired resistance to an epidermal growth factor receptor tyrosine kinase inhibitor (EGFR-TKI) treatment, comprising a step of administering to the human subject an effective amount of an EGFR tyrosine kinase inhibitor of Formula 1

(1)

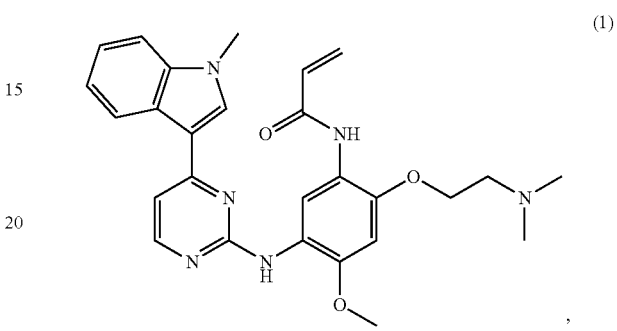

or a pharmaceutically acceptable salt thereof, in combination with a synergistically effective amount of a CDK4/6 inhibitor of Formula 2, (2)

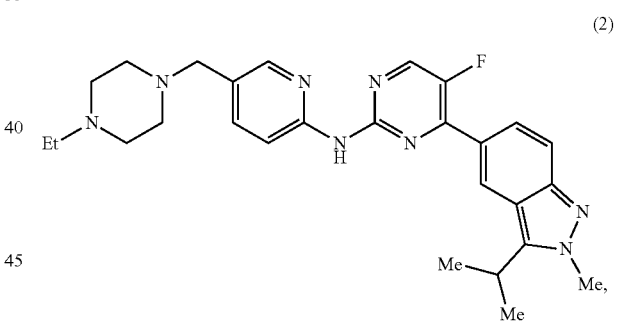

or a pharmaceutically acceptable salt thereof; wherein the synergistically effective amount formula 2 comprises approximately 6.25 to 100 mg/kg of formula 2.

17. The method of claim 16, wherein the EGFR-mutant cancer is breast cancer.

18. The method of claim 17, wherein the breast cancer is estrogen receptor-positive breast cancer, progesterone receptor-positive breast cancer, or HER2-positive breast cancer.

19. The method of claim 16, wherein the EGFR-mutant cancer is bladder cancer, glioblastoma, head and neck cancer, cervical cancer, uterine cancer, colorectal cancer, gastroesophageal cancer, prostate cancer, ovarian cancer, pancreatic cancer, renal cell carcinoma, squamous cell carcinoma, or thyroid cancer.

20. A method of treating a human subject having an EGFR-mutant cancer, wherein the subject is EGFR-TKI-treatment naive, comprising a step of administering to the human subject an effective amount of an EGFR tyrosine kinase inhibitor of Formula 1

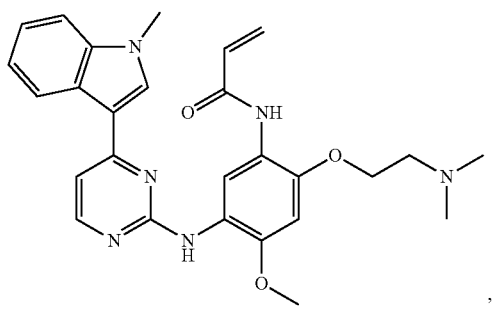
(1)

or a pharmaceutically acceptable salt thereof, with a synergistically effective amount of a CDK4/6 inhibitor of Formula 2

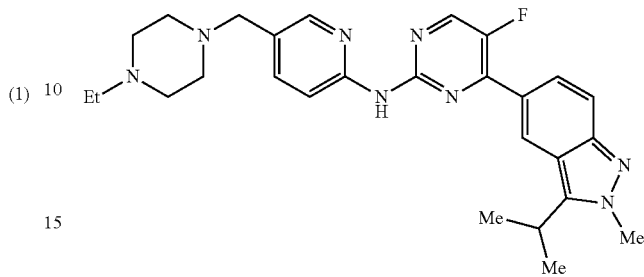
(2)

or a pharmaceutically acceptable salt thereof; wherein the synergistically effective amount formula 2 comprises approximately 6.25 to 100 mg/kg of formula 2.

* * * * *